US 8,219,208 B2

(12) United States Patent
Stevenson et al.

(10) Patent No.: US 8,219,208 B2
(45) Date of Patent: *Jul. 10, 2012

(54) FREQUENCY SELECTIVE PASSIVE COMPONENT NETWORKS FOR ACTIVE IMPLANTABLE MEDICAL DEVICES UTILIZING AN ENERGY DISSIPATING SURFACE

(75) Inventors: Robert A. Stevenson, Canyon Country, CA (US); Warren S. Dabney, Orchard Park, NY (US); Christine A. Frysz, Orchard Park, NY (US); Buehl E. Truex, Glendora, CA (US); Henry R. Halperin, Pikesville, MD (US); Albert C. Lardo, Baltimore, MD (US)

(73) Assignee: Greatbatch Ltd., Clarence, NY (US)

( * ) Notice: Subject to any disclaimer, the term of this patent is extended or adjusted under 35 U.S.C. 154(b) by 17 days.

This patent is subject to a terminal disclaimer.

(21) Appl. No.: 12/751,711

(22) Filed: Mar. 31, 2010

(65) Prior Publication Data
US 2010/0217262 A1    Aug. 26, 2010

Related U.S. Application Data

(63) Continuation-in-part of application No. 12/489,921, filed on Jun. 23, 2009, now Pat. No. 7,751,903, which is a continuation-in-part of application No. 10/123,534, filed on Apr. 15, 2002, now Pat. No. 7,844,319.

(60) Provisional application No. 60/283,725, filed on Apr. 13, 2001.

(51) Int. Cl.
*A61N 1/08* (2006.01)
*A61N 1/05* (2006.01)

(52) U.S. Cl. ............................................ 607/63; 607/60
(58) Field of Classification Search .................. 607/9, 2, 607/63, 48, 60, 45
See application file for complete search history.

(56) References Cited

U.S. PATENT DOCUMENTS

| | | |
|---|---|---|
| 2,569,000 A | 9/1951 | Bertram |
| 3,871,382 A | 3/1975 | Mann |
| 3,968,802 A | 7/1976 | Ballis |
| 4,295,467 A | 10/1981 | Mann et al. |
| 4,431,005 A | 2/1984 | McCormick |
| 4,445,501 A | 5/1984 | Bresler |
| 4,572,198 A | 2/1986 | Codrington |
| 4,633,181 A | 12/1986 | Murphy-Boesch et al. |
| 4,643,186 A | 2/1987 | Rosen et al. |
| 4,654,880 A | 3/1987 | Sontag |
| 4,672,972 A | 6/1987 | Berke |
| 4,682,125 A | 7/1987 | Harrison et al. |
| 4,689,621 A | 8/1987 | Kleinberg |

(Continued)

FOREIGN PATENT DOCUMENTS
EP          0243573          11/1987
(Continued)

*Primary Examiner* — Carl H. Layno
*Assistant Examiner* — Jon-Eric C. Morales
(74) *Attorney, Agent, or Firm* — Michael F. Scalise

(57) ABSTRACT

Decoupling circuits are provided which transfer energy induced from an MRI pulsed RF field to the housing for an active implantable medical device (AIMD) which serves as an energy dissipating surface. This is accomplished through broadband filtering or by resonant filtering. In a passive component network for an AIMD, a frequency selective energy diversion circuit is provided for diverting high-frequency energy away from an AIMD lead to the AIMD housing for dissipation of said high-frequency energy.

56 Claims, 42 Drawing Sheets

U.S. PATENT DOCUMENTS

| | | | | |
|---|---|---|---|---|
| 4,754,752 | A | 7/1988 | Ginsburg et al. | |
| 4,757,820 | A | 7/1988 | Itoh | |
| 4,766,381 | A | 8/1988 | Conturo et al. | |
| 4,799,499 | A | 1/1989 | Bisping | |
| 4,813,429 | A | 3/1989 | Eshel et al. | |
| 4,823,812 | A | 4/1989 | Eshel et al. | |
| 4,832,023 | A | 5/1989 | Murphy-Chutorian et al. | |
| 4,858,623 | A | 8/1989 | Bradshaw et al. | |
| 4,859,950 | A | 8/1989 | Keren | |
| 4,932,411 | A | 6/1990 | Fritschy et al. | |
| 4,951,672 | A | 8/1990 | Buchwald et al. | |
| 4,960,106 | A | 10/1990 | Kubokawa | |
| 4,989,608 | A | 2/1991 | Ratner | |
| 5,019,075 | A | 5/1991 | Spears et al. | |
| 5,095,911 | A | 3/1992 | Pomeranz | |
| 5,099,208 | A | 3/1992 | Fitzpatrick et al. | |
| 5,167,233 | A | 12/1992 | Eberle et al. | |
| 5,170,789 | A | 12/1992 | Narayan et al. | |
| 5,178,616 | A | 1/1993 | Ognier | |
| 5,190,046 | A | 3/1993 | Shturman | |
| 5,209,233 | A | 5/1993 | Holland et al. | |
| 5,211,165 | A | 5/1993 | Dumoulin et al. | |
| 5,217,010 | A | 6/1993 | Tsitlik et al. | |
| 5,246,438 | A | 9/1993 | Langberg | |
| 5,271,400 | A | 12/1993 | Dumoulin et al. | |
| 5,300,108 | A | 4/1994 | Rebell et al. | |
| 5,307,808 | A | 5/1994 | Dumoulin et al. | |
| 5,307,814 | A | 5/1994 | Kressel et al. | |
| 5,315,025 | A | 5/1994 | Bushell et al. | |
| 5,318,025 | A | 6/1994 | Dumoulin et al. | |
| 5,323,776 | A | 6/1994 | Blakeley et al. | |
| 5,323,778 | A | 6/1994 | Kandarpa et al. | |
| 5,333,095 | A | 7/1994 | Stevenson et al. | |
| 5,334,045 | A * | 8/1994 | Cappa et al. | 439/506 |
| 5,334,193 | A | 8/1994 | Nardella | |
| 5,348,010 | A | 9/1994 | Schnall et al. | |
| 5,352,979 | A | 10/1994 | Conturo | |
| 5,355,087 | A | 10/1994 | Claiborne et al. | |
| 5,358,515 | A | 10/1994 | Hurter et al. | |
| 5,363,845 | A | 11/1994 | Chowdhury et al. | |
| 5,365,928 | A | 11/1994 | Rhinehart et al. | |
| 5,370,644 | A | 12/1994 | Langberg | |
| 5,398,683 | A | 3/1995 | Edwards et al. | |
| 5,400,787 | A | 3/1995 | Marandos | |
| 5,413,104 | A | 5/1995 | Buijs et al. | |
| 5,419,325 | A | 5/1995 | Dumoulin et al. | |
| 5,433,717 | A | 7/1995 | Rubinsky et al. | |
| 5,437,277 | A | 8/1995 | Dumoulin et al. | |
| 5,443,066 | A | 8/1995 | Dumoulin et al. | |
| 5,443,489 | A | 8/1995 | Ben-Haim | |
| 5,447,156 | A | 9/1995 | Dumoulin et al. | |
| 5,451,232 | A | 9/1995 | Rhinehart et al. | |
| 5,462,055 | A | 10/1995 | Casey et al. | |
| 5,476,095 | A | 12/1995 | Schnall et al. | |
| 5,498,261 | A | 3/1996 | Strul | |
| 5,507,743 | A | 4/1996 | Edwards et al. | |
| 5,512,825 | A | 4/1996 | Atalar et al. | |
| 5,514,173 | A | 5/1996 | Rebell et al. | |
| 5,540,679 | A | 7/1996 | Fram et al. | |
| 5,540,959 | A | 7/1996 | Wang | |
| 5,545,201 | A | 8/1996 | Helland et al. | |
| 5,558,093 | A | 9/1996 | Pomeranz | |
| 5,578,008 | A | 11/1996 | Hara | |
| 5,588,432 | A | 12/1996 | Crowley | |
| 5,590,657 | A | 1/1997 | Cain et al. | |
| 5,620,476 | A | 4/1997 | Truex et al. | |
| 5,623,241 | A | 4/1997 | Minkoff | |
| 5,629,622 | A | 5/1997 | Scampini | |
| 5,647,361 | A | 7/1997 | Damadian | |
| 5,662,108 | A | 9/1997 | Budd et al. | |
| 5,682,897 | A | 11/1997 | Pomeranz | |
| 5,685,878 | A | 11/1997 | Falwell et al. | |
| 5,697,958 | A | 12/1997 | Paul et al. | |
| 5,699,801 | A | 12/1997 | Atalar et al. | |
| 5,706,810 | A | 1/1998 | Rubinsky et al. | |
| 5,715,825 | A | 2/1998 | Crowley | |
| 5,716,390 | A | 2/1998 | Li | |
| 5,722,998 | A | 3/1998 | Prutchi et al. | |
| 5,735,887 | A * | 4/1998 | Barreras et al. | 607/60 |
| 5,741,321 | A | 4/1998 | Brennen | |
| 5,751,539 | A | 5/1998 | Stevenson et al. | |
| 5,759,202 | A | 6/1998 | Schroeppel | |
| 5,769,800 | A | 6/1998 | Gelfand et al. | |
| 5,775,338 | A | 7/1998 | Hastings | |
| 5,779,669 | A | 7/1998 | Haissaguerre et al. | |
| 5,782,891 | A | 7/1998 | Hassler et al. | |
| 5,792,055 | A | 8/1998 | McKinnon | |
| 5,814,076 | A | 9/1998 | Brownlee | |
| 5,827,997 | A | 10/1998 | Chung et al. | |
| 5,833,608 | A | 11/1998 | Acker | |
| 5,836,992 | A | 11/1998 | Thompson et al. | |
| 5,840,031 | A | 11/1998 | Crowley | |
| 5,864,234 | A | 1/1999 | Ludeke | |
| 5,868,674 | A | 2/1999 | Glowinski et al. | |
| 5,879,347 | A | 3/1999 | Saadat | |
| 5,891,134 | A | 4/1999 | Goble et al. | |
| 5,896,267 | A | 4/1999 | Hittman et al. | |
| 5,905,627 | A | 5/1999 | Brendel et al. | |
| 5,916,162 | A | 6/1999 | Snelten et al. | |
| 5,928,145 | A | 7/1999 | Ocali et al. | |
| 5,928,159 | A | 7/1999 | Eggers et al. | |
| 5,938,609 | A | 8/1999 | Pomeranz | |
| 5,938,692 | A | 8/1999 | Rudie | |
| 5,959,829 | A | 9/1999 | Stevenson et al. | |
| 5,963,856 | A | 10/1999 | Kim | |
| 5,964,705 | A | 10/1999 | Truwit et al. | |
| 5,973,906 | A | 10/1999 | Stevenson et al. | |
| 5,978,204 | A | 11/1999 | Stevenson | |
| 6,004,269 | A | 12/1999 | Crowley et al. | |
| 6,008,980 | A | 12/1999 | Stevenson et al. | |
| 6,011,995 | A | 1/2000 | Guglielmi et al. | |
| 6,026,316 | A | 2/2000 | Kucharczyk et al. | |
| 6,027,500 | A | 2/2000 | Buckles et al. | |
| 6,031,375 | A | 2/2000 | Atalar et al. | |
| 6,045,532 | A | 4/2000 | Eggers et al. | |
| 6,055,457 | A | 4/2000 | Bonner | |
| 6,066,136 | A | 5/2000 | Geistert | |
| 6,101,417 | A | 8/2000 | Vogel et al. | |
| 6,128,522 | A | 10/2000 | Acker et al. | |
| 6,129,670 | A | 10/2000 | Burdette et al. | |
| 6,141,594 | A | 10/2000 | Flynn et al. | |
| 6,159,560 | A | 12/2000 | Stevenson et al. | |
| 6,171,240 | B1 | 1/2001 | Young et al. | |
| 6,171,241 | B1 | 1/2001 | McVeigh et al. | |
| 6,188,219 | B1 | 2/2001 | Reeder et al. | |
| 6,226,545 | B1 | 5/2001 | Gilderdale | |
| 6,236,205 | B1 | 5/2001 | Ludeke et al. | |
| 6,238,390 | B1 | 5/2001 | Tu et al. | |
| 6,263,229 | B1 | 7/2001 | Atalar et al. | |
| 6,272,370 | B1 | 8/2001 | Gillies et al. | |
| 6,275,369 | B1 | 8/2001 | Stevenson et al. | |
| 6,280,385 | B1 | 8/2001 | Melzer et al. | |
| 6,284,971 | B1 | 9/2001 | Atalar et al. | |
| 6,332,089 | B1 | 12/2001 | Acker et al. | |
| 6,370,427 | B1 * | 4/2002 | Alt et al. | 607/4 |
| 6,390,996 | B1 | 5/2002 | Halperin et al. | |
| 6,408,202 | B1 | 6/2002 | Lima et al. | |
| 6,414,835 | B1 | 7/2002 | Wolf et al. | |
| 6,424,234 | B1 | 7/2002 | Stevenson | |
| 6,428,537 | B1 | 8/2002 | Swanson et al. | |
| 6,456,481 | B1 | 9/2002 | Stevenson | |
| 6,459,935 | B1 | 10/2002 | Piersma | |
| 6,473,291 | B1 | 10/2002 | Stevenson | |
| 6,493,591 | B1 | 12/2002 | Stokes | |
| 6,529,103 | B1 | 3/2003 | Brendel et al. | |
| 6,535,766 | B1 | 3/2003 | Thompson et al. | |
| 6,539,253 | B2 | 3/2003 | Thompson et al. | |
| 6,549,800 | B1 | 4/2003 | Atalar et al. | |
| 6,556,009 | B2 | 4/2003 | Kellman et al. | |
| 6,566,978 | B2 | 5/2003 | Stevenson et al. | |
| 6,567,259 | B2 | 5/2003 | Stevenson et al. | |
| 6,567,703 | B1 | 5/2003 | Thompson et al. | |
| 6,593,884 | B1 | 7/2003 | Gilboa et al. | |
| 6,606,513 | B2 | 8/2003 | Lardo et al. | |
| 6,628,980 | B2 | 9/2003 | Atalar et al. | |
| 6,633,780 | B1 | 10/2003 | Berger | |
| 6,643,903 | B2 | 11/2003 | Stevenson et al. | |

| | | | | | | |
|---|---|---|---|---|---|---|
| 6,654,628 B1 | 11/2003 | Silber et al. | | 2005/0201039 A1 | 9/2005 | Stevenson et al. |
| 6,675,033 B1 | 1/2004 | Lardo et al. | | 2005/0219787 A1 | 10/2005 | Stevenson et al. |
| 6,675,779 B2 | 1/2004 | King et al. | | 2005/0247475 A1 | 11/2005 | Stevenson et al. |
| 6,687,550 B1 | 2/2004 | Doan | | 2006/0009819 A1 | 1/2006 | Przybyszewski |
| 6,690,963 B2 | 2/2004 | Ben-Haim et al. | | 2006/0028784 A1 | 2/2006 | Brendel |
| 6,701,176 B1 | 3/2004 | Halperin et al. | | 2006/0085043 A1 | 4/2006 | Stevenson |
| 6,714,809 B2 | 3/2004 | Lee et al. | | 2006/0100506 A1 | 5/2006 | Halperin et al. |
| 6,765,779 B2 | 7/2004 | Stevenson et al. | | 2006/0212096 A1 | 9/2006 | Stevenson |
| 6,765,780 B2 | 7/2004 | Brendel et al. | | 2006/0221543 A1 | 10/2006 | Stevenson et al. |
| 6,771,067 B2 | 8/2004 | Kellman et al. | | 2006/0247684 A1 | 11/2006 | Halperin et al. |
| 6,829,509 B1 | 12/2004 | MacDonald et al. | | 2006/0259093 A1 | 11/2006 | Stevenson et al. |
| 6,847,837 B1 | 1/2005 | Melzer et al. | | 2007/0019362 A1 | 1/2007 | Stevenson et al. |
| 6,868,288 B2 | 3/2005 | Thompson | | 2007/0035910 A1 | 2/2007 | Stevenson |
| 6,876,885 B2 | 4/2005 | Swoyer et al. | | 2007/0088416 A1 | 4/2007 | Atalar et al. |
| 6,882,248 B2 | 4/2005 | Stevenson et al. | | 2007/0112398 A1 | 5/2007 | Stevenson et al. |
| 6,888,715 B2 | 5/2005 | Stevenson et al. | | 2007/0123949 A1 | 5/2007 | Dabney et al. |
| 6,898,454 B2 | 5/2005 | Atalar et al. | | 2007/0279834 A1 | 12/2007 | Stevenson et al. |
| 6,904,307 B2 | 6/2005 | Karmarkar et al. | | 2007/0288058 A1 | 12/2007 | Halperin et al. |
| 6,925,328 B2 | 8/2005 | Foster et al. | | 2008/0049376 A1 | 2/2008 | Stevenson et al. |
| 6,931,286 B2 | 8/2005 | Sigg et al. | | 2008/0058635 A1 | 3/2008 | Halperin et al. |
| 6,949,929 B2 | 9/2005 | Gray et al. | | 2008/0065181 A1 | 3/2008 | Stevenson |
| 6,952,613 B2 | 10/2005 | Swoyer et al. | | 2008/0071313 A1 | 3/2008 | Stevenson et al. |
| 6,971,391 B1 | 12/2005 | Wang et al. | | 2008/0116997 A1 | 5/2008 | Dabney et al. |
| 6,985,347 B2 | 1/2006 | Stevenson et al. | | 2008/0119919 A1 | 5/2008 | Atalar et al. |
| 6,987,660 B2 | 1/2006 | Stevenson et al. | | 2008/0132987 A1 | 6/2008 | Westlund et al. |
| 6,999,818 B2 | 2/2006 | Stevenson et al. | | 2008/0161886 A1 | 7/2008 | Stevenson et al. |
| 7,012,192 B2 | 3/2006 | Stevenson et al. | | 2008/0195180 A1 | 8/2008 | Stevenson et al. |
| 7,013,180 B2 | 3/2006 | Villaseca et al. | | 2008/0269591 A1 | 10/2008 | Halperin et al. |
| 7,035,076 B1 | 4/2006 | Stevenson | | 2009/0116167 A1 | 5/2009 | Stevenson et al. |
| 7,035,077 B2 | 4/2006 | Brendel | | 2009/0163980 A1 | 6/2009 | Stevenson |
| 7,038,900 B2 | 5/2006 | Stevenson et al. | | 2009/0163981 A1 | 6/2009 | Stevenson et al. |
| 7,047,074 B2 | 5/2006 | Connelly et al. | | 2009/0243756 A1 | 10/2009 | Stevenson et al. |
| 7,092,766 B1 | 8/2006 | Salys et al. | | 2009/0259265 A1 | 10/2009 | Stevenson et al. |
| 7,113,387 B2 | 9/2006 | Stevenson et al. | | 2010/0016936 A1 | 1/2010 | Stevenson et al. |
| 7,133,714 B2 | 11/2006 | Karmarkar et al. | | 2010/0023000 A1 | 1/2010 | Stevenson et al. |
| 7,136,273 B2 | 11/2006 | Stevenson et al. | | 2010/0023095 A1 | 1/2010 | Stevenson et al. |
| 7,155,271 B2 | 12/2006 | Halperin et al. | | 2010/0060431 A1 | 3/2010 | Stevenson et al. |
| 7,199,995 B2 | 4/2007 | Stevenson | | 2010/0100164 A1 | 4/2010 | Johnson et al. |
| 7,236,816 B2 | 6/2007 | Kumar et al. | | 2010/0123547 A1 | 5/2010 | Stevenson et al. |
| 7,310,216 B2 | 12/2007 | Stevenson et al. | | 2010/0134951 A1 | 6/2010 | Brendel et al. |
| 7,412,276 B2 | 8/2008 | Halperin et al. | | 2010/0160997 A1 | 6/2010 | Johnson et al. |
| 7,422,568 B2 | 9/2008 | Yang et al. | | 2010/0168821 A1 | 7/2010 | Johnson et al. |
| 7,489,495 B2 | 2/2009 | Stevenson | | 2010/0174349 A1 | 7/2010 | Stevenson et al. |
| 7,535,693 B2 | 5/2009 | Stevenson et al. | | 2010/0185263 A1 | 7/2010 | Stevenson et al. |
| 7,623,335 B2 | 11/2009 | Stevenson et al. | | 2010/0191236 A1 | 7/2010 | Johnson et al. |
| 7,623,336 B2 | 11/2009 | Stevenson et al. | | 2010/0191306 A1 | 7/2010 | Stevenson et al. |
| 7,689,288 B2 | 3/2010 | Stevenson et al. | | 2010/0194541 A1 | 8/2010 | Stevenson et al. |
| 7,702,387 B2 | 4/2010 | Stevenson et al. | | 2010/0198312 A1 | 8/2010 | Stevenson et al. |
| 7,751,903 B2 * | 7/2010 | Stevenson et al. .............. 607/63 | | 2010/0208397 A1 | 8/2010 | Johnson et al. |
| 7,765,005 B2 | 7/2010 | Stevenson | | 2010/0217262 A1 | 8/2010 | Stevenson et al. |
| 7,787,958 B2 | 8/2010 | Stevenson | | 2010/0222856 A1 | 9/2010 | Halperin et al. |
| 7,822,460 B2 | 10/2010 | Halperin et al. | | 2010/0222857 A1 | 9/2010 | Halperin et al. |
| 7,844,319 B2 | 11/2010 | Susil et al. | | 2010/0231327 A1 | 9/2010 | Johnson et al. |
| 7,853,324 B2 | 12/2010 | Stevenson et al. | | 2010/0241206 A1 | 9/2010 | Truex et al. |
| 7,853,325 B2 | 12/2010 | Dabney et al. | | 2010/0280584 A1 | 11/2010 | Johnson et al. |
| 7,899,551 B2 | 3/2011 | Westlund et al. | | 2010/0318160 A1 | 12/2010 | Stevenson |
| 7,916,013 B2 | 3/2011 | Stevenson | | 2010/0321163 A1 | 12/2010 | Stevenson |
| 7,917,218 B2 | 3/2011 | Iyer et al. | | 2010/0324639 A1 | 12/2010 | Stevenson et al. |
| 7,920,916 B2 | 4/2011 | Johnson et al. | | 2010/0324640 A1 | 12/2010 | Bauer et al. |
| 2001/0051787 A1 * | 12/2001 | Haller et al. ................ 604/66 | | 2010/0328049 A1 | 12/2010 | Frysz et al. |
| 2002/0026224 A1 | 2/2002 | Thompson et al. | | 2011/0001610 A1 | 1/2011 | Stevenson et al. |
| 2003/0028094 A1 | 2/2003 | Kumar et al. | | 2011/0004283 A1 | 1/2011 | Stevenson et al. |
| 2003/0028095 A1 | 2/2003 | Tulley et al. | | 2011/0022140 A1 | 1/2011 | Stevenson et al. |
| 2003/0050557 A1 | 3/2003 | Susil et al. | | 2011/0029043 A1 | 2/2011 | Frysz et al. |
| 2003/0179536 A1 | 9/2003 | Stevenson et al. | | 2011/0040343 A1 | 2/2011 | Johnson et al. |
| 2003/0199755 A1 | 10/2003 | Halperin | | 2011/0043297 A1 | 2/2011 | Stevenson et al. |
| 2003/0213604 A1 | 11/2003 | Stevenson et al. | | 2011/0054582 A1 | 3/2011 | Dabney et al. |
| 2003/0213605 A1 | 11/2003 | Brendel et al. | | 2011/0057037 A1 | 3/2011 | Frysz |
| 2004/0015079 A1 | 1/2004 | Berger et al. | | 2011/0066212 A1 | 3/2011 | Stevenson et al. |
| 2004/0024434 A1 | 2/2004 | Yang et al. | | | | |
| 2004/0046557 A1 | 3/2004 | Karmarkar et al. | | FOREIGN PATENT DOCUMENTS | | |
| 2004/0167392 A1 | 8/2004 | Halperin et al. | | EP | 0145430 | 5/1991 |
| 2004/0201947 A1 | 10/2004 | Stevenson et al. | | EP | 0466424 | 1/1992 |
| 2004/0257747 A1 | 12/2004 | Stevenson et al. | | EP | 0557127 | 8/1993 |
| 2004/0263173 A1 | 12/2004 | Gray | | EP | 0673621 | 9/1995 |
| 2004/0263174 A1 | 12/2004 | Gray et al. | | EP | 0498996 | 3/1997 |
| 2005/0007718 A1 | 1/2005 | Stevenson et al. | | EP | 1021730 | 4/2003 |
| 2005/0190527 A1 | 9/2005 | Stevenson et al. | | EP | 0930509 | 3/2004 |
| 2005/0197677 A1 | 9/2005 | Stevenson | | JP | 60141034 | 7/1985 |

| | | | | | |
|---|---|---|---|---|---|
| JP | 61181925 | 8/1986 | WO | 2005114685 | 12/2005 |
| JP | 62233905 | 10/1987 | WO | 2006031317 | 3/2006 |
| JP | 4071536 | 3/1992 | WO | 2007102893 | 9/2007 |
| JP | 6054823 | 3/1994 | WO | 2007117302 | 10/2007 |
| JP | 06070902 | 3/1994 | WO | 2007145671 | 12/2007 |
| JP | 09094238 | 4/1997 | WO | 2010059376 | 5/2010 |
| JP | 11239572 | 9/1999 | WO | 2010081155 | 7/2010 |
| WO | 9740396 | 10/1997 | WO | 2010081167 | 7/2010 |
| WO | 9852461 | 11/1998 | WO | 2010107608 | 9/2010 |
| WO | 9919739 | 4/1999 | WO | 2010107926 | 9/2010 |
| WO | 0010456 | 3/2000 | WO | 2010151366 | 12/2010 |
| WO | 0025672 | 5/2000 | WO | 2011002533 | 1/2011 |
| WO | 02083016 | 10/2002 | WO | 2011037648 | 3/2011 |
| WO | 2004095281 | 11/2004 | | | |

* cited by examiner

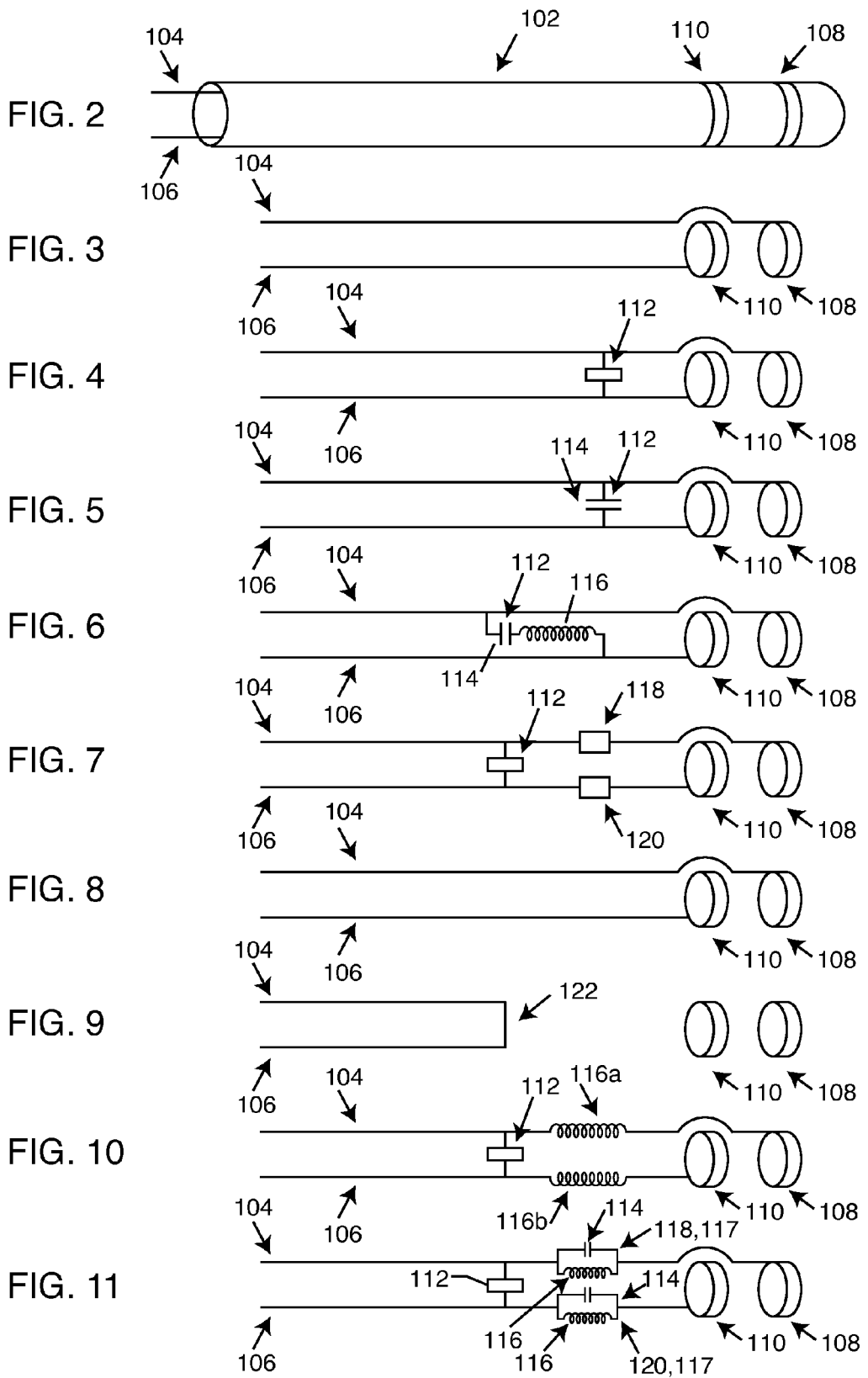

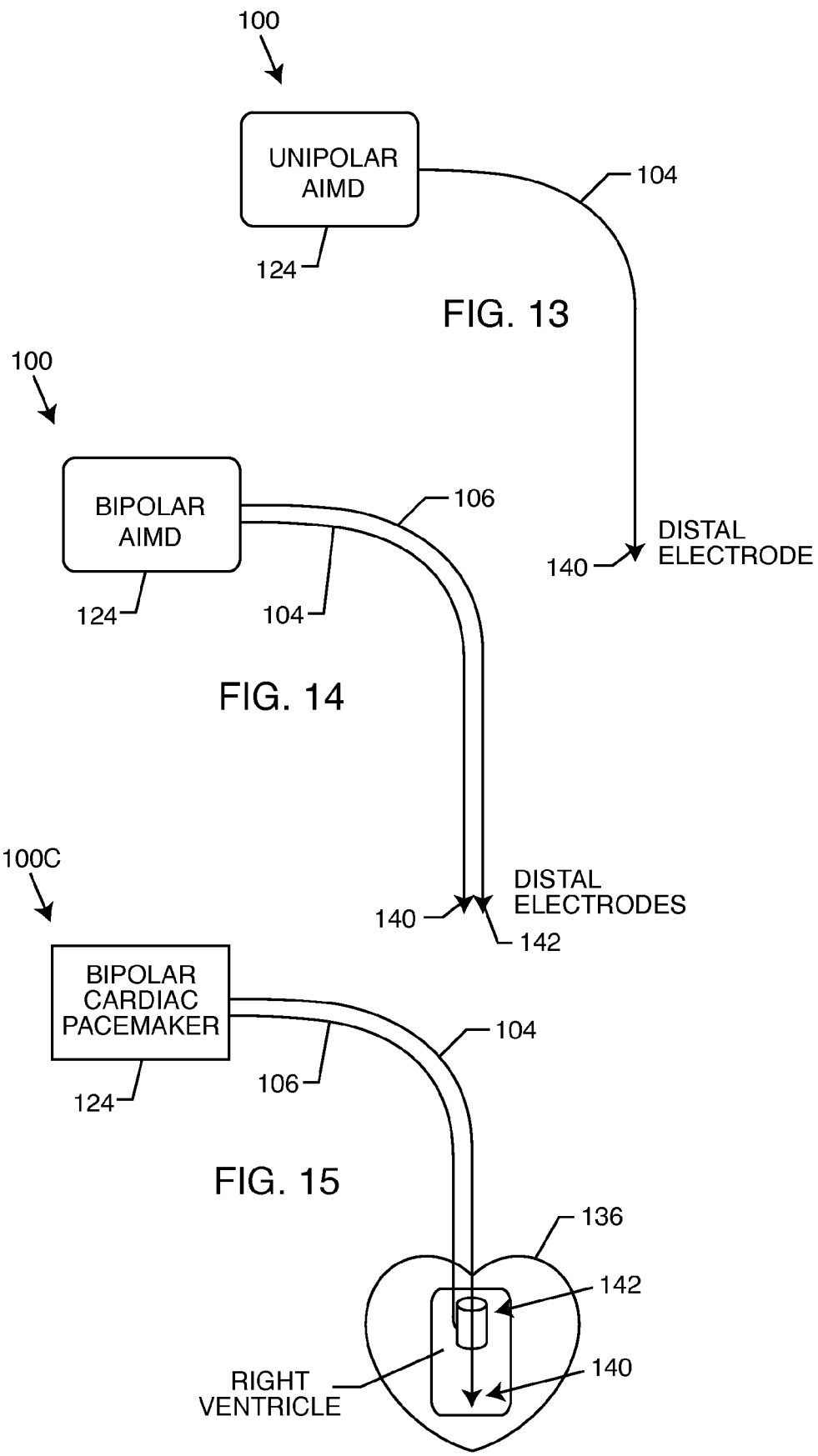

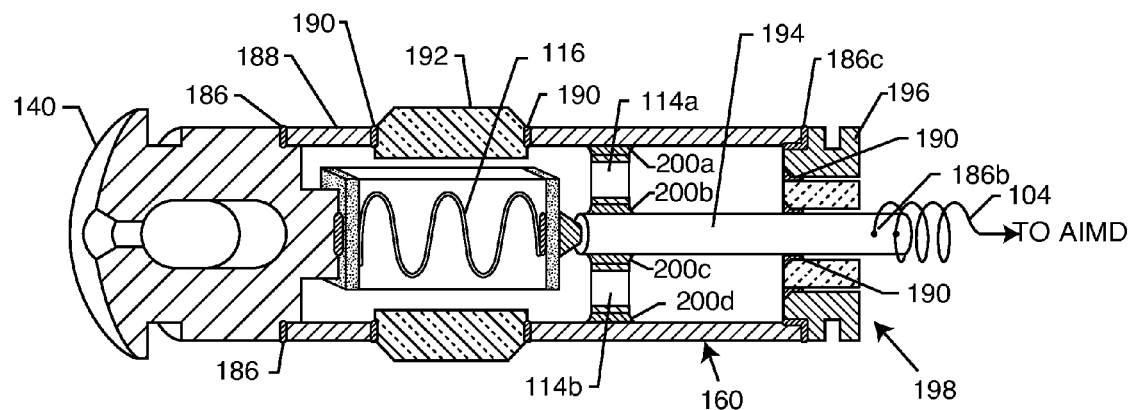
FIG. 30
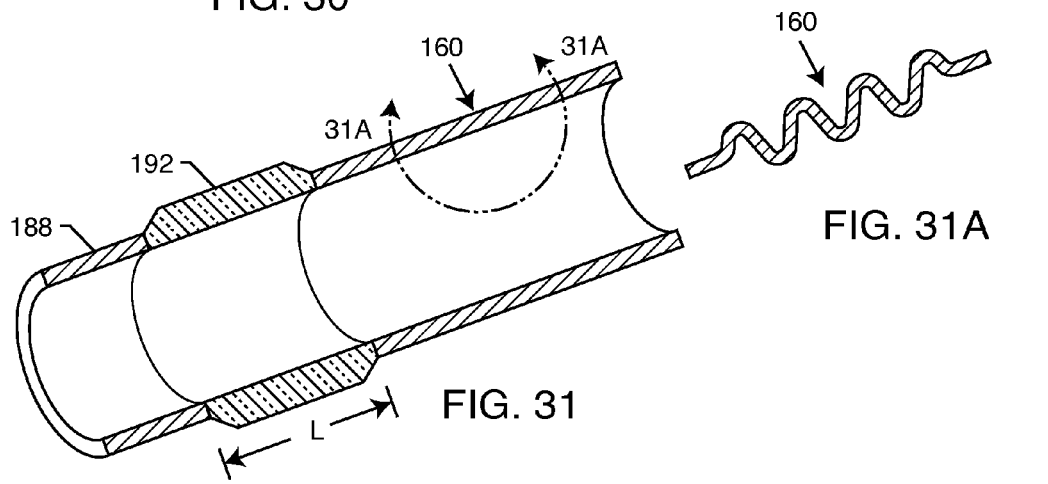
FIG. 31A
FIG. 31
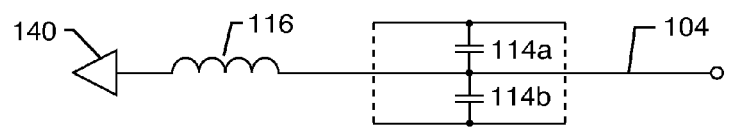
FIG. 32
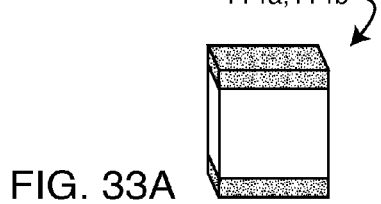
FIG. 33A
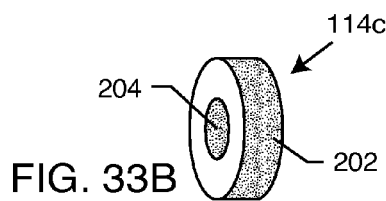
FIG. 33B WHERE   C = CAPACITANCE IN FARADS
        L = INDUCTANCE IN HENRYS
        R = RESISTANCE (INCLUDES RESISTANCE OF
            INDUCTOR, HOOK-UP WIRE & CAPACITOR
            EQUILIVANT SERIES RESISTANCE (ESR)

RESONANT FREQUENCY   = $F_r$

WHERE  $F_R = \dfrac{1}{2\pi\sqrt{LC}}$

WHERE $F_R$ IS IN HERTZ

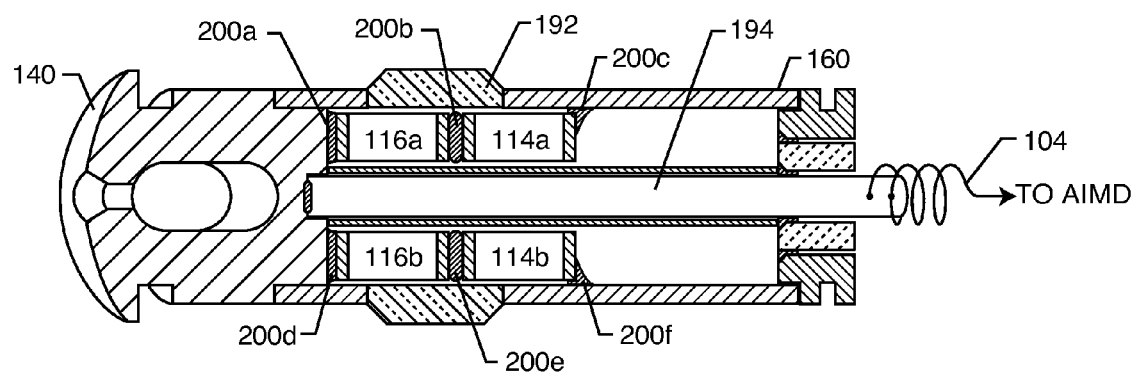
FIG. 41
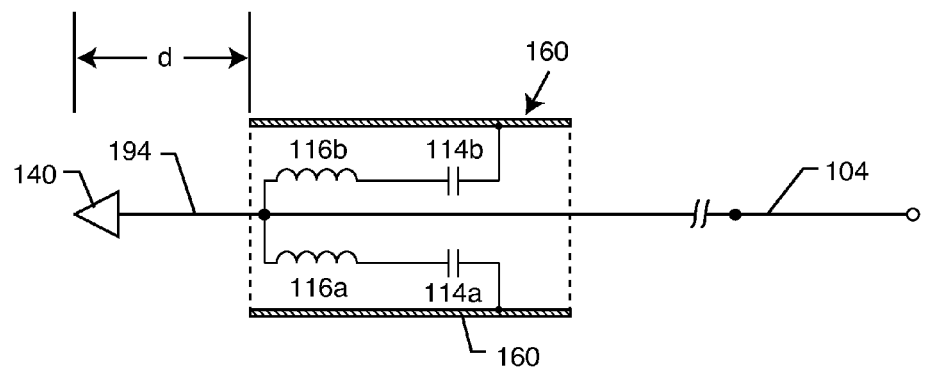
FIG. 42
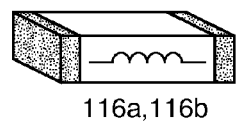 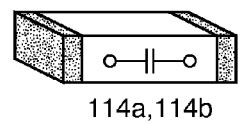
FIG. 43A    FIG. 43B

FREQUENCY SELECTIVE PASSIVE COMPONENT NETWORKS FOR ACTIVE IMPLANTABLE MEDICAL DEVICES UTILIZING AN ENERGY DISSIPATING SURFACE

FIELD OF INVENTION

Currently the application has a parent application Ser. No. 12/489,921 which is now U.S. Pat. No. 7,751,903, and which has a parent application ser. No. 10/123,534 that is now U.S. Pat. No. 7,844,319. This application generally relates to the problem of energy induced into implanted leads during medical diagnostic procedures such as magnetic resonant imaging (MRI). Specifically, the radio frequency (RF) pulsed field of MRI can couple to an implanted lead in such a way that electromagnetic forces (EMFs) are induced in the lead. The amount of energy that is induced is related to a number of complex factors, but in general, is dependent upon the local electric field that is tangent to lead and the integral of the electric field strength along the lead. In certain situations, these EMFs can cause currents to flow into distal electrodes or in the electrode interface with body tissue. It has been documented that when this current becomes excessive, that overheating of said lead or its associated electrode or overheating of the associated interface with body tissue can occur. There have been cases of damage to such body tissue which has resulted in loss of capture of cardiac pace making pulses, tissue damage, severe enough to result in brain damage or multiple amputations, and the like. The present invention relates generally to methods of redirecting said energy to locations other than a distal tip electrode-to-tissue interface. The redirection of this RF energy is generally done by use of frequency selective devices, such as inductors, capacitors and filtered networks. In general, this is accomplished through frequency selective low pass filters or series resonant LC trap filters wherein the RF energy can be redirected to another surface or is converted to heat. These implantable lead systems are generally associated with active implantable medical devices (AIMDs), such as cardiac pacemakers, cardioverter defibrillators, neurostimulators and the like. Implantable leads can also be associated with external devices, such as external pacemakers, externally worn neurostimulators (such as pain control spinal cord stimulators) and the like.

BACKGROUND OF THE INVENTION

Compatibility of cardiac pacemakers, implantable defibrillators and other types of active implantable medical devices with magnetic resonance imaging (MRI) and other types of hospital diagnostic equipment has become a major issue. If one goes to the websites of the major cardiac pacemaker manufacturers in the United States, which include St. Jude Medical, Medtronic and Boston Scientific (formerly Guidant), one will see that the use of MRI is generally contra-indicated with pacemakers and implantable defibrillators. See also:
(1) Safety Aspects of Cardiac Pacemakers in Magnetic Resonance Imaging", a dissertation submitted to the Swiss Federal Institute of Technology Zurich presented by Roger Christoph Luchinger, Zurich 2002;
(2) "1. Dielectric Properties of Biological Tissues: Literature Survey", by C. Gabriel, S. Gabriel and E. Cortout;
(3) "II. Dielectric Properties of Biological Tissues: Measurements and the Frequency Range 0 Hz to 20 GHz", by S. Gabriel, R. W. Lau and C. Gabriel;
(4) "III. Dielectric Properties of Biological Tissues: Parametric Models for the Dielectric Spectrum of Tissues", by S. Gabriel, R. W. Lau and C. Gabriel; and
(5) "Advanced Engineering Electromagnetics, C. A. Balanis, Wiley, 1989;
(6) Systems and Methods for Magnetic-Resonance-Guided Interventional Procedures, Patent Application Publication US 2003/0050557, Susil and Halperin et. al, published Mar. 13, 2003;
(7) Multifunctional Interventional Devices for MRI: A Combined Electrophysiology/MRI Catheter, by, Robert C. Susil, Henry R. Halperin, Christopher J. Yeung, Albert C. Lardo and Ergin Atalar, MRI in Medicine, 2002; and
(8) Multifunctional Interventional Devices for Use in MRI, U.S. Patent Application Ser. No. 60/283,725, filed Apr. 13, 2001.

The contents of the foregoing are all incorporated herein by reference.

However, an extensive review of the literature indicates that MRI is indeed often used with pacemaker, neurostimulator and other active implantable medical device (AIMD) patients. The safety and feasibility of MRI in patients with cardiac pacemakers is an issue of gaining significance. The effects of MRI on patients' pacemaker systems have only been analyzed retrospectively in some case reports. There are a number of papers that indicate that MRI on new generation pacemakers can be conducted up to 0.5 Tesla (T). MRI is one of medicine's most valuable diagnostic tools. MRI is, of course, extensively used for imaging, but is also used for interventional medicine (surgery). In addition, MRI is used in real time to guide ablation catheters, neurostimulator tips, deep brain probes and the like. An absolute contra-indication for pacemaker or neurostimulator patients means that these patients are excluded from MRI. This is particularly true of scans of the thorax and abdominal areas. Because of MRI's incredible value as a diagnostic tool for imaging organs and other body tissues, many physicians simply take the risk and go ahead and perform MRI on a pacemaker patient. The literature indicates a number of precautions that physicians should take in this case, including limiting the power of the MRI RF Pulsed field (Specific Absorption Rate—SAR level), programming the pacemaker to fixed or asynchronous pacing mode, and then careful reprogramming and evaluation of the pacemaker and patient after the procedure is complete. There have been reports of latent problems with cardiac pacemakers or other AIMDs after an MRI procedure sometimes occurring many days later. Moreover, there are a number of recent papers that indicate that the SAR level is not entirely predictive of the heating that would be found in implanted leads or devices. For example, for magnetic resonance imaging devices operating at the same magnetic field strength and also at the same SAR level, considerable variations have been found relative to heating of implanted leads. It is speculated that SAR level alone is not a good predictor of whether or not an implanted device or its associated lead system will overheat.

There are three types of electromagnetic fields used in an MRI unit. The first type is the main static magnetic field designated $B_0$ which is used to align protons in body tissue. The field strength varies from 0.5 to 3.0 Tesla in most of the currently available MRI units in clinical use. Some of the newer MRI system fields can go as high as 4 to 5 Tesla. At the recent International Society for Magnetic Resonance in Medicine (ISMRM), which was held on 5-6 Nov. 2005, it was reported that certain research systems are going up as high as 11.7 Tesla and will be ready sometime in 2010. This is over 100,000 times the magnetic field strength of the earth. A static magnetic field can induce powerful mechanical forces and torque on any magnetic materials implanted within the patient. This would include certain components within the cardiac pacemaker itself and/or lead systems. It is not likely (other than sudden system shut down) that the static MRI magnetic field can induce currents into the pacemaker lead system and hence into the pacemaker itself. It is a basic principle of physics that a magnetic field must either be time-varying as it cuts across the conductor, or the conductor itself must move within a specifically varying magnetic field for currents to be induced.

The second type of field produced by magnetic resonance imaging is the pulsed RF field which is generated by the body coil or head coil. This is used to change the energy state of the protons and elicit MRI signals from tissue. The RF field is homogeneous in the central region and has two main components: (1) the electric field is circularly polarized in the actual plane; and (2) the H field, sometimes generally referred to as the net magnetic field in matter, is related to the electric field by Maxwell's equations and is relatively uniform. In general, the RF field is switched on and off during measurements and usually has a frequency of 21 MHz to 64 MHz to 128 MHz depending upon the static magnetic field strength. The frequency of the RF pulse for hydrogen scans varies by the Lamor equation with the field strength of the main static field where: RF PULSED FREQUENCY in MHz=(42.56) (STATIC FIELD STRENGTH IN TESLA). There are also phosphorous and other types of scanners wherein the Lamor equation would be different. The present invention applies to all such scanners.

The third type of electromagnetic field is the time-varying magnetic gradient fields designated $B_X$, $B_Y$, $B_Z$, which are used for spatial localization. These change their strength along different orientations and operating frequencies on the order of 1 kHz. The vectors of the magnetic field gradients in the X, Y and Z directions are produced by three sets of orthogonally positioned coils and are switched on only during the measurements. In some cases, the gradient field has been shown to elevate natural heart rhythms (heart beat). This is not completely understood, but it is a repeatable phenomenon. The gradient field is not considered by many researchers to create any other adverse effects.

It is instructive to note how voltages and electro-magnetic interference (EMI) are induced into an implanted lead system. At very low frequency (VLF), voltages are induced at the input to the cardiac pacemaker as currents circulate throughout the patient's body and create voltage drops. Because of the vector displacement between the pacemaker housing and, for example, the tip electrode, voltage drop across the resistance of body tissues may be sensed due to Ohms Law and the circulating current of the RF signal. At higher frequencies, the implanted lead systems actually act as antennas where voltages (EMFs) are induced along their length. These antennas are not very efficient due to the damping effects of body tissue; however, this can often be offset by extremely high power fields (such as MRI pulsed fields) and/or body resonances. At very high frequencies (such as cellular telephone frequencies), EMI signals are induced only into the first area of the leadwire system (for example, at the header block of a cardiac pacemaker). This has to do with the wavelength of the signals involved and where they couple efficiently into the system.

Magnetic field coupling into an implanted lead system is based on loop areas. For example, in a cardiac pacemaker unipolar lead, there is a loop formed by the lead as it comes from the cardiac pacemaker housing to its distal tip electrode, for example, located in the right ventricle. The return path is through body fluid and tissue generally straight from the tip electrode in the right ventricle back up to the pacemaker case or housing. This forms an enclosed area which can be measured from patient X-rays in square centimeters. The average loop area is 200 to 225 square centimeters. This is an average and is subject to great statistical variation. For example, in a large adult patient with an abdominal pacemaker implant, the implanted loop area is much larger (around 400 square centimeters).

Relating now to the specific case of MRI, the magnetic gradient fields would be induced through enclosed loop areas. However, the pulsed RF fields, which are generated by the body coil, would be primarily induced into the lead system by antenna action. Subjected to RF frequencies, the lead itself can exhibit complex transmission line behavior.

At the frequencies of interest in MRI, RF energy can be absorbed and converted to heat. The power deposited by RF pulses during MRI is complex and is dependent upon the power (Specific Absorption Rate (SAR) Level) and duration of the RF pulse, the transmitted frequency, the number of RF pulses applied per unit time, and the type of configuration of the RF transmitter coil used. The amount of heating also depends upon the volume of tissue imaged, the electrical resistivity of tissue and the configuration of the anatomical region imaged. There are also a number of other variables that depend on the placement in the human body of the AIMD and the length and trajectory of its associated lead(s). For example, it will make a difference how much EMF is induced into a pacemaker lead system as to whether it is a left or right pectoral implant. In addition, the routing of the lead and the lead length are also very critical as to the amount of induced current and heating that would occur. Also, distal tip design is very important as it can heat up due to MRI RF induced energy. The cause of heating in an MRI environment is two-fold: (a) RF field coupling to the lead can occur which induces significant local heating; and (b) currents induced between the distal tip and tissue during MRI RF pulse transmission sequences can cause local Ohms Law (resistive) heating in tissue next to the distal tip electrode of the implanted lead. The RF field of an MRI scanner can produce enough energy to induce RF voltages in an implanted lead and resulting currents sufficient to damage some of the adjacent myocardial tissue. Tissue ablation (destruction resulting in scars) has also been observed. The effects of this heating are not readily detectable by monitoring during the MRI. Indications that heating has occurred would include an increase in pacing threshold, venous ablation, Larynx or esophageal ablation, myocardial perforation and lead penetration, or even arrhythmias caused by scar tissue. Such long term heating effects of MRI have not been well studied yet for all types of AIMD lead geometries. There can also be localized heating problems associated with various types of electrodes in addition to tip electrodes. This includes ring electrodes or pad electrodes. Ring electrodes are commonly used with a wide variety of implanted devices including cardiac pacemakers, and neurostimulators, and the like. Pad electrodes are very common in neurostimulator applications. For example, spinal cord stimulators or deep brain stimulators can include a plurality of pad electrodes to make contact with nerve tissue. A good example of this also occurs in a cochlear implant. In a typical cochlear implant there would be sixteen pad electrodes placed up into the cochlea. Several of these pad electrodes make contact with auditory nerves. Although there are a number of studies that have shown that MRI patients with active implantable medical devices, such as cardiac pacemakers, can be at risk for potential hazardous effects, there are a number of reports in the literature that MRI can be safe for imaging of pacemaker patients when a number of precautions are taken (only when an MRI is thought to be an absolute diagnostic necessity). While these anecdotal reports are of interest, they are certainly not scientifically convincing that all MRI can be safe. For example, just variations in the pacemaker lead length and implant trajectory can significantly affect how much heat is generated. A paper entitled, HEATING AROUND INTRAVASCULAR GUIDEWIRES BY RESONATING RF WAVES by Konings, et al., journal of Magnetic Resonance Imaging, Issue 12:79-85 (2000), does an excellent job of explaining how the RF fields from MRI scanners can couple into implanted leads. The paper includes both a theoretical approach and actual temperature measurements. In a worst-case, they measured temperature rises of up to 74 degrees C. after 30 seconds of scanning exposure. The contents of this paper are incorporated herein by reference.

The effect of an MRI system on the function of pacemakers, ICDs, neurostimulators and the like, depends on various factors, including the strength of the static magnetic field, the pulse sequence, the strength of RF field, the anatomic region being imaged, and many other factors. Further complicating this is the fact that each patient's condition and physiology is different and each lead implant has a different length and/or implant trajectory in body tissues. Most experts still conclude that MRI for the pacemaker patient should not be considered safe.

It is well known that many of the undesirable effects in an implanted lead system from MRI and other medical diagnostic procedures are related to undesirable induced EMFs in the lead system and/or RF currents in its distal tip (or ring) electrodes. This can lead to overheating of body tissue at or adjacent to the distal tip.

Distal tip electrodes can be unipolar, bipolar and the like. It is very important that excessive current not flow at the interface between the lead distal tip electrode and body tissue. In a typical cardiac pacemaker, for example, the distal tip electrode can be passive or of a screw-in helix type as will be more fully described. In any event, it is very important that excessive RF current not flow at this junction between the distal tip electrode and for example, myocardial or nerve tissue. Excessive current at the distal electrode to tissue interface can cause excessive heating to the point where tissue ablation or even perforation can occur. This can be life threatening for cardiac patients. For neurostimulator patients, such as deep brain stimulator patients, thermal injury can cause permanent disability or even be life threatening. Similar issues exist for spinal cord stimulator patients, cochlear implant patients and the like.

Accordingly, there is a need for novel RF impeding and/or diverting circuits, which are frequency selective and are constructed of passive components for implantable leads and/or leadwires. The purpose of these circuits is to prevent MRI induced energy from reaching the distal tip electrode or its interface with body tissue. By redirecting said energy to locations at a point distant from the distal electrodes, this minimizes or eliminates hazards associated with overheating of said distal electrodes during diagnostic procedures, such as MRI. For maximum RF energy transfer out of the lead, frequency selective diverter circuits are needed which decouple and transfer energy which is induced onto implanted leads from the MRI pulsed RF field to an energy dissipating surface. The present invention fulfills these needs and provides other related advantages.

SUMMARY OF THE INVENTION

The present invention includes frequency selective impeding and diverting (decoupling) circuits which transfer energy which is induced from the MRI pulsed RF field to an energy dissipating surface (EDS), preferably the housing for an active implantable medical device (AIMD). In this way, RF energy can be shunted harmlessly into the bulk of a probe or catheter, body tissues distant from the distal electrodes, or into flowing blood or other body fluids thereby directing such energy away from a distal tip electrode.

There are three types of electromagnetic fields used in an MRI unit. The first type is the main static magnetic field designated $B_0$ which is used to align protons in body tissue. The field strength varies from 0.5 to 3 Tesla in most of the currently available MRI units in present clinical use. The second electromagnetic field is the pulsed RF field which is given by the Lamor Frequency. The Lamor Frequency formula is 42.56 (static field strength in Tesla)=RF frequency. For example, for a 1.5 Tesla scanner, the frequency of the pulsed RF field is approximately 64 MHz. The third type of field is the gradient field which is used to control where the slice is that generates the image is located within body tissue.

The present invention is primarily directed to the pulsed RF field although it also has applicability to the gradient field as well. Because of the presence of the powerful static field, non-ferromagnetic components are presently used throughout the present invention. The use of ferromagnetic components is contraindicative because they have a tendency to saturate or change properties in the presence of the main static field.

In a broad sense, the present invention relates to a passive component network for an implantable leadwire of an active implantable medical device (AIMD), comprising: (1) an active implantable medical device (AIMD) having (1) a conductive housing; (2) at least one lead having length extending between and to a proximal end adjacent to the AIMD housing and a tissue-stimulating or biological-sensing electrode at a distal tip end; and (3) a frequency selective energy diversion circuit for diverting high-frequency energy away from the lead to the AIMD housing for dissipation of said high-frequency energy. The high-frequency energy may comprise an MRI frequency or a range of MRI frequencies. Typically the MRI frequency in megahertz is selected from the group of frequencies comprising 42.56 times the static magnetic field strength in Teslas of an MRI scanner.

The frequency selective energy diversion circuit may comprise a low pass filter, including a capacitor, an inductor, a Pi filter, a T filter, an LL filter, or an "n" element filter. The capacitor may comprise parasitic capacitance. Moreover, the frequency selective energy diversion circuit may comprise at least one series resonant L-C trap filter, or a plurality of L-C trap filters which resonate respectively at different MRI frequencies.

An impeding circuit may be associated with the diversion circuit for raising the high-frequency impedance of a lead or a leadwire. The impeding circuit is typically disposed between the diversion circuit and the AIMD electronic circuits. The impeding circuit may comprise an inductor, such as an inductor chip, an inductor wire wound onto a ferromagnetic or a non-ferromagnetic mandrel, or a pair of inductor elements wherein the diversion circuit is coupled between the pair of inductor elements and the AIMD housing. Further, the impeding circuit may comprise a bandstop filter.

The at least one lead may comprise at least a pair of leads each having a length extending between and to a proximal end adjacent to the AIMD housing and a tissue-stimulating or biological-sensing electrode at a distal tip end. The diversion circuit may couple each of the leads to the AIMD housing and/or it may be coupled between said pair of leads.

Preferably, the diversion circuit is disposed within the AIMD housing which serves to protect the diversion and impeding circuits from direct contact with patient body fluids. The active implantable medical device may comprise a deep brain stimulator, or a probe or a catheter wherein the electrode comprises an ablation tip electrode. The AIMD housing may comprise at least a portion of a handle for the probe or the catheter.

Other features and advantages of the present invention will become apparent from the following more detailed description, taken in conjunction with the accompanying drawings which illustrate, by way of example, the principles of the invention.

BRIEF DESCRIPTION OF THE DRAWINGS

The accompanying drawings illustrate the invention. In such drawings:

FIG. 2 is a diagrammatic view of a typical probe or catheter;

FIG. 3 is an electrical diagrammatic view of the interior of the prober or catheter of FIG. 2;

FIG. 4 is an electrical diagrammatic view of the structure shown in FIG. 3, with a general impedance element connected between leads;

FIG. 5 is an electrical diagrammatic view similar to FIG. 4, illustrating a capacitor representing a frequency dependent reactive element between the leads;

FIG. 6 is a view similar to FIG. 5, wherein the general reactance element has been replaced by a capacitor in series with an inductor;

FIG. 7 is a view similar to FIGS. 4-6, showing the addition of series frequency selective reactances;

FIG. 8 is similar to FIG. 3, showing a low frequency model of the catheter and associated leads described in FIG. 2;

FIG. 9 is a view similar to FIGS. 3-8, illustrating how the distal rings are electrically isolated at a high frequency;

FIG. 10 is a view similar to FIGS. 3-9, showing the addition of series inductor components added to the frequency selective elements 20;

FIG. 11 is similar to FIGS. 3-10, illustrating frequency selective elements which incorporate parallel resonant inductor and capacitor bandstop filters;

FIG. 13 is a diagram of a unipolar active implantable medical device;

FIG. 14 is a diagram similar to FIG. 13, illustrating a bipolar AIMD system;

FIG. 15 is a diagram similar to FIGS. 13 and 14, illustrating a bipolar lead system with a distal tip and ring electrodes, typically used in a cardiac pacemaker;

FIG. 30 is a sectional view of an hermetically sealed electrode assembly designed for contact with body fluid;

FIG. 31 is a perspective sectional view of a housing portion of the sealed electrode assembly of FIG. 30;

FIG. 31A is an enlarged sectional view corresponding generally with the encircled region 31A-31A of FIG. 31, and illustrating the principle of increasing the surface area of the energy dissipating surface;

FIG. 32 is a schematic circuit diagram corresponding with the sealed electrode assembly of FIG. 30;

FIG. 33A is a perspective view of an exemplary monolithic capacitor for use in the circuit of FIG. 32;

FIG. 33B is a perspective view of an exemplary unipolar feedthrough capacitor for use in the circuit of FIG. 32;

FIG. 41 is a sectional view similar to FIGS. 30, 34 and 35, but shows still another alternative embodiment of the invention for decoupling RF signals from an electrode leadwire;

FIG. 42 is a schematic circuit diagram corresponding with the sealed electrode assembly of FIG. 41;

FIG. 43A illustrates a typical chip inductor for use in the sealed electrode assembly of FIG. 41;

FIG. 43B illustrates a typical chip capacitor for use in the sealed electrode assembly of FIG. 41;

FIG. 59 is an enlarged, fragmented sectional view taken along the line 59-59 from FIG. 58, illustrating a roughened surface formed through, for example, plasma or chemical etching, or the like;

DETAILED DESCRIPTION OF THE PREFERRED EMBODIMENTS

Figure 1:
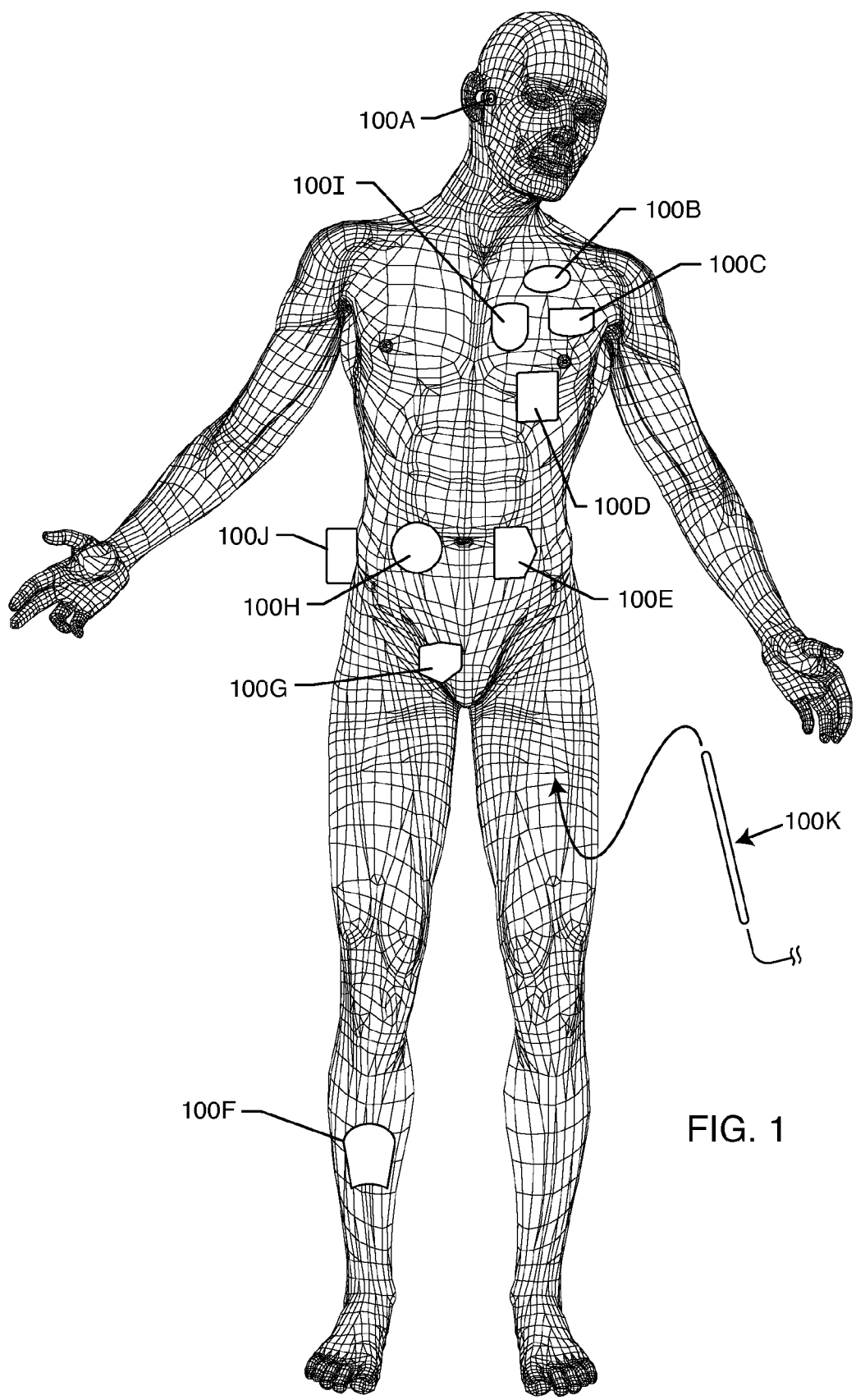
FIG. 1 is a wire-formed diagram of a generic human body showing a number of exemplary implanted medical devices.

FIG. 1 illustrates various types of active implantable medical devices referred to generally by the reference numeral 100 that are currently in use. FIG. 1 is a wire formed diagram of a generic human body showing a number of exemplary implanted medical devices. 100A is a family of implantable hearing devices which can include the group of cochlear implants, piezoelectric sound bridge transducers and the like. 100B includes an entire variety of neurostimulators and brain stimulators. Neurostimulators are used to stimulate the Vagus nerve, for example, to treat epilepsy, obesity and depression. Brain stimulators are similar to a pacemaker-like device and include electrodes implanted deep into the brain for sensing the onset of the seizure and also providing electrical stimulation to brain tissue to prevent the seizure from actually happening. 100C shows a cardiac pacemaker which is well-known in the art. 100D includes the family of left ventricular assist devices (LVAD's), and artificial hearts, including the recently introduced artificial heart known as the Abiocor. 100E includes an entire family of drug pumps which can be used for dispensing of insulin, chemotherapy drugs, pain medications and the like. Insulin pumps are evolving from passive devices to ones that have sensors and closed loop systems. That is, real time monitoring of blood sugar levels will occur. These devices tend to be more sensitive to EMI than passive pumps that have no sense circuitry or externally implanted leadwires. 100F includes a variety of implantable bone growth stimulators for rapid healing of fractures. 100G includes urinary incontinence devices. 100H includes the family of pain relief spinal cord stimulators and anti-tremor stimulators. 100H also includes an entire family of other types of neurostimulators used to block pain. 100I includes a family of implantable cardioverter defibrillator (ICD) devices and also includes the family of congestive heart failure devices (CHF). This is also known in the art as cardio resynchronization therapy devices, otherwise known as CRT devices. 100J illustrates an externally worn pack. This pack could be an external insulin pump, an external drug pump, an external neurostimulator or even a ventricular assist device. 100K illustrates the insertion of an external probe or catheter. These probes can be inserted into the femoral artery, for example, or in any other number of locations in the human body.

Referring to U.S. 2003/0050557, Paragraphs 79 through 82, the contents of which are incorporated herein, metallic structures, particularly leads, are described that when placed in MRI scanners, can pick up high electrical fields which results in local tissue heating. This heating tends to be most concentrated at the ends of the electrical structure (either at the proximal or distal lead ends). This safety issue can be addressed using the disclosed systems and methods of the present invention. A significant concern is that the distal electrodes, which are in contact with body tissue, can cause local tissue burns.

As used herein, the lead means an implanted lead, including its electrodes that are in contact with body tissue. In general, for an AIMD, the term lead means the lead that is outside of the abandoned lead cap housing and is implanted or directed into body tissues. The term leadwire as used herein refers to the wiring that is generally inside of the active implantable medical device (AIMD).

Reference is made to U.S. Publication No. 2003/0050557 drawing, FIGS. 1A through 1G. These figures have been redrawn herein as FIGS. 2 through 11 and are described as follows in light of the present invention.

FIG. 2 is a diagrammatic view of a typical prior art device 102 such as a probe or catheter or AIMD lead distal electrode. There are two leads 104 and 106 which thread through the center of the illustrative probe or catheter and terminate respectively in a corresponding pair of distal conductive electrode rings 108 and 110. Leads 104 and 106 are electrically insulated from each other and also electrically insulated from any metallic structures located within the catheter or lead body. The overall catheter or implanted lead body is generally flexible and is made of biocompatible materials, which also have specific thermal properties. In addition to flexibility, probes and catheters are typically steerable. It is well known that a push-pull wire (not shown in FIG. 2) can be run down the center of the catheter or probe in a lumen and then be attached to a catheter handle or pistol grip or other device so that the physician can carefully steer or thread the probe or catheter through the torturous path of the venous system, even into the ventricles of the heart. Such probes and catheters, for example, can be used for electrical mapping inside of a heart chamber, or for application of RF energy for ablation, which is used to treat certain cardiac arrhythmias. Probes and catheters have wide application to a variety of other medical applications. There are also combined catheters that can do electrical mapping and can also perform RF ablation. When the physician finds the area of arrhythmic electrical activity and wishes to ablate, he activates a switch which applies RF energy to the tip of the catheter (see, e.g., FIG. 55, which will be discussed herein in more detail). This would involve a third electrode right at the catheter tip of FIG. 2 (not shown). It would be extremely valuable if the catheter could be guided during real-time MRI imaging. This is important because of MRI's incredible ability to image soft tissue. In addition, when one is doing deliberate ablation, for example, around a pulmonary vein, it is important that a full circle of scar tissue be formed, for example, to stop atrial fibrillation. MRI has the ability to image the scar as it is being formed (for example, see U.S. Pat. No. 7,155,271). However, it would be highly undesirable if the MRI RF energy that is coupled to the leadwires caused the distal ablation tip or the electrode rings to overheat at an improper time, which could burn or ablate healthy tissues.

FIG. 3 shows the interior taken from FIG. 2 showing leads 104 and 106 which are routed to the two distal electrodes 108 and 110 as previously described in FIG. 2.

FIG. 4 shows the electrical circuit of FIG. 3 with a general frequency selective reactive diverting element 112 connected between leads 104 and 106. In the present invention, the diverting element 112 can consist of a number of frequency selective elements as will be further described. In general, the first conductive lead 104 is electrically coupled to the first electrode 108, the second conductive lead 106 is electrically coupled to the second electrode 110, and the frequency dependent reactive diverting element 112 electrically couples the first and second leads 104 and 106 such that high frequency energy is conducted between the first lead 104 and the second lead 106.

Referring once again to FIG. 4, the frequency selective reactive diverting element 112 tends to be electrically invisible (i.e., a very high impedance) at selected frequencies. The reactive element is desirably selective such that it would not attenuate, for example, low frequency biological signals or RF ablation pulses. However, for high frequency MRI RF pulsed frequencies (such as 64 MHz), this frequency reactive diverting element 112 would look more like a short circuit. This would have the effect of sending the energy induced into the leads 104 and 106 by the MRI RF field back into the catheter body and energy dissipating surface into which the leads are embedded. In other words, there are desirably both RF energy and thermal conductivity to the probe or catheter body or sheath or shield which becomes an energy dissipating surface all along the lengths of leads 104 and 106 such that MRI induced energy that is present in these leads is diverted and converted to heat into the interior and along the catheter body itself. This prevents the heat build up at the extremely sensitive locations right at the ring electrodes 108 and 110 which are in intimate and direct contact with body tissue. In addition, the amount of temperature rise is very small (just a few degrees) because of the energy being dissipated over such a relatively high surface area. As previously mentioned, the high frequency RF pulsed energy from an MRI system can couple to implanted leads. This creates electromagnetic forces (EMFs) which can result in current flowing through the interface between electrodes that are in contact with body tissue. If this current reaches sufficient amplitude, body tissue could be damaged by excessive RF current flow or heat buildup. This can create scar tissue formation, tissue damage or even tissue necrosis such to the point where the AIMD can no longer deliver appropriate therapy. In certain situations, this can be life threatening for the patient.

FIG. 5 shows a capacitor 114 which represents one form of the frequency selective diverting reactive element 112 previously described in FIG. 4. In this case, the reactive element comprises a simple capacitor 114 connected between the first conductor or lead 104 and the second conductor or lead 110 and will have a variable impedance vs. frequency. The following formula is well known in the art: $X_C=1/(2\pi fc)$. Referring to the foregoing equation, one can see that since frequency (f) is in the denominator, as the frequency increases, the capacitive reactance in ohms decreases. With a large number in the denominator, such as the RF pulsed frequency of a 1.5 Tesla MRI system, which is 64 MHz, the capacitive reactance drops to a very low number (essentially a short circuit). By shorting the leads together at this one frequency, this diverts and prevents the RF energy from reaching the distal ring electrodes 108 and 110 and being undesirably dissipated as heat into body tissue. Referring once again to FIG. 4, one can see that the frequency selective diverting element 112 thereby diverts the high frequency RF energy back into the leads 104 and 106. By spreading this energy along the length of leads 104 and 106, it is converted to heat, which is dissipated into the main body of the probe, catheter or energy dissipating sheath. In this way, the relatively large thermal mass of the probe or catheter becomes an energy dissipating surface and any temperature rise is just a few degrees C. In general, a few degrees of temperature rise is not harmful to body tissue. In order to cause permanent damage to body tissue, such as an ablation scar, it generally requires temperatures above 20° C. In summary, the frequency selective reactive element 112, which may comprise a capacitor 114 as shown in FIG. 5, forms a diversion circuit such that high frequency energy is diverted away from the distal electrodes 108 and 110 along the leads 104 and 106 to a surface that is distant from the electrodes 108 and 110, at which point the energy is converted to heat.

FIG. 6 describes a different way of diverting high frequency energy away from the electrodes 108, 110 and accomplishing the same objective. The general diverting reactance element 112 described in FIG. 4 is shown in FIG. 6 to comprise a capacitor 114 in series with an inductor 116 to form an L-C trap circuit. For the L-C trap, there is a particular frequency ($f_r$) at which the capacitive reactance $X_C$ and the inductive reactance $X_L$ are vectorally equal and opposite and tend to cancel each other out. If there are no losses in such a system, this results in a perfect short circuit between leads 104 and 106 at the resonant frequency. The frequency of resonance of the trap filter is given by the equation $$f_r = \frac{1}{2\pi\sqrt{LC}},$$

wherein $f_r$ is the frequency of resonance in Hertz, L is the inductance in henries, and C is the capacitance in farads.

FIG. 7 illustrates any of the aforementioned frequency dependent diverting impedance elements 112 with the addition of series frequency selective impeding reactances 118 and 120. The addition of series impedance further impedes or blocks the flow of high frequency MRI induced currents to the ring electrodes 108 and 110 as will be more fully described in the following drawings.

FIG. 8 is the low frequency model of FIG. 4, 5 or 6. In this regard, FIG. 8 is identical to FIG. 3, in that, once again it shows the electrical leads 104 and 106 connected to the distal ring electrodes 108 and 110 of the probe or catheter 102. In the low frequency model, the frequency reactive diverting impedance elements 112 disappear because at low frequency their impedances approach infinity. Of course, elongated leads in a probe or catheter are electrically and functionally equivalent to leads used for cardiac pacemakers, implantable cardioverter defibrillators, neurostimulators and the like. For example, reference is made to U.S. Pat. No. 7,363,090, the contents of which are incorporated herein. Accordingly, any discussion herein related to probes or catheters apply equally to leads for all active implantable medical devices as described in FIG. 1, and vice versa. Referring once again to FIG. 8, this is also the low frequency model of the circuits shown in FIG. 7. At low frequency, the frequency selective or reactive diverting component 112 tends to look like a very high or infinite impedance. At low frequency, the series reactive or frequency variable impeding elements 118 and 120 tend to look like a very low impedance or short circuit. Accordingly, they all tend to disappear as shown in FIG. 8.

FIG. 9 is a high frequency model that illustrates how the distal electrodes or rings 108 and 110 are electrically isolated at high frequency by shorting leads 104 and 106 at location 122. As previously mentioned, such shorting or current diverting could be accomplished by a direct short, a capacitor, a capacitive low pass filter or a series resonant L-C trap circuit. FIG. 9 also shows the electrodes 108 and 110 as cut or disconnected and electrically isolated from the rest of the circuit. This is because, at very high frequency, series impeding elements 118 and 120 tend to look like a very high impedance or an open circuit. In summary, by reactive elements 112, 118 and 120 acting cooperatively, reactive element 112 diverts the high frequency energy back into energy dissipating surfaces in the probe or catheter while at the same time reactive elements 118 and 120 impede the high frequency RF energy. Accordingly, in the ideal case, at high frequencies, the equivalent circuit of FIG. 9 is achieved. Accordingly, excessive high frequency MRI RF energy cannot reach the distal ring electrodes 108, 110 and cause undesirable heating at that critical tissue interface location.

FIG. 10 shows any of the previously described diverting frequency selective impedance elements 112 in combination with series reactance components 116a and 116b shown in the form of a pair of inductors. It is well known to electrical engineers that the inductive reactance in ohms is given by the equation $X_L=2\pi fL$. In this case the frequency term (f) is in the numerator. Accordingly, as the frequency increases, the reactance (ohms) of the inductors also increases. When the frequency is very high (such as 64 MHz) then the reactance in ohms becomes extremely high (ideally approaches infinity and cuts off the electrodes). By having a short circuit or very low impedance between the leads 104 and 106, and the probe/catheter body and then, at the same time, having a very high impedance in series with the electrodes from inductors 116a and 116b, this provides a very high degree of attenuation to MRI RF pulsed frequencies thereby preventing such energy from reaching the distal ring electrodes 108 and 110. In FIG. 10, the line-to-line selective impedance element 112 diverts high frequency energy back into leads 104 and 106 while at the same time the series inductors 116a and 116b impede (or cut-off) high frequency energy. When the line-to-line element 112 is a capacitor 114 as shown in FIG. 5, then this forms what is known in the prior art as an L section low pass filter, wherein the capacitor 114 electrically cooperates with the inductors 116a and 116b (FIG. 10) to form a 2-element low pass filter. By definition, a low pass filter allows low frequencies such as biological signals to pass to and from the distal electrodes through freely without attenuation while at the same time provides a high degree of attenuation to undesirable high frequency energy. It will be obvious to those skilled in the art that FIG. 5 describes a single element (capacitor) low pass filter, and that FIG. 10 describes a 2-element or L-section low pass filter. Moreover, any number of inductor and capacitor combinations can be used for low pass filters, including 3-element Pi or T circuits, LL, 5-element or even "n" element filters.

FIG. 11 offers an even greater performance improvement over that previously described in FIG. 10. In FIG. 11, modified frequency selective impeding elements 118 and 120 each incorporate a parallel resonant inductor 116 and capacitor 114 which is also known in the industry as a bandstop filter. The L-C components for each of the reactive elements 118 and 120 are carefully chosen such that each of the bandstop filters 118 and 120 is resonant, for example, at the pulsed resonant frequency of an MRI scanner. For common hydrogen scanners, the pulsed resonant frequency of an MR scanner is given by the Lamor equation wherein the RF pulsed frequency in megahertz is equal to 42.56 times the static field strength. For example, for a popular 1.5 Tesla scanner, the RF pulsed frequency is 64 MHz. Common MR scanners that are either in use or in development today along with their RF pulsed frequencies include: 0.5 Tesla-21 MHz; 1.5 Tesla-64 MHz; 3 Tesla-128 MHz; 4 Tesla-170 MHz; 5 Tesla-213 MHz; 7 Tesla-300 MHz; 8 Tesla-340 MHz; and 9.4 Tesla-400 MHz. When the bandstop filters 117, shown as reactive elements 118 and 120, are resonant at any one of these RF pulsed frequencies, then these elements tend to look like an open circuit which impedes the flow of RF current to distal electrodes. When compatibility with different types of MR scanners is required, for example, 1.5, 3 and 5 Tesla, then three separate bandstop filter elements in series may comprise the reactive element 118 (FIG. 7), and three separate bandstop filter elements in series may comprise the reactive element 120 (FIG. 7). Each of these would have their L and C components carefully selected so that they would be resonant at different frequencies. For example, in the case of MR scanners operating at 1.5, 3 and 5 Tesla, the three bandstop filters comprising the reactive element as well as the three bandstop filters comprising the reactive element would be resonant respectively at 64 MHz, at 128 MHz, and at 170 MHz. The resonant frequencies of the bandstop filter elements 117 could also be selected such that they are resonant at the operating frequency of other emitters that the patient may encounter such as diathermy and the like. The use of bandstop filters is more thoroughly described in U.S. Pat. No. 7,363, 090 and Patent Publication Nos. US 2007/0112398 A1; US 2007/0288058; US 2008/0071313 A1; US 2008/0049376 A1; US 2008/0161886 A1; US 2008/0132987 A1 and US 2008/0116997 A1, the contents of which are incorporated herein.

Figure 12:
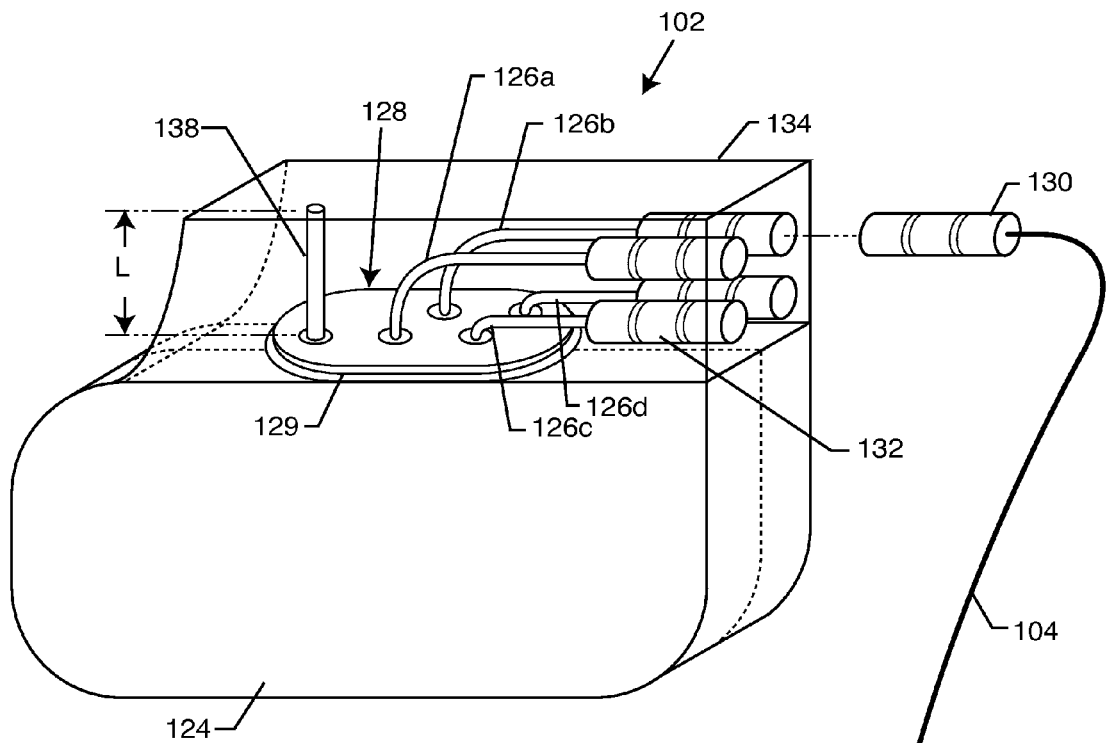
FIG. 12 is a perspective and somewhat schematic view of a prior art active implantable medical device (AIMD) including a leadwire directed to the heart of a patient.

Referring now to FIG. 12, a prior art active implantable medical device (AIMD) 102 is illustrated. In general, the AIMD 102 could, for example, be a cardiac pacemaker (100C in FIG. 1) which is enclosed by a titanium or stainless steel conductive housing 124 as indicated. The conductive housing 124 is hermetically sealed and contains a battery and electronic circuits, however, there is a point where conductors such as the illustrative conductors 126a, 126b, 126c and 126d must ingress and egress in non-conductive relationship relative to the housing 124. This is accomplished by providing a hermetic terminal assembly 128. Hermetic terminal assemblies are well known and generally consist of a ferrule 129 which is laser welded to the titanium housing 124 of the AIMD 102. In FIG. 12, four conductors 126a-126d are shown for connection to a corresponding number of leads, such as the illustrative leadwire 104 shown for coupling to the conductor 126b. In this configuration, the four leads coupled respectively to the conductors 126a-126d comprise a typical dual chamber bipolar cardiac pacemaker.

Connectors 130 commonly known as IS-1 connectors and are designed to plug into mating receptacles 132 on a header block 134 on the pacemaker housing 124. These are low voltage (pacemaker) lead connectors covered by an International Standards Organization (ISO) standard IS-1. Higher voltage devices, such as implantable cardioverter defibrillators, are covered by a standard known as the ISO DF-1. A newer standard had been published that integrates both high voltage and low voltage connectors into a new miniature quadpolar connector series known as the ISO IS-4 standard. Leads plugged into these connectors are typically routed in a pacemaker or ICD application down into the right ventricle and right atrium of the heart 136. There are also new generation devices that have been introduced to the market that couple leads to the outside of the left ventricle. These are known as biventricular devices and are very effective in cardiac resynchronization therapy (CRT) and treating congestive heart failure (CHF).

In FIG. 12, one can see, for example, the conductors 126a and 126b that could be coupled by leads routed, for example, to distal tip and ring electrodes within the right ventricle of the heart 136. The other pair of conductors 126c and 126d could be coupled by leads routed to distal tip and ring electrodes within the right atrium of the heart 136. There is also an RF telemetry pin antenna 138 which is not connected to the IS-1 or DS-1 connector block. This acts as a short stub antenna for picking up telemetry signals that are transmitted from the outside of the device.

It should be obvious to those skilled in the art that all of the descriptions herein are equally applicable to other types of AIMDs. These include implantable cardioverter defibrillators (ICDs), neurostimulators, including deep brain stimulators, spinal cord stimulators, cochlear implants, incontinence stimulators and the like, and drug pumps. The present invention is also applicable to a wide variety of minimally invasive AIMDs. For example, in certain hospital cath lab procedures, one can insert an AIMD for temporary use such as a probe, catheter or femoral artery ICD. Ventricular assist devices also can fall into this type of category. This list is not meant to be limiting, but is only example of the applications of the novel technology currently described herein. In the following description, functionally equivalent elements shown in various embodiments will often be referred to utilizing the same reference number.

FIG. 13 is a general diagram of a unipolar active implantable medical device 100 and related system, wherein reference numbers common with those used in FIG. 12 refer to common structural and/or functional components. The housing 124 of the active implantable medical device 100 is typically titanium, ceramic, stainless steel or the like. Inside of the device housing are the AIMD electronic circuits. Usually AIMDs include a battery, but that is not always the case. A leadwire or lead 104 is routed from the AIMD 100 to a point 140 typically including or comprising an electrode embedded in or affixed to body tissue. In the case of a spinal cord stimulator 100H (FIG. 1), the distal tip 140 could be in the spinal cord. In the case of a deep brain stimulator 100B (FIG. 1), the distal electrode 140 would be placed deep into the brain, etc. In the case of a cardiac pacemaker 100C (FIG. 1), the distal electrode 140 would typically be placed in the cardiac right ventricle.

FIG. 14 is very similar to FIG. 13 except that it depicts a bipolar device 100 and related system. In this case, a first lead 104 is coupled to a first distal electrode 140, and a second distal electrode142 and associated lead 106 provide an electric circuit return path between the two distal electrodes 140 and 142. In the case of a cardiac pacemaker 100C as shown in FIG. 15, this would be known as a bipolar lead system with one of the electrodes known as the distal tip electrode 140 and the other electrode which would float in the blood pool known as the ring electrode 142 (see FIG. 15). In contrast, the electrical return path in FIG. 13 is between the distal electrode 140 through body tissue to the conductive housing 124 of the implantable unipolar medical device 100.

In all of these applications, the patient could be exposed to the fields of an MRI scanner or other powerful emitter used during a medical diagnostic procedure, currents that are directly induced in the leads 104, 106 can cause heating by $P=I^2R$ (Ohm's law) losses in the leads or by heating caused by RF current flowing from the tip and ring electrodes 108, 110 into body tissue. If these induced RF currents become excessive, the associated heating can cause damage or even destructive ablation to body tissue.

The distal tip electrode 140 is designed to be implanted against or into or affixed (screwed into) to the actual myocardial tissue of the heart 136. The ring electrode 142 is designed to float in the blood pool. Because the blood is flowing and is thermally conductive, some people feel that the ring structure 142 is substantially cooled. However, this is only in theory. Studies have shown, upon lead removal that the entire area of the tip and the ring can become overgrown and embedded in body tissue and thereby thoroughly encapsulated. Accordingly, in some pacemaker patients, both the distal tip and ring can become thermally insulated by surrounding body tissue and can readily heat up due to the RF pulsed currents of an MRI field.

Figure 16:
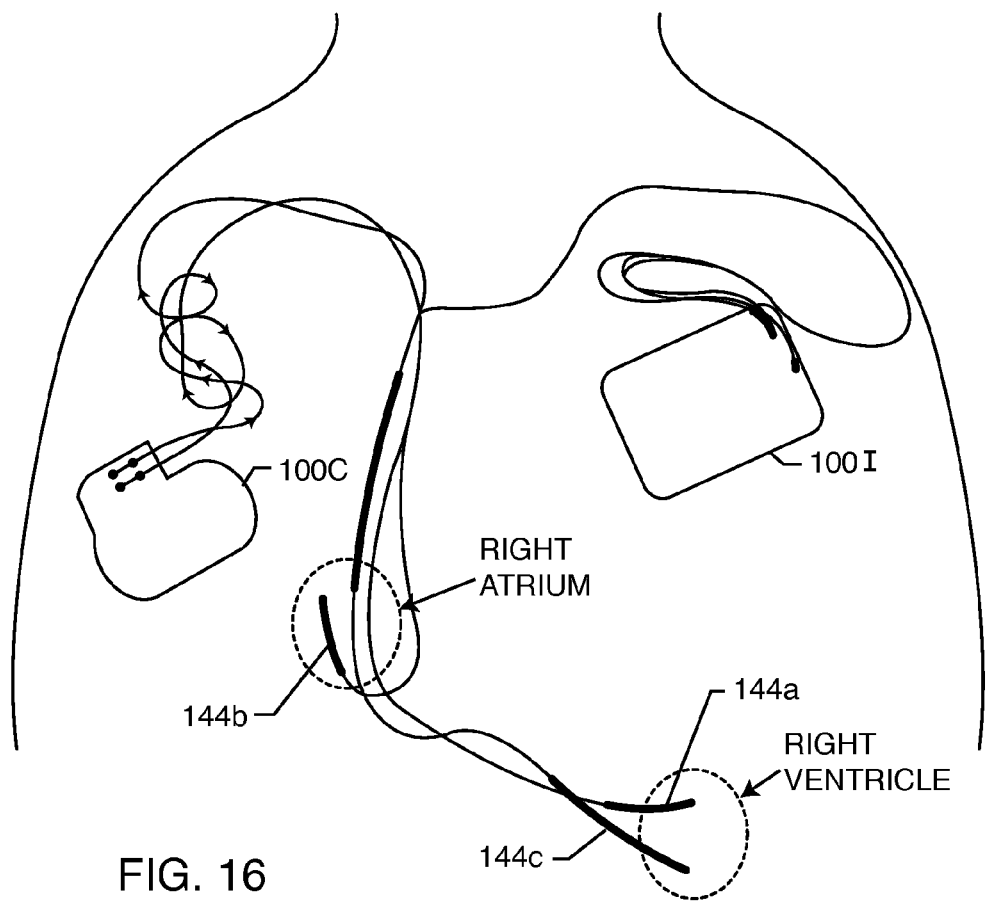
FIG. 16 is a tracing of an exemplary patient X-ray showing an implanted pacemaker and cardioverter defibrillator and corresponding lead system.

FIG. 16 is a tracing of an actual patient X-ray. This particular patient required both a cardiac pacemaker 100C and an implantable cardioverter defibrillator (ICD) 100I. The corresponding implantable leadwire system, as one can see, makes for a very complicated antenna and loop coupling situation. The reader is referred to the article entitled, "Estimation of Effective Lead Loop Area for Implantable Pulse Generator and Implantable Cardioverter Defibrillators" provided by the AAMI Pacemaker EMC Task Force.

In FIG. 16, one can see that from the pacemaker 100C, there is an electrode 144a and 144b in both the right atrium and in the right ventricle. Both these involve a separate tip and ring electrode (not shown in FIG. 16). In the industry, this is known as a dual chamber bipolar leadwire system. It will be obvious to those skilled in the art that any of the passive frequency selective networks, as previously described in FIGS. 2 through 11, can be incorporated into the leadwires as illustrated in the X-ray tracing of FIG. 16. One can also see that the implantable cardioverter defibrillator (ICD) 100I is associated with an electrode 144c implanted directly into the right ventricle. Its shocking tip and perhaps its superior vena cava (SVC) shock coil would also require the passive, frequency selective diverter and/or impeding filters of FIGS. 2-11 of the present invention so that MRI exposure cannot induce excessive currents into the associated leadwires or electrodes. Modern implantable cardioverter defibrillators (ICDs) incorporate both pacing and cardioverting (shock) features. Accordingly, it is becoming quite rare for a patient to have a leadwire layout as shown in the X-ray of FIG. 16. However, the number of electrodes remains the same. There are also newer combined pacemaker/ICD systems which include biventricular pacemaking (pacing of the left ventricle). These systems can have as many as 9 to even 12 leadwires.

Figure 17:
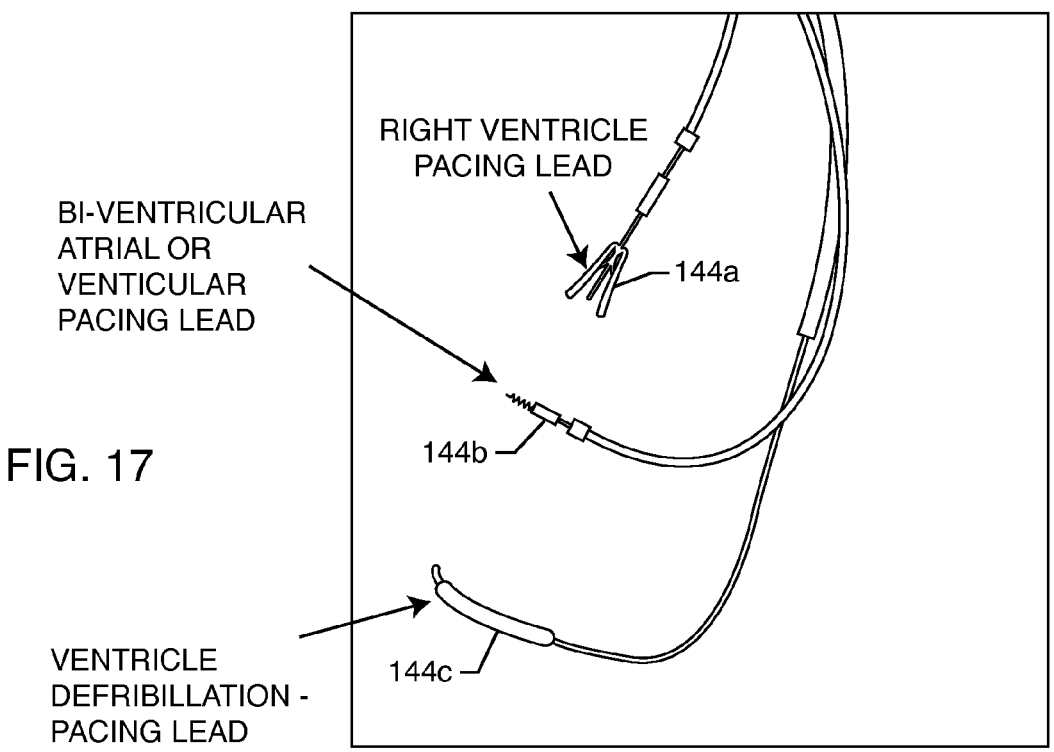
FIG. 17 is a line drawing of an exemplary patient cardiac X-ray of a bi-ventricular lead system.

FIG. 17 is a line drawing of an actual patient cardiac X-ray of one of the newer bi-ventricular leadwire systems with various types of electrode tips 144a, 144b and 144c shown. The new bi-ventricular systems are being used to treat congestive heart failure, and make it possible to implant leads outside of the left ventricle. This makes for a very efficient pacing system; however, the implantable leadwire system is quite complex. When a leadwire system, such as those described in FIGS. 12, 13, 14, 15, 16 and 17, are exposed to a time varying electromagnetic field, electric currents can be induced into the electrodes of such leadwire systems. For the bi-ventricular system, a passive component frequency selective network of FIGS. 2-11 would need to be placed in conjunction with each of the three distal tips and ring electrodes to corresponding energy dissipating surfaces.

The word passive is very important in this context. Active electronic circuits, which are defined as those that require power, do not operate very well under very high intensity electromagnetic field conditions. Active electronic filters, which generally are made from microelectronic chips, have very low dynamic range. Extremely high fields inside an MRI chamber would tend to saturate such filters and make them become nonlinear and ineffective. Accordingly, frequency selective networks are preferably realized using non-ferromagnetic passive component elements. Passive component elements are capable of handling very high power levels without changing their characteristics or saturating. Moreover, the inductor elements are preferably made from materials that are not ferromagnetic. The reason for this is that MRI machines have a very powerful main static magnetic field ($B_0$). This powerful static magnetic field tends to saturate ferrite elements and would thereby change dramatically the value of the inductance component. Accordingly, virtually all inductor elements are fabricated without the use of ferrites, nickel, iron, cobalt or other similar ferromagnetic materials that are commonly used in general electronic circuit applications.

Figure 18:
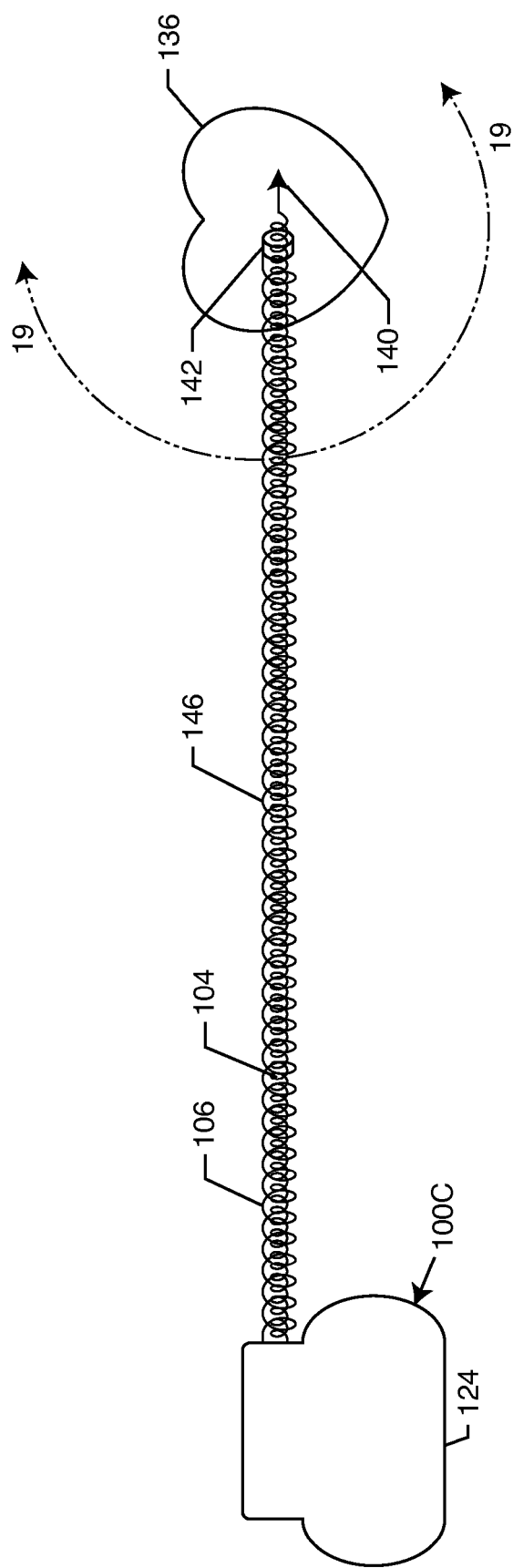
FIG. 18 illustrates a bipolar cardiac pacemaker lead showing the distal tip and the distal ring electrodes.

FIG. 18 illustrates a single chamber bipolar cardiac pacemaker 100C having a lead system and showing the distal tip 140 and the distal ring electrodes. This is a spiral wound (coaxial) lead system where a ring coil lead 106 is wrapped around a tip coil lead 104, wherein these two leads 104, 106 extend between a sealed housing 124 and the pair of electrodes 140, 142. There are other types of pacemaker lead systems in which these two leads that lay parallel to one another (known as a bifilar lead system, which are not shown.). In FIG. 18, one can see an outer insulating sheath 146 which is typically of silicone or polyurethane. This protects the leadwires 104, 106 from direct exposure to body fluid and also insulates the leadwires. It also has its own thermal conductive properties as will be further described herein.

Figure 19:
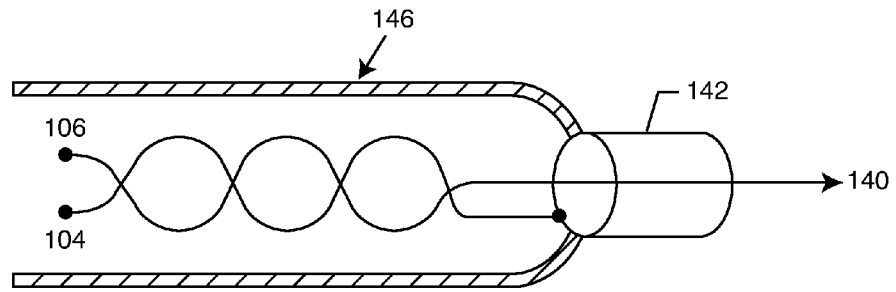
FIG. 19 is an enlarged schematic illustration of the area indicated by Line 19-19 in FIG. 18, showing details of the bipolar pacemaker lead system.
Figure 19A:
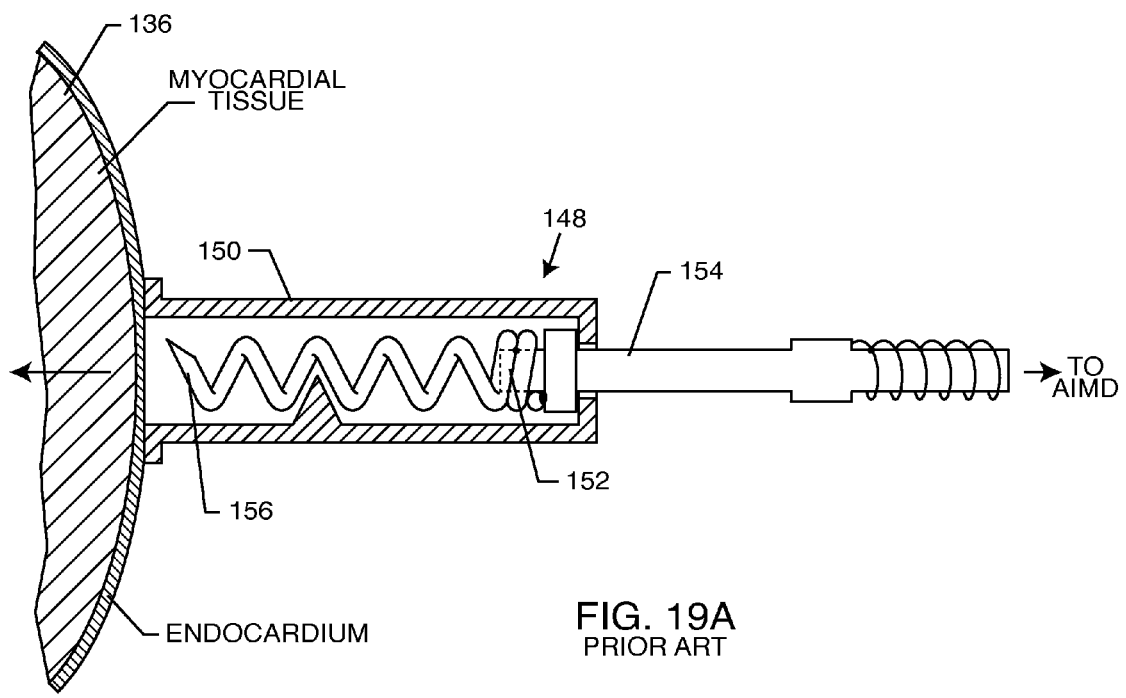
FIG. 19A is similar to FIG. 19, but depicts an active fixation tip for a bipolar pacemaker lead system.

FIG. 19 is generally taken from FIG. 18 showing a typical prior art bipolar pacemaker leadwire system. Shown is the distal tip electrode 140 and ring electrode 142. An insulation or insulative lead body 146 is also illustrated. The distal tip electrode can be passive (meaning that it can be bent back in a "j" or shoved against myocardial tissue so that it just rests against the tissue). A more commonly used electrode today is known as the active fixation tip. This is an electrode where by turning the entire center of the lead, the physicians can screw a helix into myocardial tissue thereby firmly affixing it. A prior art active fixation electrode tip 148 is shown in FIG. 19A. This is typically used in conjunction with a cardiac pacemaker, an implantable defibrillator or the like. One can see that an active fixation tip housing 150 is pressed up against the tissue to be stimulated, e.g., the myocardial tissue of the patient's heart 136. For example, this could be the septal wall between the right ventricle and the left ventricle. A helix electrode assembly 152 is shown in a retracted position relative to the adjacent heart tissue. Up in the pectoral pocket, the physician uses a tool to axially twist an assembly shaft 154, which drives a pointed tip helix screw 156 into the myocardial tissue, firmly affixing it. This type of active fixation tip 148 is becoming more popular. As can be seen, it would be highly undesirable for the active fixation helix screw 156 to heat up during an MRI scan. Because the helix screw 156 is deeply embedded into myocardial tissue, if excessive heating and temperature rise did occur, not only could scarring or ablation of cardiac tissue occur, but an actual cardiac wall perforation or lesion could result in sudden death. It will also be obvious to those skilled in the art that any of the frequency impeding or diverting circuits, as shown in FIG. 4, 5, 6, 7, 10 or 11, would be highly undesirable if they were located within the overall housing 150 of the active fixation tip 148. This is because the heat would indeed be removed from the helix screw 156, but it would be transferred into the active fixation housing 150 which rests in intimate contact with the endocardium heart tissue. What this means is that redirecting the MRI induced electromagnetic energy from the helix tip 156 to the housing 150 simply moves the heat from one bad location to another bad location. Because the housing 150 is also in intimate contact with heart tissue, one would experience excessive temperature rise and resulting tissue burning, scarring or necrosis at that location as well.

Referring once again to FIG. 19, one can see that there is a ring electrode 142 which is placed back (spaced proximally) a suitable distance from the distal tip electrode 140. In a bipolar pacing system, the cardiac pacing pulse is produced between the tip electrode 140 and the ring electrode 142. This electrical pulse induced into myocardial tissue produces a heartbeat. Sensing is also accomplished between these two electrodes 140, 142 wherein the pacemaker can constantly monitor the electrical activity of the heart. There are similar analogies for neurostimulators, cochlear implants and the like. There is usually a point at which the distal electrodes, for example electrode 140, contact body tissue or fluid for delivery of therapy involving electrical energy. In a neurostimulator application, such as a spinal cord stimulator, small electrical currents or pulses are used to block pain in the spinal nerve roots. In a urinary incontinence stimulator, a distal electrode is used to cause a muscle contraction and thereby prevent undesirable leakage of urine. In all of these examples, it would be highly undesirable for excess heating defined as temperature rise above a few degrees C., to occur particularly at the distal electrode tip(s).

In previous studies, concerns have been raised about the safety of using metallic structures, such as leadwires and MR scanners. Radio frequency energy (MHz) transmitted from the MRI scanner in order to generate the MR signal can be coupled to on the interventional device or its associated leads. This results in high electrical fields around the instrument and local tissue heating. This heating tends to be most concentrated at the ends of the electrical structure or leads.

We can address this safety issue using the methods of the present invention. The concern is that distal electrodes or distal surface ring electrodes, which directly contact body tissue, will cause local tissue burns. We need to cut/remove the electrodes from the circuit in the MHz frequency range. In the current embodiment, this is accomplished with inductor circuit elements. In the MHz frequency range, the surface ring electrodes are not connected to the rest of the electrical leads (FIG. 9). Therefore, the ends of the leads are now buried inside of the catheter. The concentrated, high electric fields will now be located inside of the catheter instead of in the tissue. This results in a significant reduction in unwanted tissue heating.

A more effective way to "cut" or impede RF energy from the surface electrodes from the rest of the circuit would be to use a parallel resonant circuit in place of the inductors in FIG. 10. This resonant circuit could consist of an inductor in parallel with a capacitor (an L-C bandstop filter as shown in FIG. 11). If this parallel L-C circuit is tuned to the MR frequency, it will present a very high impedance at this frequency. This will effectively cut the surface electrodes from the elongated leads at the MRI frequency and prevent unwanted heating. For maximal effectiveness, the L-C circuit should be shielded. For a probe or a catheter application, with these design concepts, the electrical end of the leads (in the MHz range) are buried inside of the catheter body and as a result, the concentrated electric fields are also located inside of the capacitor, instead of in the tissue. This results in a significant reduction in unwanted tissue heating. As previously mentioned, a resonant circuit is an effective way to "cut" the surface electrodes from the rest of the electrical circuit. This resonant circuit could be an inductor in parallel with the capacitor (an L-C "tank" circuit). The L-C circuit may be placed distal to the electrodes and allowing the electrodes to be visualized. Probes and catheters often incorporate metallic sheaths which also assist in dissipating the unwanted energy over large surface areas. This is equivalent to the energy dissipating surface structures as described herein.

All of the circuit elements as described in connection with FIGS. 4 through 11 are for purposes of redirecting high frequency RF energy away from distal electrodes into a location that has larger thermal mass and larger area such that the energy is not being dissipated at the concentrated point of electrode to tissue contact. Concentrating the MRI RF energy at an electrode causes excessive temperature rise which can result in damage to adjacent body tissues. Referring back to FIG. 3, one can see that the leadwires 104 and 106 are embedded in the insulating sheath of a probe, a catheter, a cardiac pacemaker lead or the like. Accordingly, if excess heat is dissipated along these leadwires, it is then dissipated into these surrounding structures. As previously mentioned, there is also a parasitic capacitance that's formed along these leadwires and the surrounding structures or insulating sheaths. It is a feature of the present invention that any of the passive component frequency selective circuits can also be directly connected to energy dissipating elements that are distal from the electrodes themselves.

Referring to FIG. 19 (and also FIGS. 20-22), the insulation sheath 146 typically encapsulates the leadwires 104 and 106 in silicone or polyurethane to provide strength and resistance to body fluids. The insulation sheath 146 has thermal conduction properties and also provides important electrical isolation between the leadwires 104 and 106 themselves and also surrounding body fluids and tissues.

Figure 20:
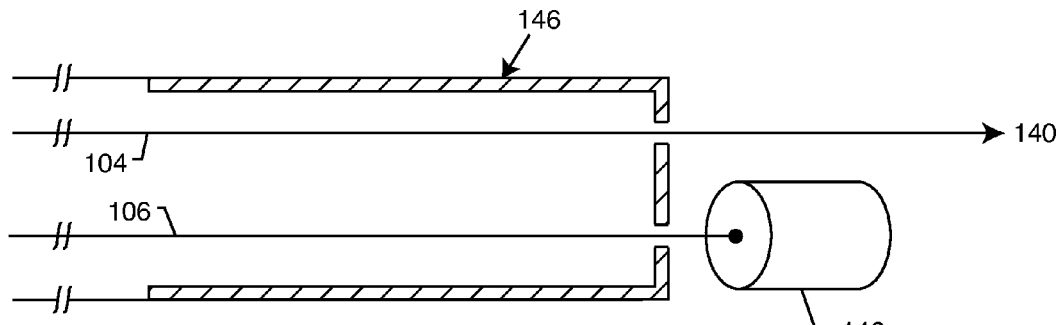
FIG. 20 is similar to FIG. 19, except that the twisted or coaxial electrode wires have been straightened out.

FIG. 20 is generally taken from FIG. 19 except that the twisted or coaxial electrode wires 104 and 106 have been straightened out for better illustration of the examples of the present invention. This is also analogous to FIG. 2 for the wires of probes and catheters previously described herein. The straightened and elongated leadwires 104, 106 of FIG. 20 are also illustrative of certain bifilar leadwire systems, which can also be used for pacemakers, neurostimulators and the like. In other words, the leadwires are not always twisted as shown in FIG. 19 as there are certain applications where it is desirable to have the leadwires 104, 106 running parallel to each other in a straight fashion. For illustrative purposes, we will focus on the straight leadwires 104, 106 of FIG. 20, but realize that all of these same principles to follow are equally applicable to twisted or coaxial leadwires as shown in FIG. 19. In FIG. 20, one can see that the insulation sheath 146 generally runs up to and fixates the ring electrode 142, but does not cover or encapsulate it. This is also true for the distal tip electrode 140. This is important such that the electrodes are not insulated, so that they can deliver therapy and/or sense biologic signals. If they were insulated, they would not be able to function and conduct electrical current into body tissue. In practice, the parasitic capacitance value is quite low. For differential mode induced EMFs, by electrically shorting leadwires 104 and 106 together, the energy induced from an MRI system is contained into a loop whereby it will create relatively high RF currents in leadwires 104 and 106. Importantly, this loop disconnects this current flow from the distal electrodes 140 and 142. Accordingly, this energy will be converted to heat within leadwires 104 and 106 where it will be thermally conducted into the insulation sheath 146 and dissipated over a much larger surface area. In the case where the induced EMFs are common mode, frequency selective networks of the present invention are used to conduct the high frequency energy to a metallic surface of the probe or catheter, such as a shield, or to an equivalent energy dissipating surface. This has the effect of preventing a large temperature rise at the electrode to tissue interface which could be damaging to body tissue. More importantly, said heat is diverted away from the distal electrodes, which make direct contact with sensitive body tissues. It is in this location where excessive heat dissipation can cause temperature rises that can cause damage to body tissue and therefore, undesirable loss of therapy or even life-threatening tissue damage. In a preferred embodiment, the parasitic capacitances or heat conductive interface would be replaced by passive component capacitances that are connected directly to a conductive energy dissipating surface. This is a more efficient way of diverting the energy to a point distant from the distal electrodes and converting it to heat. By re-directing the RF and/or thermal energy to a point or an area distant from the distal electrodes, one thereby provides a high degree of protection to the sensitive junction between the electrodes and body tissue. For example, that junction may be the point where a distal electrode contacts myocardial tissue and provides critically important pacing pulses. Energy concentration at distal electrode can cause dangerous temperature rises.

Figure 21:
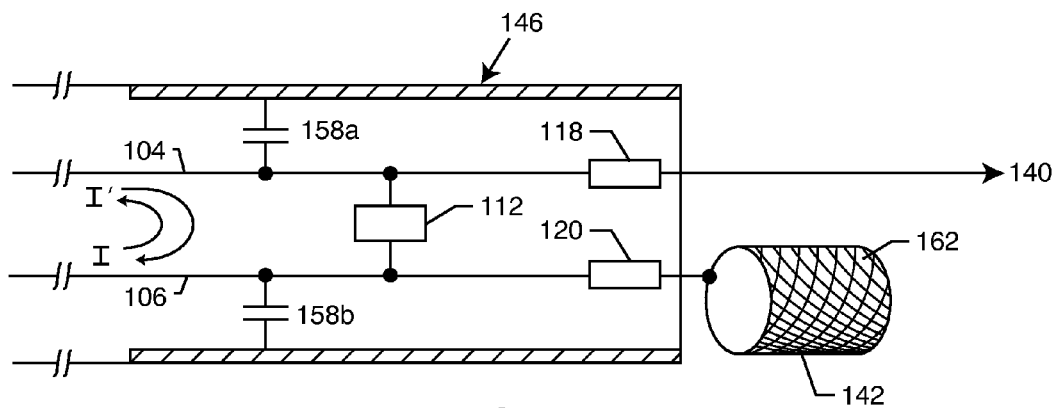
FIG. 21 is similar to FIG. 20 and incorporates electrical features discussed in FIGS. 2-11.

FIG. 21 is generally equivalent and incorporates and embodies the concepts previously described in FIGS. 2 through 11 herein. In FIG. 21, one can see the lead insulation 146. There is a parasitic capacitance 158*a* and 158*b* which is formed between leadwires 104 and 106 and the insulation layer 146. At high frequency, this has the desired effect of diverting or shunting high frequency MRI RF energy away from the leadwires 104 and 106 thereby redirecting energy into the insulation sheath 146 where it can be dissipated over a much larger surface area with minimal temperature rise. Series reactive elements 118 and 120, as previously described and shown in connection with FIG. 7, block, cut or impede the flow of MRI induced RF energy to the distal tip electrode 140 and/or the distal ring electrode 142, wherein these electrodes 140, 142 correspond respectively with the ring electrodes 108, 110 shown in FIGS. 2-11. These series frequency selective reactances 118 and 120 are optional, but do increase the efficacy of the present system.

Reactance 112 can be a simple capacitor as shown in FIG. 5, or it can be an L-C series trap filter as shown in FIG. 6. This tends to short leadwires 104 and 106 together at high frequency thereby diverting undesirable high frequency energy and thereby preventing it from reaching distal tip electrode 140 or ring electrode 142. Referring once again to FIG. 21, we can see high frequency RF currents I and I'. These, for example, are the RF pulsed currents induced in an elongated implanted lead from a 1.5 Tesla MRI system, and they would oscillate back and forth at 64 MHz thereby reversing directions, as shown, at that frequency. This is better understood by referring to FIG. 9. The currents are cut off (as indicated at 122 in FIG. 9) and are effectively contained within leadwires 104 and 106. This redirects the energy that is induced by the high frequency MR fields back into the insulation sheath 146 at a point distant from the distal electrodes 140 and 142. This desirably prevents the distal electrodes from overheating at their point of contact with body tissue.

Figure 22:
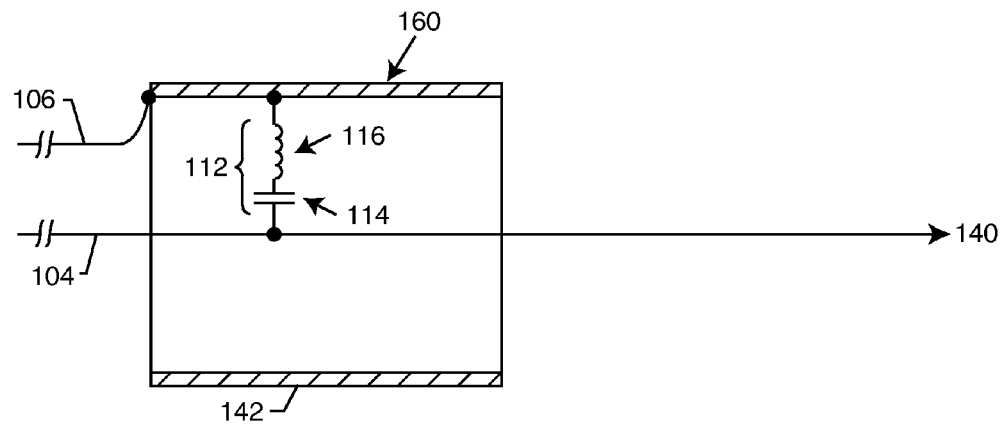
FIG. 22 is similar to a portion of FIGS. 20 and 21, and depicts an L-C trap filter coupled between a distal tip electrode wire and a cylindrical ring electrode.

FIG. 22 is very similar to the structures shown in FIGS. 19 and 20 for active implantable medical devices (AIMDs) such as cardiac pacemakers and the like. Shown is a selective frequency element 112 in accordance with FIG. 6, which in this case consists of an inductor 116 in series with a capacitor 114 (trap filter). The component values of the inductor 116 and the capacitor 114 can be selected such that they are resonant at a particular frequency. In this case, for illustrative purposes, they shall be resonant at 64 MHz thereby providing a low impedance short circuit for 1.5 Tesla MRI signals. This has the effect of diverting or shunting the energy off of leadwire 104 to the relatively large surface area of the ring electrode 142. The ring electrode 142 is typically a metallic structure consisting of a cylindrical ring and very high thermal conductivity. It also has, by necessity, very high electrical conductivity. Accordingly, referring once again to FIG. 22, the ring electrode 142, by its inherent nature, becomes an energy dissipating surface 160 wherein the high frequency RF energy is diverted to it, wherein said RF energy will either be converted to heat, which will be directed into the surrounding blood flow, or said RF energy will be harmlessly dissipated into surrounding body tissues. More specifically, for example, in the right ventricle, the distal tip electrode 140 is designed to be screwed into myocardial tissue in accordance with FIGS. 19 and 19A. The ring electrode 142, on the other hand, is designed to be placed back away from distal tip electrode 50 such that it actually floats in the pool of blood that is flowing in the particular cardiac chamber. In an ideal situation, the wash of blood over it tends to provide a constant cooling action through heat transfer over the ring electrode 142 thereby dissipating undesirable heat from high frequency RF energy harmlessly into the flowing blood (or other body fluid such as lymph in other applications). A disadvantage of this approach is that in a certain percentage of patients both the tip and the ring tend to be overgrown by tissue. Accordingly, the use of a separate energy dissipating surface 160, which is located further back from both the distal tip and ring electrode, is desirable such that it is guaranteed to remain in the blood pool. For the energy dissipating surface 160, which can either be the ring electrode itself or a separate energy dissipating structure 160, it is a desirable feature that it includes some type of biomimetic coating such that tissue overgrowth is inhibited. Referring back to FIG. 21, for example, a biomimetic coating 162 could be deposited all over the ring electrode to thereby inhibit tissue overgrowth.

Figure 23:
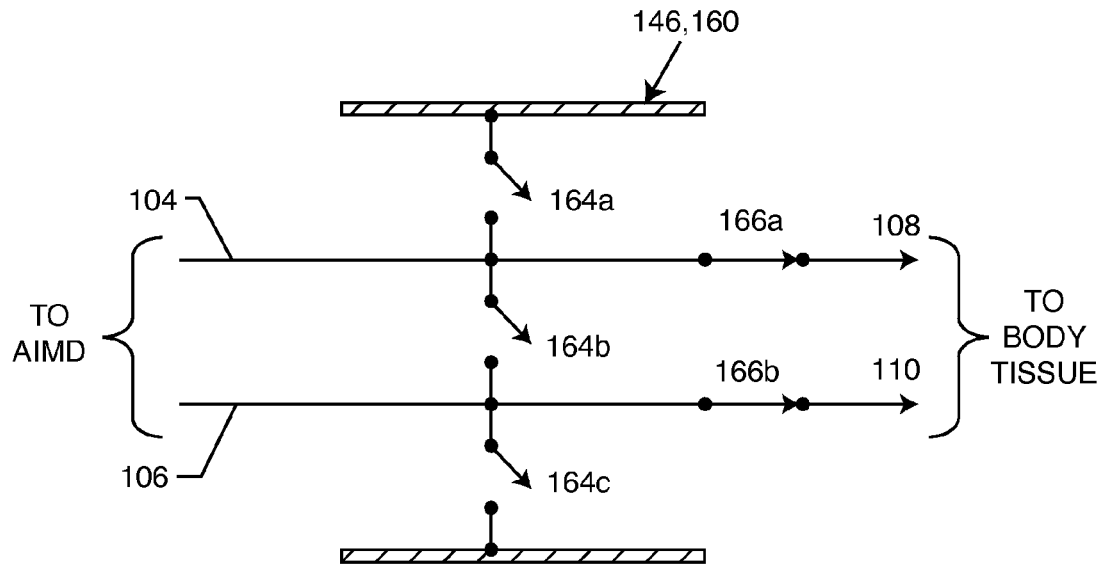
FIG. 23 is a schematic low frequency model illustration operation of the embodiment depicted generally at FIGS. 7-8.

FIG. 23 is a low frequency model illustrating the concepts previously shown and described in connection with FIG. 7. Switches are used to illustrate the properties of the reactances at low frequency. Referring back to FIGS. 21-22, one can see that there is an insulation sheath 146 or energy dissipating surface 160. The parallel reactance element 112, as illustrated in FIGS. 4, 5 and 6, is represented respectively by switches 164a, 164b and 164c. At low frequency, these reactances tend to look like very high impedances and are therefore shown as open switches. On the other hand, the series reactances 118 and 120, as previously illustrated and described in FIGS. 7, 10 and 11, tend to look like a very low impedance approximating short circuits at low frequency and are thus shown respectively as closed switches 166a and 166b. Accordingly, the low frequency model, as illustrated in FIG. 23, is completely equivalent to the low frequency model previously shown and described in connection with FIG. 8. In this case, the reactive elements 112, 118 and 120 effectively disappear from the electrical model, whereby the pair of electrodes 104, 106 is coupled directly and respectively to the pair of electrodes 108 and 110.

Figure 24:
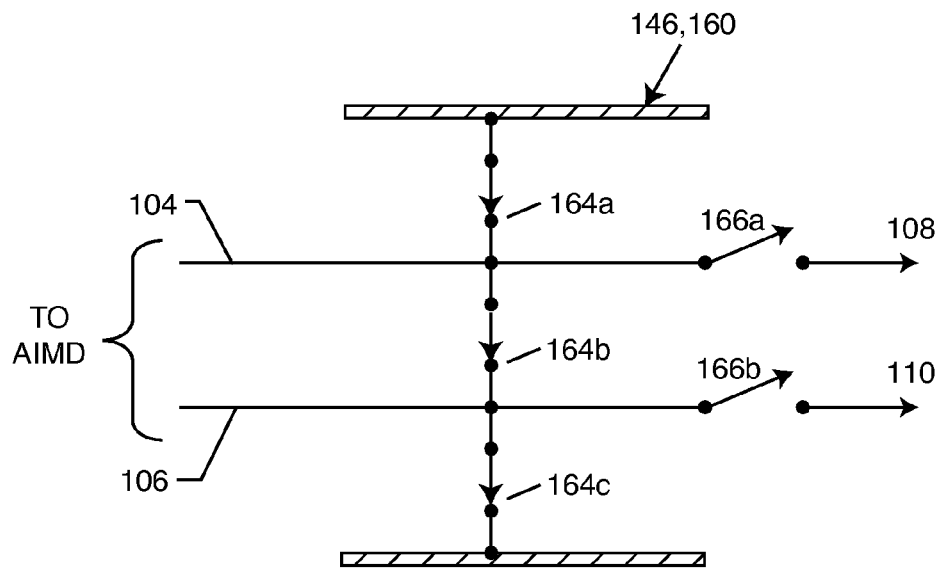
FIG. 24 is a schematic diagram similar to FIG. 23, but shows a high frequency model of the embodiment depicted generally at FIGS. 7 and 9.

FIG. 24 is the high frequency model of FIG. 7. In this case, the reactance element 112, previously illustrated in FIGS. 4, 5 and 7, tends to look like a very low impedance at high frequency and therefore, is represented as a closed switch (or short circuit) as shown by switches 164a, 164b, and 164c. In FIG. 24, one can see that the series reactance components 118, 120 of FIGS. 7, 10 and 11 look like very high impedances (ideally open circuits) at high frequency and are thereby shown as open switches 166a and 166b. Therefore, the high frequency model, as illustrated in FIG. 24, is completely equivalent to the high frequency model previously described and shown in connection with FIG. 9. Of course, these switches do not really physically exist and are simply a way of illustrating the behavior of the passive component frequency selective networks that are described in FIGS. 4 through 11.

Figure 25:
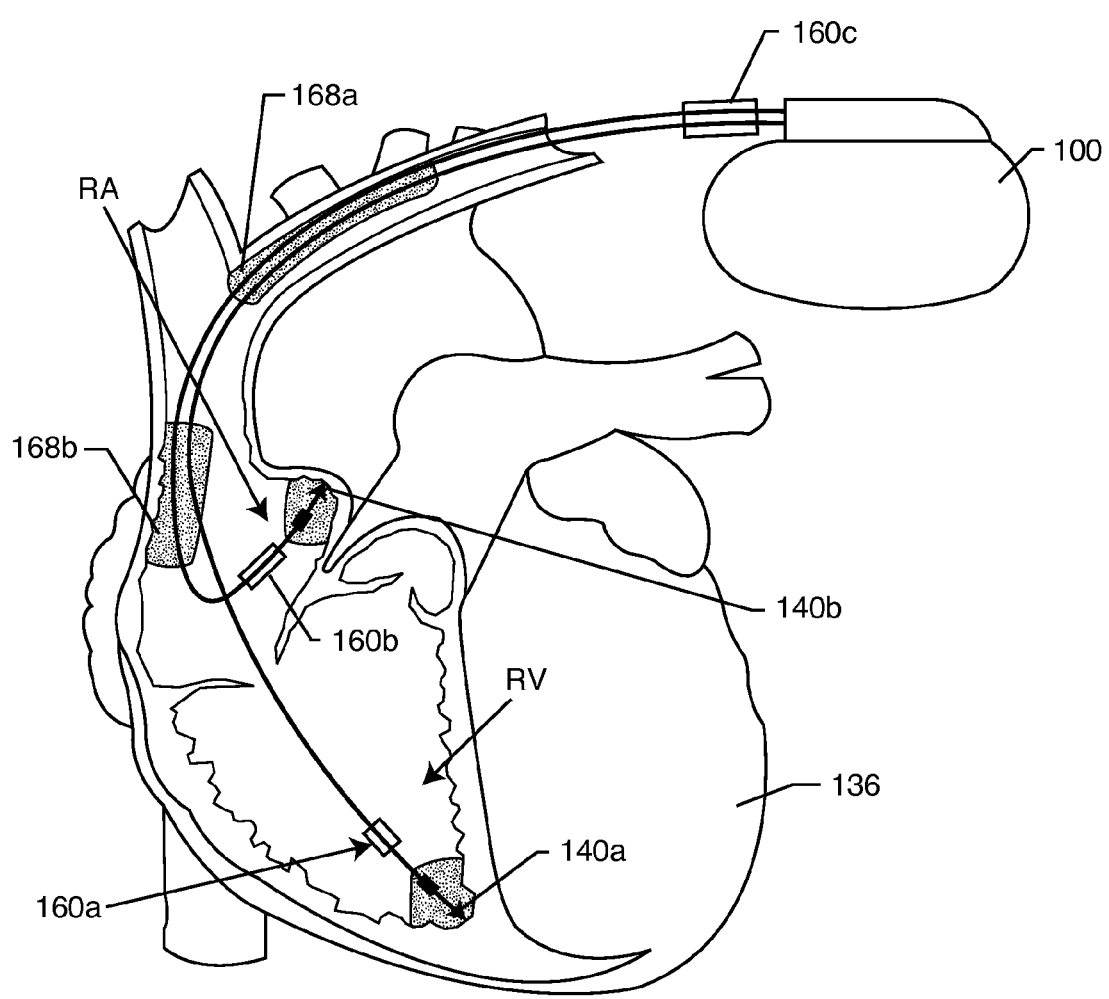
FIG. 25 is a line drawing of a human heart with cardiac pacemaker dual chamber bipolar leads shown in the right ventricle and the right atrium.

FIG. 25 is a line drawing of a human heart 136 with cardiac pacemaker dual chamber bipolar leads shown in the right ventricle RV and the right atrium RA of a human heart 136. FIG. 25 is taken from slide number 3 from a PowerPoint presentation given at The 28$^{th}$ Annual Scientific Sessions of the Heart Rhythm Society by Dr. Bruce L. Wilkoff, M. D. of the Cleveland Clinic Foundation. This article was given in Session 113 on Friday, May 11, 2007 and was entitled, ICD LEAD EXTRACTION OF INFECTED AND/OR REDUNDANT LEADS. These slides are incorporated herein by reference and will be referred to again simply as the Wilkoff reference. In FIG. 25, one can see multiple leads extending from an active implantable medical device 100 (such as a cardiac pacemaker or the like) coupled to associated electrodes, one of which comprises the distal tip ventricular electrode 140a located in the right ventricular (RV) apex. The dark shaded areas in FIG. 25 show the experience of the Cleveland Clinic and Dr. Wilkoff (who is a specialist in lead extraction), where extreme tissue overgrowth and vegetation tends to occur. There are numerous cases of extracted leads where both the tip and ring electrodes have been overgrown and encapsulated by tissue. Referring once again to FIG. 25, one can see tip electrode 140a, which is located in the right ventricular apex. The shaded area encasing this electrode 140a shows that this area tends to become encapsulated by body tissue. An electrode 140b in the right atrium (RA) may similarly be overgrown and encapsulated by tissue, as shown by the encasing shaded area. There are other areas in the superior vena cava and venous system where leads tend to be encapsulated by body tissue a great percentage of the time. These are shown as areas 168a and 168b. This is particularly important to know for the present invention since these would be highly undesirable areas to place an energy dissipating surface 160 in accordance with the present invention. Ideal locations for energy dissipating surfaces are shown as 160a, 160b and 160c.

Referring once again to FIG. 25, as previously mentioned, it is very important that this lead system does not overheat during MRI procedures particularly at or near the distal tip electrodes and rings. If either or both the distal tip and ring electrode become overgrown by body tissue, excessive overheating can cause scarring, burning or necrosis of said tissues. This can result in loss of capture (loss pacing pulses) which can be life-threatening for a pacemaker dependent patient. It is also the case where implanted leads are often abandoned (where the lead has been permanently disconnected from the AIMD). Often times when the device such as a pacemaker 100 shown in FIG. 25 is changed out, for example, due to low battery life and a new pacemaker is installed, the physician may decide to install new leads at the same time. Leads are also abandoned for other reasons, such as a dislodged or a high impedance threshold. Sometimes over the course of a patient life-time, the distal tip electrode to tissue interface increases in impedance. This means that the new pacemaker would have to pulse at a very high voltage output level which would quickly deplete its battery life. This is yet another example of why a physician would choose to insert new leads. Sometimes the old leads are simply extracted. However, this is a very complicated surgical procedure which does involve risks to the patient. Fortunately, there is plenty of room in the venous system and in the tricuspid valve to place additional leads through the same pathway. The physician may also choose to implant the pacemaker on the other side. For example, if the original pacemaker was in the right pectoral region, the physician may remove that pacemaker and choose to install the new pacemaker in the left pectoral region using a different part of the venous system to gain lead access. In either case, the abandoned leads can be very problematic during an MRI procedure. In general, prior art abandoned leads are capped with a silicone cap at their proximal connector points so that body fluids will not enter into the lead system, cause infections and the like. However, it has been shown in the literature that the distal electrodes of abandoned leads are at high risk to heat up during MRI procedures. Accordingly, a passive frequency selective circuit of the present invention is very useful when placed at or near the proximal electrical contact after a pacemaker is removed and its leads are disconnected (abandoned). For example, for an abandoned (left in the body) lead, an energy dissipating surface 160c at or near the proximal lead end is an ideal place to eliminate excess energy induced by MRI in the leadwire system.

Referring back to the article by Dr. Bruce Wilkoff, attention is drawn to slide number 2, which is an example of a lead extraction showing both a distal tip electrode and a distal ring which have been heavily overgrown and encapsulated by body tissue. Special cutting tools were used to free the lead so it could be extracted, so the tissue shown here is only a small remaining portion of the mass that was originally present. Slide 13 is a dramatic illustration of what a larger mass of encapsulated tissue would look like. In this case, the entire tip was completely surrounded, but if one looks carefully to the right, one can see that some of the ring was still exposed. The situation is highly variable in that the ring is not always fully encapsulated. Slide 16 is an example of tissue removal after a pacemaker bipolar lead was extracted. One can see at the end of the lead, the helix screw that was affixed to myocardial tissue. The surgeon in this photo was removing the tissue encapsulation, which completely surrounded the tip and is still surrounding the ring area. A blow-up of this is shown in slide 17. Again, the tissue that is still affixed to the lead has completely encapsulated the ring, which cannot be seen. Accordingly, there is a need for either a way to prevent the overgrowth of body tissue onto the ring or to ensure that an energy dissipating surface 160 is located far enough away from myocardial tissue to guarantee that it will remain floating in the blood pool.

Figure 26:
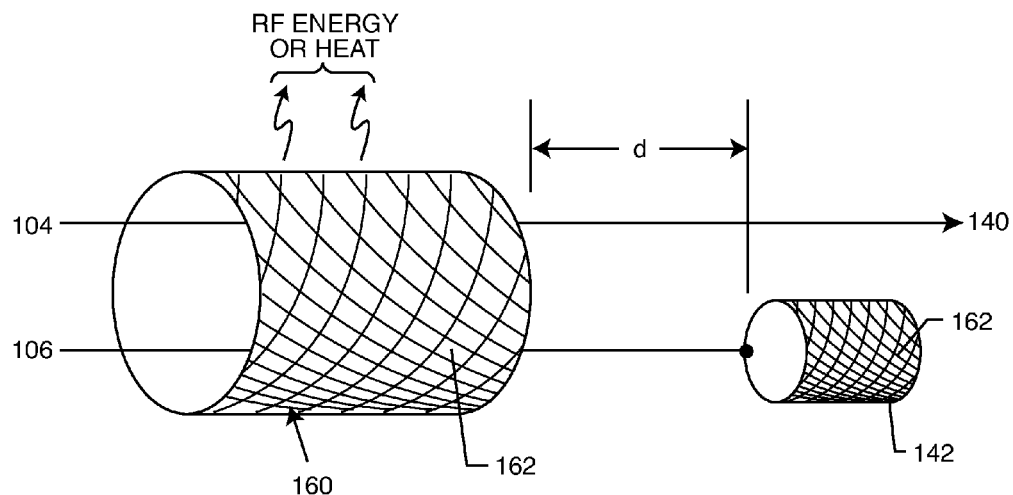
FIG. 26 is a schematic diagram illustration an energy dissipating surface in spaced relation with tip and ring electrodes.

FIG. 26 illustrates an energy dissipating ring 160 which is located at some distance "d" from both a pacemaker tip electrode 140 and a ring electrode 142 mounted respectively at the distal ends of leadwires 104 and 106. The distance "d" should be sufficient so that the energy dissipating surface 160 is far enough away from both the distal tip and ring electrodes 140, 142 such that there is no heating or temperature rise associated with the tissues that contact the tip and ring electrodes. Another advantage of moving the energy dissipating surface 160 away from the distal electrodes, particularly for a cardiac pacemaker application, is that there would be less tendency for the energy dissipating surface 160 to become encapsulated or overgrown with vegetated body tissue. If the energy dissipating surface 160, when it is disassociated at some distance from the electrodes 140, 142, does become overgrown with body tissue, this is not of great concern. Obviously, it would be superior to have the 160 surface floating in freely flowing blood so that there would be constant cooling. However, for example, if the 160 surface did touch off to the right ventricular septum and became overgrown, the only effect would be a slight heating of tissue in an area that is far away from where the actual electrical stimulation and sensing is being done by the electrodes. The ideal distance for the energy dissipating surface 160 does depend on the particular application and ranges from approximately 0.1 cm to 10 cm distance from the distal electrodes.

Referring once again to FIG. 26, the energy dissipating surface 160 is shown as a cylindrical ring. It can be semicircular, rectangular, octagonal, hexagonal or even involve semi-circles on the lead or any other metallic or similar structure that is also thermally conductive. Literally any shape or geometry can be used as an energy dissipation surface 160. It is a desirable feature of the present invention that the surface area be relatively large so that it can efficiently dissipate heat into the surrounding blood pool and surrounding tissues that are distanced from the electrodes. In FIG. 26, within the ring, there are electrical connections (not shown) between leadwire 104 and 106 and to the surface 160 that embody the passive frequency selective circuits previously discussed in connection with FIGS. 2 through 11. The purpose of these frequency selective circuits is to remove RF induced energy caused by the RF pulsed field of MRI from leadwires 104 and 106 and redirect it to the surface 160 where it is dissipated as heat. By having a large surface area, the heat can be dissipated without significant temperature rise such that surrounding tissues would be burned.

In cardiac rhythm management applications, the ring 160 is ideally located in areas where there is freely flowing blood, lymph or equivalent body fluids which adds to the cooling. A biomimetic coating 162 can be applied to the energy dissipating surface area 160 and/or to the ring electrode 142 if it is used as an energy dissipating surface. This special biomimetic coating 162 provides a non-thrombogenic and antiadhesion benefits. This coating can be comprised of a surfactant polymer having a flexible polymeric backbone, which is linked to a plurality of hydrophobic side chains and a plurality of hydrophilic side chains. This coating prevents the adhesion of certain plasma proteins and platelets on the surface and hence initiation of the clotting cascade or colonization of bacteria. Biomimetic coatings also tend to prevent overgrowth or adhesion of body tissues as illustrated in the Wilkoff paper. This polymer compound is described in U.S. Pat. Nos. 6,759,388 and 7,276,474, the contents of both patents being incorporated by reference herein. Additional benefits of biomimetic coatings include the prevention of bacterial colonization and resulting infections. It will be obvious to those skilled in the art that other types of coatings could be used on the ring 160 to inhibit or prevent overgrowth of body tissue. As used herein, the term biomimetics includes all such type coatings.

Figure 27:
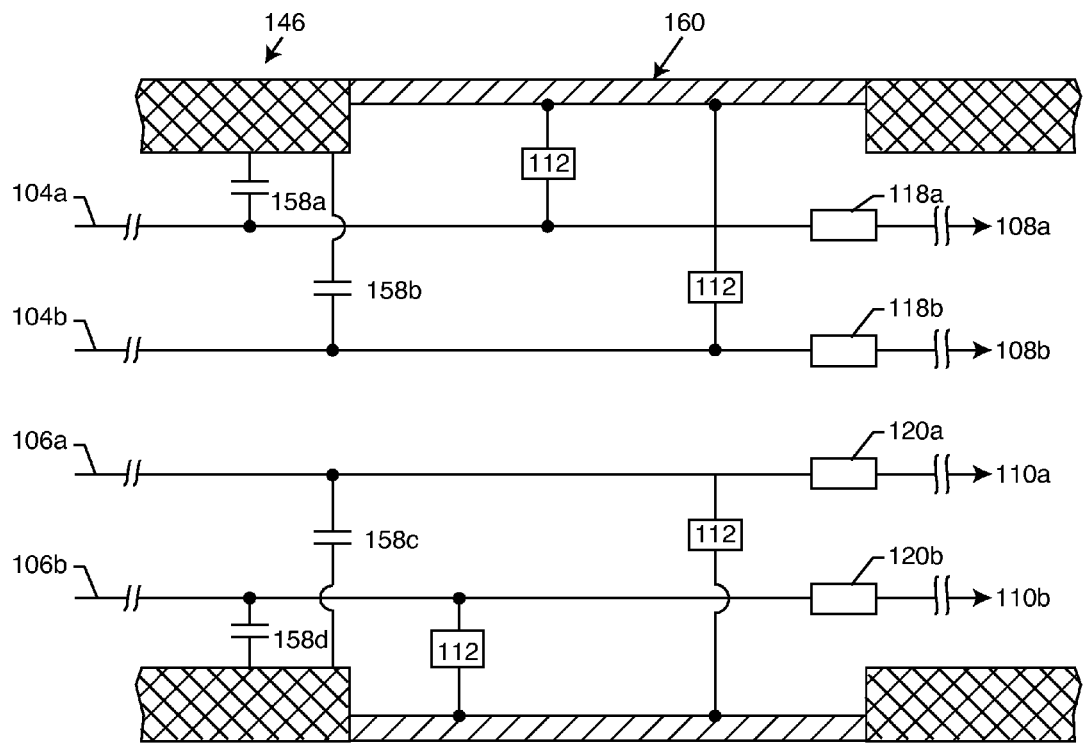
FIG. 27 a schematic diagram depicting a typical quad polar neurostimulation lead system.

FIG. 27 is a typical quad polar neurostimulation lead system. It will be appreciated that the following discussion also applies to bipolar, hex polar, and even electrode lead systems 108, 116. In FIG. 27, four leadwires 104a, 104b, 106a and 106b are shown which are each directed respectively toward an associated distal electrode 108a, 108b, 110a and 110b. In this case, the electrical stimulation pulses are applied in various combinations between the various electrodes. Unlike a cardiac pacemaker application, there is no particular ring electrode in this case. However, the insulation sheath 146 that surrounds the leadwires, which as mentioned could be of silicone or the like, forms a surrounding surface, which encapsulates the leadwires.

Parasitic capacitances 158a, 158b, 158c and 158d are formed respectively between each of the leadwires 104a, 104b, 106a and 106b and the insulating sheath 146. As previously mentioned, these parasitic capacitances can divert high frequency pulsed RF energy from an MRI system to the insulation sheath 146 thereby redirecting the energy so that heat will be dissipated over a larger surface area and away from the interface between the distal tip electrodes 108a, 108b, 110a and 110b and body tissue. There is also heat that is directly dissipated off of the leadwires, which is conductively coupled into the insulation sheath 146. Again, it is desirable that this occur at a location that is spaced from or distant from the therapy delivery electrodes 108a, 108b, 110a and 110b. This can be greatly improved by providing a passive component frequency selective circuit 112 which provided a very low impedance at a selected high frequency or frequencies between each of the associated leadwires and an energy dissipating surface 160. The energy dissipating surface 160 would typically either be a metallic ring or a metallic plate or even a separated metallic surface which has both the property of conducting the high frequency energy and also having a relatively large surface area for dissipating said energy into surrounding body tissues. In a preferred embodiment, the energy dissipating surface 160 would be placed sufficiently far back from the distal electrodes 108a, 108b, 110a and 110b so that in the associated heating of surrounding body tissue would not have any effect on the delicate electrode-to-tissue interface. In addition, by having an energy dissipating surface 160 with a sufficiently large surface area, this will prevent a dangerously large temperature rise as it dissipates energy into the surrounding tissues. By controlling the temperature rise to a small amount, damage to tissue or tissue changes are therefore avoided. The frequency selective reactances 112 are designed to present a very low impedance at selected high frequencies thereby redirecting undesirable high frequency RF energy (in the MHz range) away from the electrodes to the insulating sheath and/or energy dissipating surface 160. In addition, further protection is offered by the optional series frequency selective components 118a, 118b, 120a and 120b. Typically, these can be series inductors or they can be parallel inductor-capacitor bandstop filters in accordance with the present invention (see FIGS. 10-11). Accordingly, substantial protection is provided such that during MRI procedures, the distal electrodes 108a, 108b, 110a, . . . 110$_n$ do not overheat.

Figure 28:
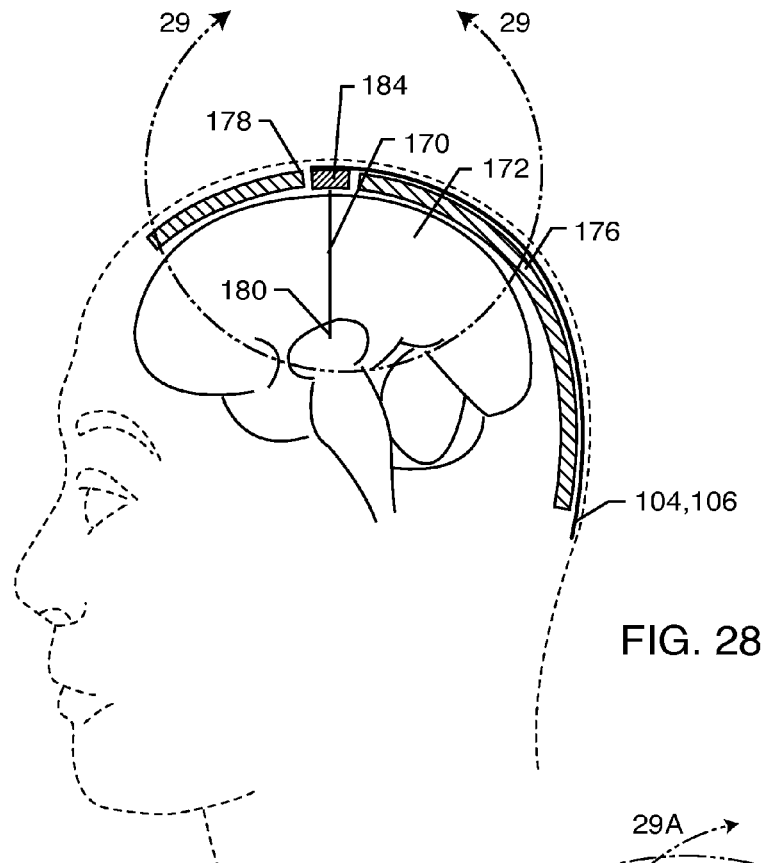
FIG. 28 is a somewhat schematic side view of the human head with a deep brain stimulation electrode shaft assembly implanted therein.

FIG. 28 is taken from FIG. 13 of U.S. 2008/0132987 A1 dated Jun. 5, 2008, the contents of which are incorporated herein by reference. Illustrated is a side view of the human head with a deep brain stimulation electrode shaft assembly 170. At the distal end of the electrode shaft 170 are two distal electrodes 108 and 110 (see FIG. 29) implanted into the patient's brain 172 at a selected implantation site. One or more leadwires 104, 106 (see FIG. 29A) are routed between the skin 174 and the skull 176 down to a pectorally implanted AIMD (pulse generator) which is not shown. Referring back to FIG. 28, one can see that an opening 178 in the skull has been made so that the electrode shaft assembly 170 can be inserted.

Figure 29:
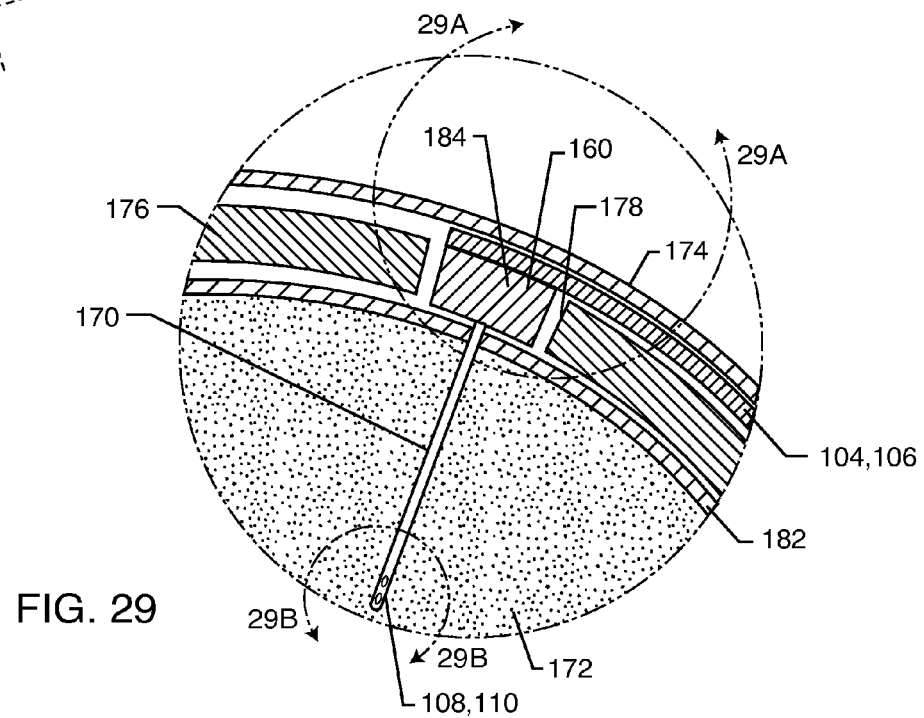
FIG. 29 is an enlarged sectional view corresponding generally with the encircled region 29-29 of FIG. 28.

FIG. 29 is taken generally from section 29-29 in FIG. 28. Shown are bipolar distal electrodes 108 and 110 at the end or tip 180 of the electrode shaft 170. The skull is shown at 176 and the dura is shown as 182. Housing 184 acts as an energy dissipating surface 160 and can be hermetically sealed to protect the passive frequency selective components of the present invention from direct exposure to body fluids.

Figure 29A:
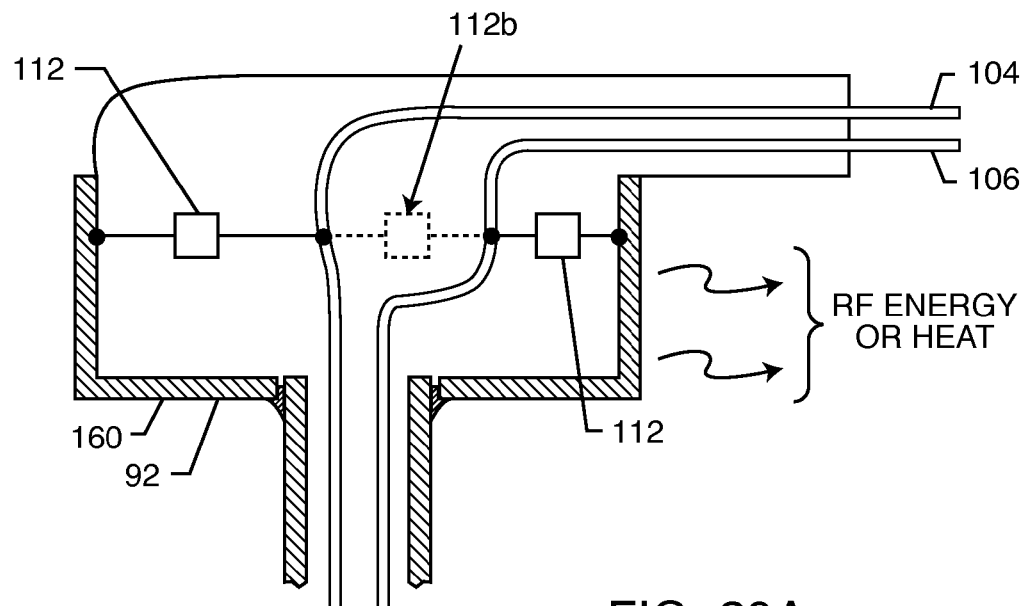
FIG. 29A is a further enlarged and somewhat schematic view corresponding generally with the encircled region 29A-29A of FIG. 29.

FIG. 29A is taken from section 29A-29A of FIG. 29. Shown are frequency selective passive component circuit elements 112 which are generally taken from FIG. 5 or 6. As previously described, these circuit elements 112 could be combined with series reactance elements 118 and 120 as previously illustrated in FIGS. 7, 10 and 11. These have been omitted for clarity, but would generally be placed in series with the leadwires 104 and 106 and placed between frequency selective circuit elements 112 and the distal electrodes 108, 110 (FIG. 20). Referring back to FIG. 29A, circuit elements 112 would divert high frequency RF energy induced from an MR scanner to the energy dissipating surface 160 where it would be dissipated as RF or thermal energy into the area of the skull 176 and/or dura 182. Frequency selective circuit element 112b is also shown connected between the leadwires 104 and 106. This would be effective for any differential mode signals that are present in the leadwires 104 and 106. In accordance with FIG. 4, this would redirect or divert MRI induced RF energy back into leadwires 104 and 106 and away from the distal electrodes 108, 110. This is an example of redirecting RF or thermal energy away from a critical tissue interface point. The skull is considered to be a relatively non-critical or less susceptible type of body tissue to thermal injury. This is in comparison with the very thermally sensitive brain matter into which the distal tip electrodes 108, 110 are implanted. It has been shown that even a temperature rise as small as a few degrees C. can cause damage to sensitive brain matter.

Figure 29B:
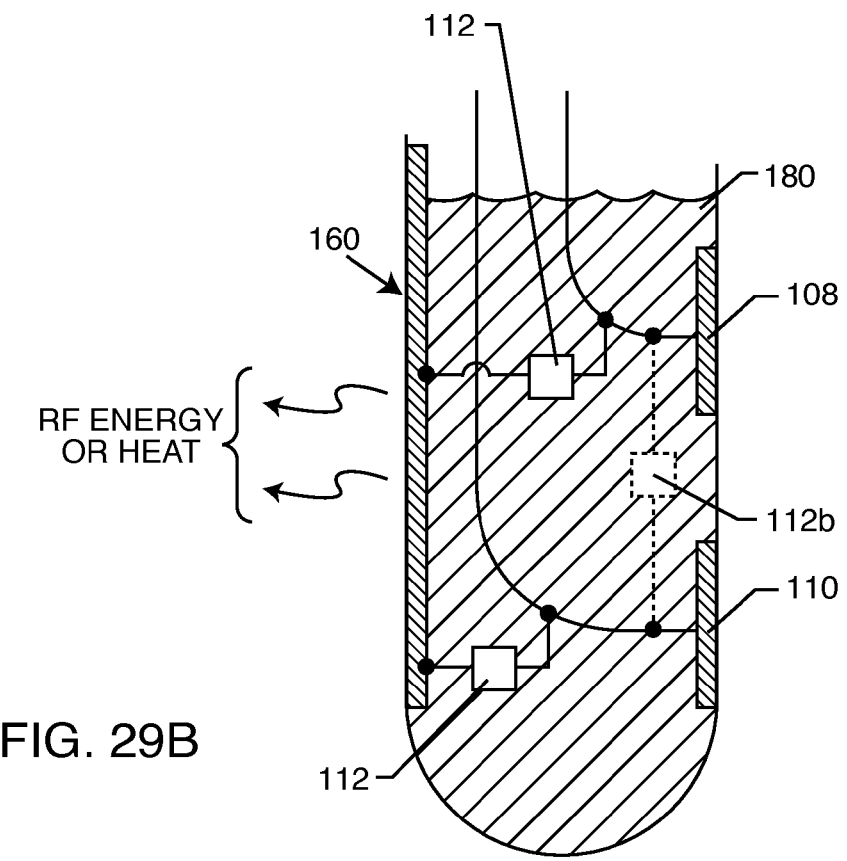
FIG. 29B is an enlarged and somewhat schematic view corresponding generally with the encircled region 29B-29B of FIG. 29.

FIG. 29B is generally taken from area 29B-29B of FIG. 29. Shown are the two bipolar electrodes 108 and 110. The frequency selective elements 112 and 112b have been moved relative to the location shown in FIG. 29A to illustrate one wrong way to approach this particular problem. Specifically, an energy dissipating surface 160 is shown mounted generally at a tip or other distal end portion of the probe shaft 180 in proximity to and/or direct contact with sensitive brain tissue. The frequency selective reactance components 112 and 112b are coupled for redirecting the RF energy from MRI to the energy dissipating surface 160, whereby heat will be dissipated by the energy dissipating surface 160. In the case where it was chosen not to use an energy dissipating surface 160, but simply to rely on the line-to-line frequency selective element 112b, heat would still build-up in the entire distal electrode area and thence be conducted into thermally sensitive brain tissue 172. Accordingly, the placement of the circuit elements as shown in FIG. 29B illustrates a disastrous way to place the frequency selective elements of the present invention. Severe overheating of this distal tip would occur with resulting brain damage. Reference is made to a paper given at the 8$^{th}$ World Congress of the National Neuromodulation Society which was held in conjunction with the 11$^{th}$ Annual Meeting of the North American Neuromodulation Society, Dec. 8-13, 2007, Acapulco, Mexico. This paper was given by Dr. Frank Shellock, Ph. D. and was entitled, MRI ISSUES FOR NEUROMODULATION DEVICES.

Shellock slide 31 shows X-ray views of the placement of deep brain stimulator electrodes into the skull and brain of a human patient. There is also an X-ray view showing the placement of the AIMDs and tunneled leadwires that are associated with the deep brain stimulation electrodes. Slide number 35 shows an extensive thermally induced lesion shown in white with a red arrow to it. This was representative of two patients that inadvertently received MRI wherein their deep brain stimulators overheated and caused extensive thermal injury to the brain. Both patients were severely disabled.

In summary, the configuration as illustrated in FIG. 29A is highly desirable as compared to the configuration as illustrated in FIG. 29B.

Referring once again to the Shellock paper, one can see that the deep brain stimulator involved multiple electrodes. In FIG. 29 one can see that there are only two electrodes 108 and 110. This is a way of illustrating that with real time MRI guidance, the physician can much more accurately place the electrodes into the exact area of the brain, which needs to be electrically stimulated (for example, to control Parkinson's tremor, Turret's Syndrome or the like). What is typically done is that precise MR imaging is performed prior to electrode implantation which is referenced to fiducial marks that's placed on the skin in several locations outside of the patient's skull. The patient's head is first shaved, then these marks are placed and then the MRI is performed. Then when the patient enters the operating room, a fixture is literally screwed to the patient's head at these fiducial marks. This fixture contains a bore into which the various drilling and electrode implanting tools are located. Because of the need for all of this mechanical fixturing, tolerances are involved. This means that by the time the electrodes are implanted in the brain, they may be not in the precise locations as desired. Accordingly, extra electrodes are inserted which involves more leadwires than are really necessary. The patient is usually awake during parts of this procedure wherein the physician will use trial and error to stimulate various electrode pairs until the desired result is achieved. In contrast, the present invention minimizes the need for all these extra electrodes and extra wiring. This is because by eliminating the potential for the distal electrodes to overheat and damage brain tissue, this entire procedure can be done under real time MRI imaging. In other words, the physician can be watching the MRI images in real time as he precisely guides the electrodes to the exact anatomy of the brain that he wishes to stimulate.

FIG. 30 is a hermetically sealed package consisting of a passive distal tip electrode 140 which is designed to be in intimate contact with body tissue, such as inside the right atrium of the heart. A hermetic seal is formed at laser weld 186 as shown between the tip electrode 140 and a metallic ring 188. Gold brazes 190 are used to separate the metallic ring 188 from the energy dissipating surface 160 by use of an intervening insulator 192. This insulator 192 could typically be of alumina ceramic, other types of ceramic, glass, sapphire or the like. The energy dissipating surface 160 is typically gold brazed to the other side of the insulator 192 as shown. An inductor 116, such as an inductor chip in accordance with FIG. 10, is shown connected between the distal tip electrode 140 and a conductive lead 194 which is attached as by laser welds 186b to the end of the leadwire 104 extending through the body to the AIMD. As shown, the lead 194 protrudes through a hermetic seal assembly 196 formed by a metallic flange 198 which is typically of titanium or platinum or the like. The flange 198 is hermetically attached to the lead 194 as by gold brazes 190, and is typically laser welded as shown at 186c to a proximal end of the energy dissipating surface 160.

FIG. 31 is taken generally from the housing of FIG. 30. It is important that the electrical insulating material 192 either be of very low thermal conductivity or have a relatively long length "L" as shown. The reason for this is that the thermal energy that is developed in the energy dissipating surface 160 must not be allowed to reach the distal tip electrode 140 as shown in FIG. 30 where heat could cause damage to the adjacent tissue.

The energy dissipating surface 160 is typically of biocompatible metals, such as titanium, platinum or the like. It is important that the energy dissipating surface be both electrically conductive and thermally conductive so that it can transfer RF and thermal energy into body fluid or tissue. The energy dissipating surface 160 can be roughened or even corrugated or bellowed as shown in FIG. 31A to increase its surface area and therefore its energy dissipating properties into surrounding body fluids or body tissue.

In accordance with FIG. 5, capacitive elements 114a and 114b shown in FIG. 30 are designed to act as a low impedance at higher frequencies. Electrical connections 200a and 200b (FIG. 30) couple the capacitor 114a to the energy dissipating surface 160, whereas electrical connections 200c and 200d couple the capacitor 114b to the energy dissipating surface 160. This forms a broad band low pass filter wherein the inductor 116 acts in cooperation with the capacitive elements 114a and 114b. The presence of the inductor element 116 is not required; however, it does enhance the performance of the capacitor elements 114a and 114b. Capacitor elements 114a and 114b are typical off-the-shelf commercial monolithic ceramic capacitors (MLCCs). These are better illustrated in FIG. 33A.

There is an advantage in the present invention in using a capacitor for the selective frequency element 112 as shown in FIG. 5. The capacitor tends to act as a broadband filter which will attenuate a range of MRI frequencies. For example, placement of an effective capacitor 112 could attenuate 64 megahertz, 128 megahertz and higher MRI frequencies. However, if one were to use an L-C series trap filter as shown in FIG. 6 for the variable frequency element 112, then this would only be effective at one MRI frequency, for example, 64 megahertz only. Of course, as already been disclosed herein, one could use multiple L-C trap filters. However, in a preferred embodiment the use of a capacitor as illustrated in FIG. 5 is desirable because with a single component, one can attenuate a broad range of MRI frequencies.

The schematic diagram for the circuitry of FIG. 30 is shown in FIG. 32. Capacitors 114a and 114b are actually in parallel and act as a single capacitive element. The reason for multiple capacitors is to obtain a high enough total capacitance value so that the capacitive reactance is very low at the frequency of interest (for example, 64 MHz for a 1.5 T MR system).

An alternative capacitor 114c for use in the circuit of FIG. 32 is known as a unipolar feedthrough capacitor is shown in FIG. 33B. It has outside diameter and inside diameter termination surfaces 202 and 204 for electrical contact. Feedthrough capacitors can be unipolar or multipolar. These are completely described in the prior art; for example, refer to U.S. Pat. No. 7,363,090, particularly FIGS. 3, 5, 29 through 31, and 39. See also U.S. Pat. Nos. 4,424,551; 5,333,095; and 6,765,779.

Figure 34:
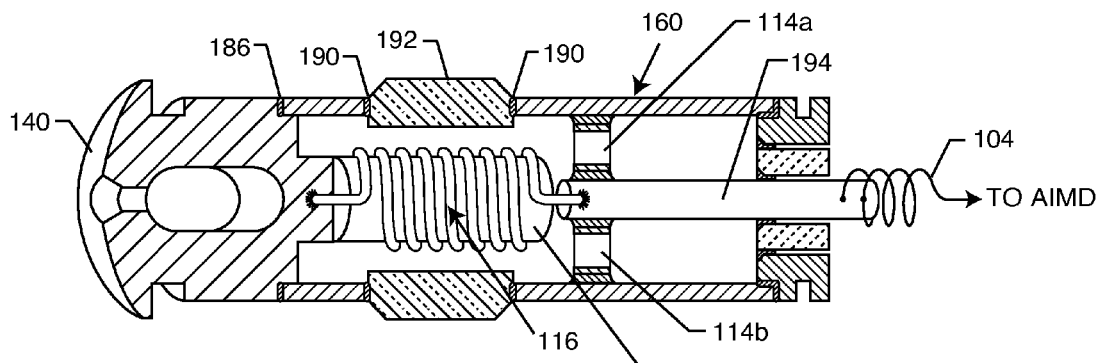
FIG. 34 is a sectional view similar to FIG. 30 and depicts an alternative embodiment wherein an inductor element is wound or printed about a central mandrel.
Figure 46:
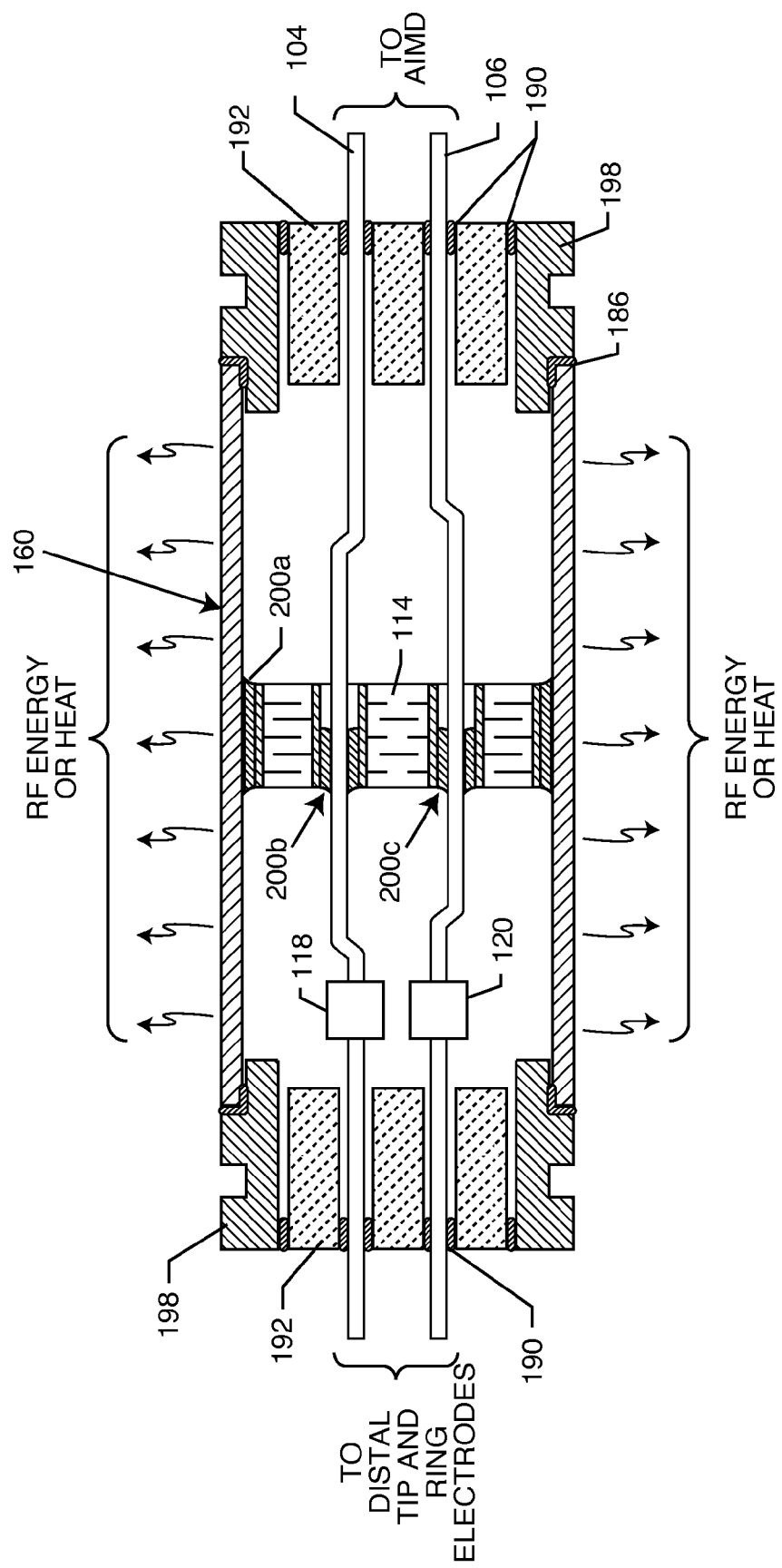
FIG. 46 is an enlarged and somewhat schematic sectional view taken generally on the line 46-46 of FIG. 45.

FIG. 34 is similar to FIG. 30 (using common reference symbols) except that the inductor element 116 is wire wound around a non-ferromagnetic mandrel 206 (formed from a material such as a ceramic or plastic). This type of wound inductor 116 has much higher current handling capability as compared to the inductor chip of FIG. 30. The inductor chip of FIG. 30 can be fabricated from a variety of shapes including Wheeler's spirals and the like. Refer to U.S. Patent Publication No. 2007-0112398 A1, FIG. 83. A Wheeler's spiral is illustrated in FIGS. 42 and 43 of U.S. Patent Application No. 60/767,484. A composite inductor is illustrated in FIG. 46 of U.S. Patent Application No. 60/767,484. Also refer to FIGS. 70 and 71 of U.S. Patent Application No. 61/038,382. These inductors can be manufactured by a number of printing techniques including lithographic or copper clouting and etching. However, this results in relatively thin and high resistivity inductor traces.

It is important that the inductor element 116 of the present invention be able to handle substantially high currents when it is in series with the lead 194. The reason for this has to do with either ICD applications for shock electrodes or automatic external defibrillation (AED) events. AEDs have become very popular in government buildings, hospitals, hotels, and many other public places. When the external defibrillator paddles are placed over the chest of a cardiac pacemaker patient, the high voltage that propagates through body tissue can induce powerful currents in implanted leads. Accordingly, the inductor 116 of the present invention has to be designed to handle fairly high current (as high as the 4 to 8 amp range in short bursts). The wire wound inductor 116 of FIG. 34 has wire of a larger cross-sectional area and is therefore a higher current handling inductor and is therefore a preferred embodiment.

Figure 35:
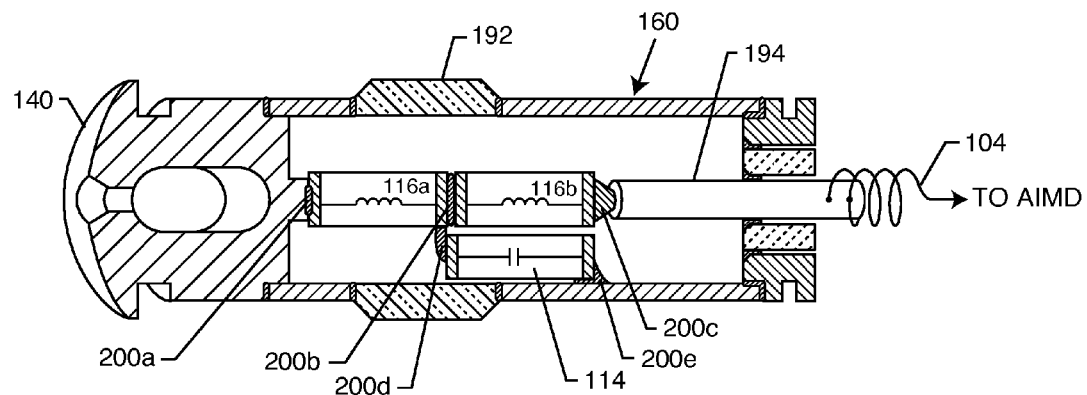
FIG. 35 is a sectional view similar to FIGS. 30 and 34, but illustrates a further alternative embodiment of the invention with alternative means for decoupling signals from a leadwire to an energy dissipating surface.

FIG. 35 illustrates an entirely different approach for the diverting of RF energy away from the electrode tip 140 to the energy dissipation surface 160. Shown are electrical connections 200a, 200b between a first inductor 116a and the distal tip electrode assembly 140. The other end of the first inductor 116a is connected to a second inductor 116b which is in turn electrically connected at 200c to the leadwire 194. The capacitor 114 is connected between the junction of the two inductors 116a and 116b at electrical connection 200d. The other end of the capacitor is electrically connected at 200e to the energy dissipating surface 160. An insulating sleeve (not shown) can be used to ensure that the capacitor termination and electrical connection 200d does not inadvertently make contact (short out) with the energy dissipating surface 160. As shown, this connection is made adjacent to the insulator 192 so there is no chance for such shorting out.

Figure 36:
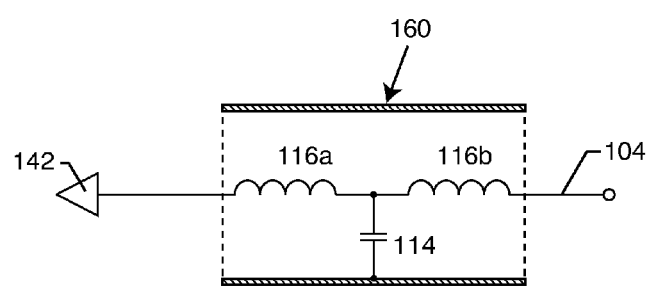
FIG. 36 is a schematic circuit diagram corresponding with the sealed electrode assembly of FIG. 35.

The electrical schematic for FIG. 35 is shown in FIG. 36. In accordance with FIG. 7, this forms what is known in the art as a low pass filter (in this example, a T filter), which tends to enhance the filtering performance by directing more of the RF energy to the energy dissipating surface 160. As previously mentioned, a single or multi-element low pass filter would attenuate a broad range of MRI frequencies and would be an advantage in the present invention for that reason.

Figure 37:
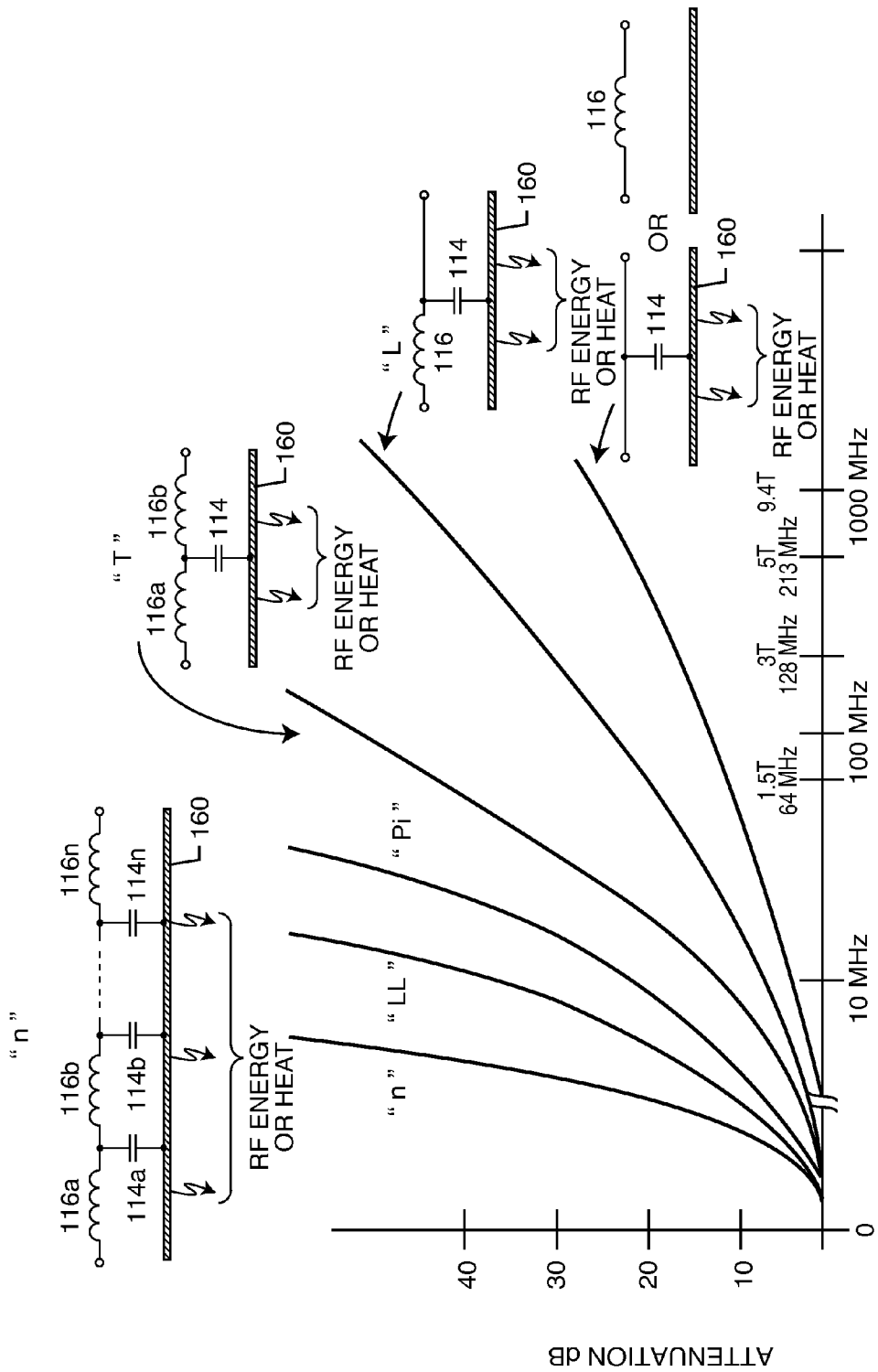
FIG. 37 is an attenuation versus frequency chart for various types of low pass filters.
Figure 38:
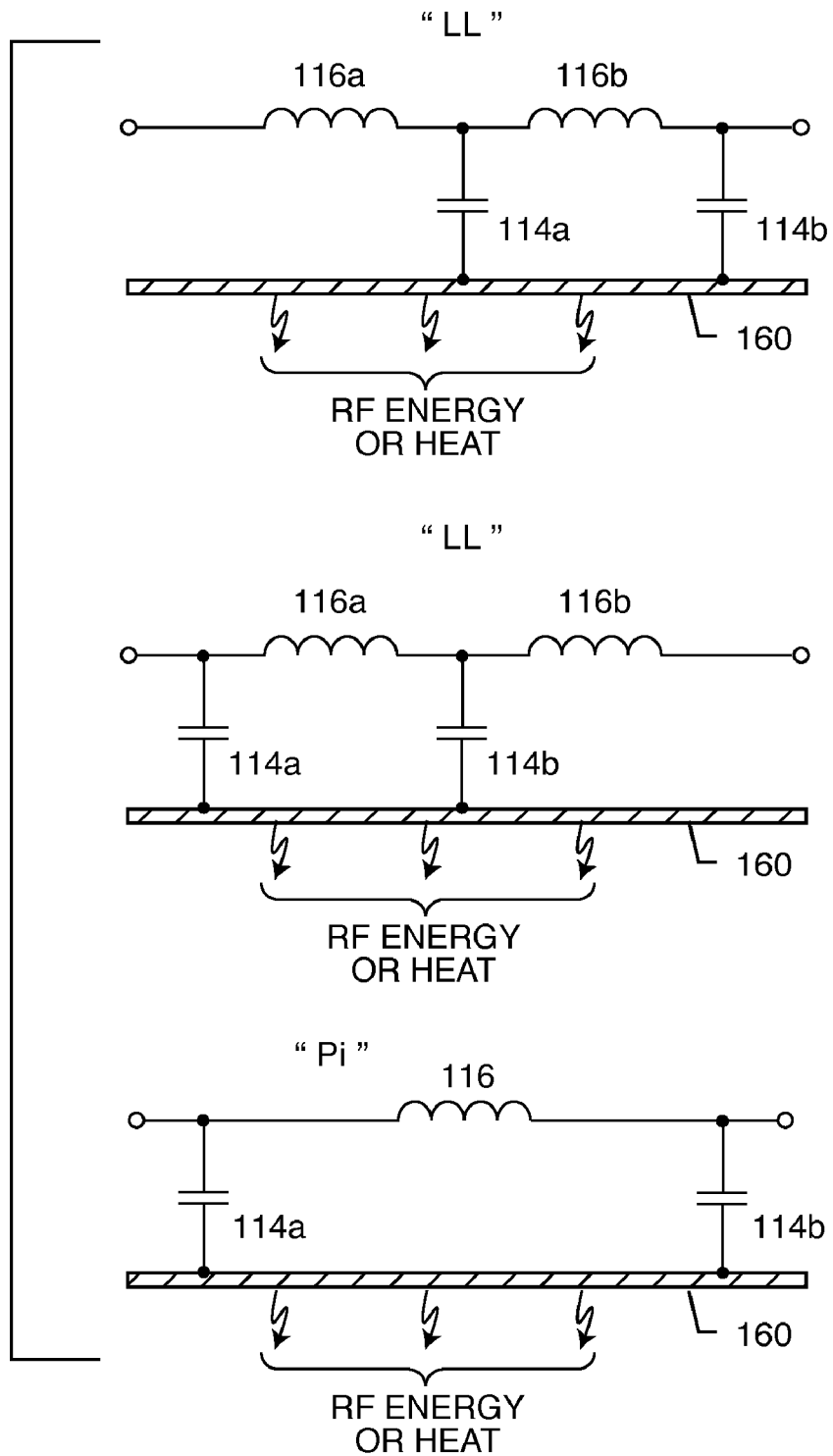
FIG. 38 shows schematic circuit diagrams for different types of low pass filters charted in FIG. 37.

The various types of low pass filters are more thoroughly shown in FIGS. 37 and 38 which compares the filtering efficiency measured as attenuation in dB with increasing numbers of filter elements. Shown are a single element low pass filter consisting of the capacitor 114 or an inductor 116, an L filter which consists of an inductor 116 and a capacitor 114, a T filter as shown in FIGS. 35-37, a Pi filter (FIG. 38), an LL filter (FIG. 38) or an "n" element filter (FIG. 37). FIG. 37 shows the general response curves of these types of filters in attenuation versus frequency. The schematics for these various filters, which are correlated to the curves in FIG. 37, are shown on FIG. 38. As one increases the number of filter elements, the ability to attenuate or block high frequency signals from reaching a distal electrode is improved. Referring once again to FIG. 37, for example, one can see, that for a particular value of a single element capacitive filter, the attenuation for a 1.5 Tesla MRI system operating at 64 MHz is only about 12 dB. This means that a certain amount of the RF energy would still reach the distal tip electrode. Now compare this to the T filter of FIGS. 35-37, where one can see that there is in excess of 45 dB of attenuation. In this case, an insignificant amount of RF energy from the RF pulsed frequency of the MRI, would reach the distal electrode. Accordingly, one preferred embodiment of the present invention is that a capacitor combined with one or more inductors would be an optimal configuration. As the number of elements increases, the filtering efficiency improves. When the filtering efficiency improves, this means that less and less RF energy will reach the distal tip.

Figures 39, 39A:
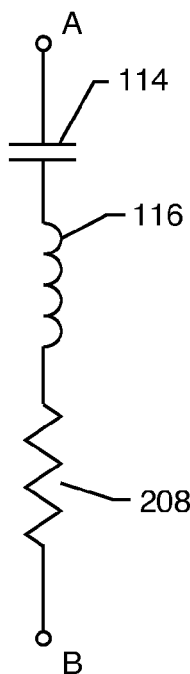
FIG. 39 is a schematic circuit diagram illustrating an L-C trap filter.
FIG. 39A depicts a resonant frequency equation for the L-C trap filter of FIG. 39.

FIG. 39 illustrates a schematic diagram of a series inductor 116-capacitor 114 filter which is commonly known in the industry as a trap filter. The trap filter was previously described in connection with FIG. 6. Referring once again to FIG. 39, there is a particular frequency for a trap filter when the capacitive reactance becomes equal and opposite to the inductive reactance. At this single frequency, the capacitive reactance and the inductive reactance cancel each other out to zero. At this point, all one has left is the residual resistance 208. If one selects high quality factor (Q) components, meaning that they are very low in resistance, then the trap filter of FIG. 39 ideally tends to look like a short circuit at its resonant frequency $F_r$ between points A and B which may comprises connections respectively to a pair of leadwires 104 and 106. FIG. 39A gives the resonant frequency equation where $F_r$, in this case, was measured in hertz. FIG. 9 shows the effect of a short circuit 122 between leadwires 104 and 106. Referring once again to FIG. 39, it is important that the amount of resistance R be controlled. This is better understood by referring to FIG. 40.

Figure 40:
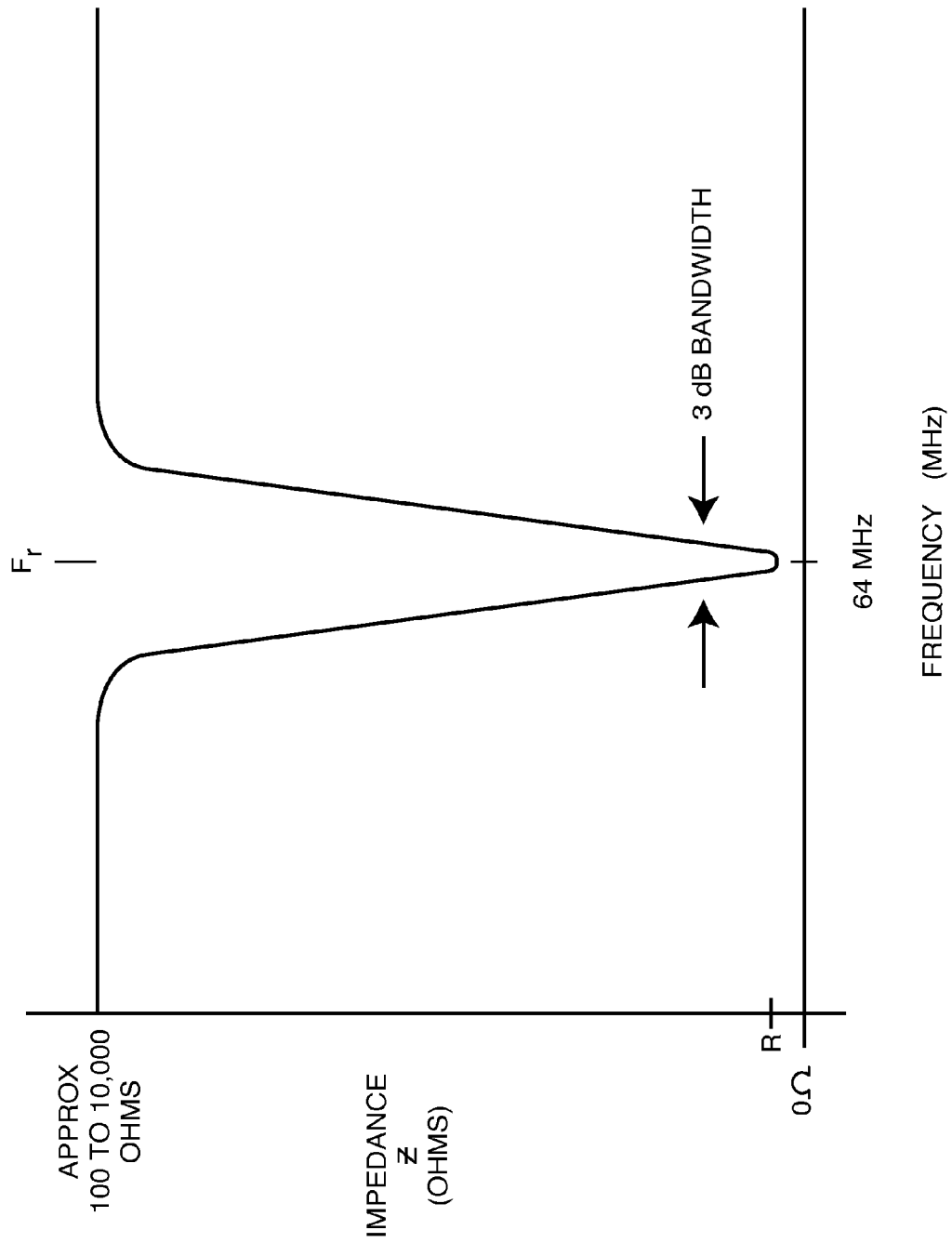
FIG. 40 is an impedance versus frequency chart for the L-C trap filter of FIG. 39.

FIG. 40 illustrates the impedance Z in ohms versus frequency of the series resonant L-C trap filter of FIG. 39. As one can see, the impedance is quite high until one reaches the frequency of resonance $F_r$. At this point, the impedance of the series L-C trap goes very low (nearly zero ohms). For frequencies above or below resonance $F_r$, depending on the selection of component values and their quality factor (Q), the impedance can be as high as 100 to 1000 or even 10,000 ohms or greater. At resonance, the impedance tries to go to zero and is limited only be the amount of parasitic resistance 138 (FIG. 39) that is generally composed of resistance from the inductor 116 and also the equivalent series resistance from the electrode plates of the capacitor 114. There is a trade off in proper selection of the components that controls what is known as the 3 dB bandwidth. If the resistance is extremely small, then the 3 dB bandwidth will be narrower. However, this makes the trap filter more difficult to manufacture. Accordingly, the 3 dB bandwidth and the resistive element R are preferably selected so that it is convenient to manufacture the filter and tune it to, for example, 64 MHz while at the same time providing a very low impedance R at the resonant frequency. For an ideal L-C series resonant trap filter, wherein ideal would mean that the resistance R would be zero, then the impedance at resonance would be zero ohms. However, in this case, the 3 dB bandwidth would be so narrow that it would be nearly impossible to manufacture. Accordingly, some amount of resistance R is in fact desirable.

As previously mentioned, there is a disadvantage to use of the L-C trap filter as shown in FIG. 6. That is, it is really only effective for attenuating the one MRI frequency (for example, 64 megahertz for a 1.5 megahertz scanner). Accordingly, when the AIMD manufacturer would apply for their FDA conditional labeling, they could only claim compliance with 1.5 Tesla MRI scanners. However, the L-C trap filter of FIG. 6 also offers a very important advantage in that it offers a very high degree of attenuation at this one selected frequency and is also highly volumetrically efficient. Accordingly, there is a trade-off here. When one uses a broadband low pass filter, a broad range of frequencies is attenuated at the cost of increased size and complexity (an additional number of components). An L-C trap filter such as shown in FIG. 6 is more of a "rifle-shot" approach wherein only one selected frequency is attenuated. In physics, this is more efficient and tends to make the components smaller.

FIG. 41 illustrates yet another method of decoupling RF signals from leadwire 104. Referring back to FIGS. 30 through 38, all of the aforementioned decoupling techniques involve broad band low pass filtering. The advantage with these is that they would be applicable to a wide range of MRI machines including 0.5, 1.5, 3.0, 5.4 Tesla and so on. In other words, these broad band EMI filters would attenuate a broad range of RF frequencies. In FIG. 41, one can see that there are two discrete L-C trap filters. The first trap filter consists of inductor 116a and capacitor 114a acting in series, and the second trap filter consists of inductor 116b and capacitor 114b operating in series. This is best understood by referring to the schematic of FIG. 42 which shows the series connection of 116a, 114a from the lead 194 to the energy dissipating surface 160. Inductor 116b and capacitor 114b are also connected in series from the lead 194 to the energy dissipating surface 160.

In FIG. 41, one can see that an electrical connection 200a is made between the distal tip electrode 140 and inductor chip 116a. Inductor chip 116a is then electrically connected via electrical connection material 200b to monolithic chip capacitor (MLCC) capacitor 114a. The other end of the chip capacitor 114a is electrically connected at 200c to the energy dissipating surface 160. Inductor 116b is also connected to the distal tip electrode 140 by material 200d. The other end of inductor 116b is connected in series at 200e with capacitor 114b. The other end of capacitor 114b is electrically connected at 200f to the energy dissipating surface 160. In this way, the two trap filters are connected in parallel between the lead 194 and the energy dissipating surface 160 as shown in the schematic diagram of FIG. 42.

FIG. 43A illustrates a typical chip inductor 116a, 116b which can be used in FIG. 41.

FIG. 43B is a typical prior art MLCC chip capacitor 114a, 114b which can also be used in conjunction with the package shown in FIG. 41.

Figure 44:
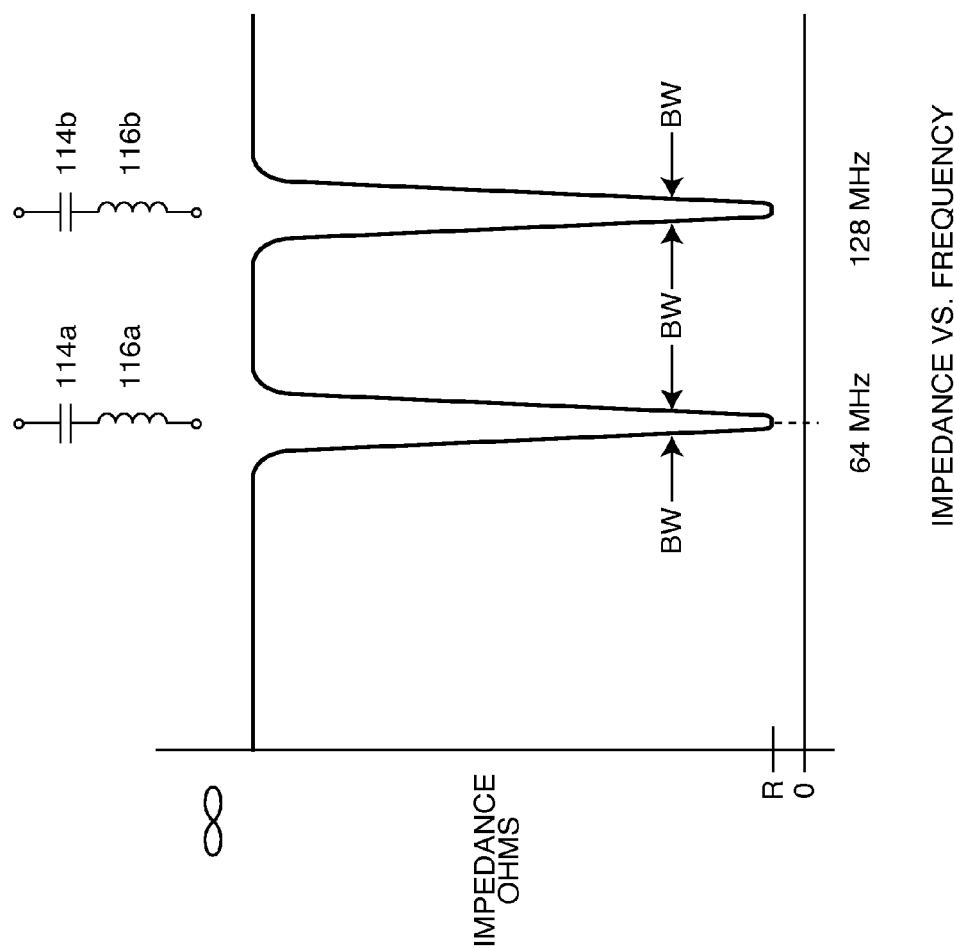
FIG. 44 is an impedance versus frequency chart for the dual L-C trap filter embodiment of FIG. 41.

FIG. 44 is a graph of impedance versus frequency showing the impedance in ohms for the L-C trap filter elements that were previously described in FIGS. 41 and 42. By carefully selecting the component values 114a and 116a and also 114b and 116b, one can select the frequencies at which the two (or more) L-C trap filters will self-resonate. In the present example, the first trap filter including components 114a and 116b has been selected to resonate at 64 MHz, and the second trap filter including element 114b and 116b has been selected to resonate at 128 MHz.

Referring once again to FIG. 44, one can see that we now effectively have dual trap filters which tend to short out leadwire 194, 104 at two different frequencies. In this case, by example, the first trap filter resonates at 64 MHz, which is the RF pulsed frequency of a 1.5 Tesla MRI system. The second trap filter, which has resonant frequency $F_{r2}$ at 128 MHz, is designed to attenuate the RF pulsed signals from a 3 Tesla MRI frequency. It will be appreciated that a multiplicity of trap filters can be used depending on how many different types of MRI systems that one wants to have compatibility with for an implanted lead and electrode. The method of selecting the resonant frequency was already described in FIG. 39A and is applicable to FIG. 44. Referring once again to FIG. 44, one will note that except at the resonant frequency $F_{r1}$ and $F_{r2}$, the impedance of the trap filter is very high. This is very important so that low frequencies are not attenuated. Accordingly, using a cardiac pacemaker application as an example, pacing pulses would be free to pass and also low frequency biologic signals, such as those that are produced by the heart. It is very important that pacemaker sensing and pacemaker pacing can occur while at the same time, high frequency energy, for example, that from the RF pulsed frequency of an MR system can be diverted to an appropriate energy dissipating surface 160.

Figure 45:
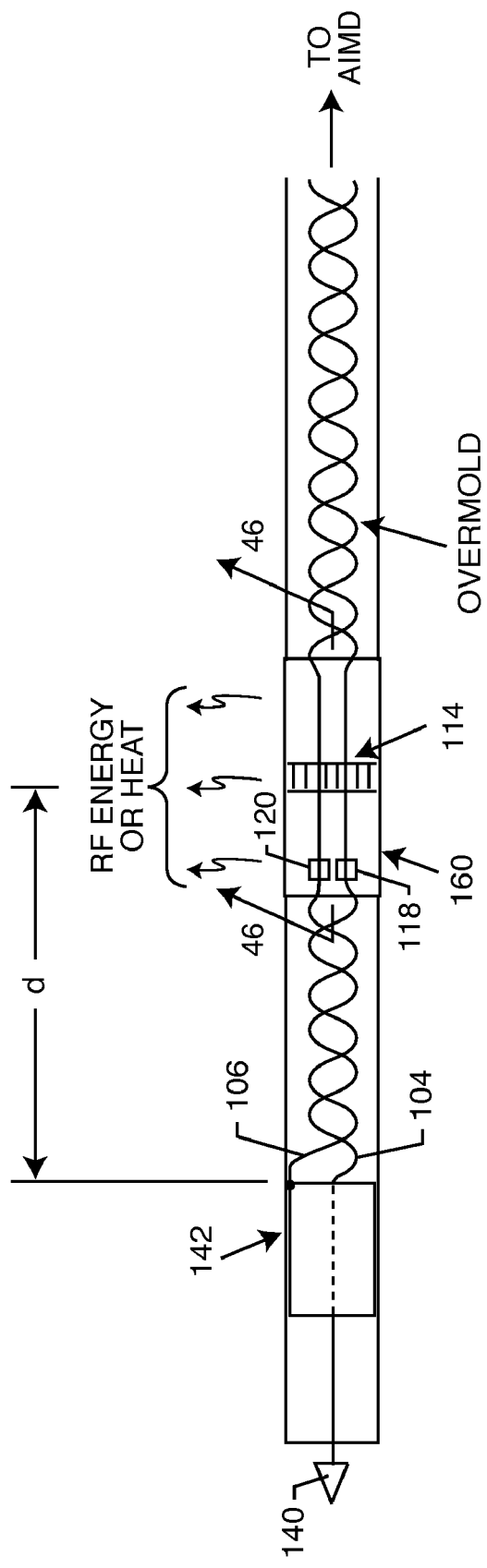
FIG. 45 is a schematic representation of an implantable medical device bipolar leadwire system.

FIG. 45 illustrates a typical active implantable medical device bipolar leadwire system. On the left is shown a distal tip electrode 140 and a distal ring electrode 142. The energy dissipating surface 160 of the present invention is shown along with coaxial leadwires 104 and 106 which would be connected to the AIMD. These could be endocardial or epicardial in accordance with the prior art.

FIG. 46 is a blown up sectional view generally taken from section 46-46 from FIG. 45. In FIG. 46, one can see that there is an energy dissipating surface 160 which is enclosed at both ends by two hermetic seal flanges or flange assemblies each consisting of a flange 198, an insulator 192 and gold brazes 190. This is designed to be laser welded as at 186 into the metallic energy dissipating surface 160 as shown. A bipolar feedthrough capacitor 114 is shown in cross-section in FIG. 46 where the two leadwires 104 and 106 pass through it. The feedthrough capacitor 114 is a very efficient broad band filter which would tend to decouple high frequency signals such as 64 MHz (1.5 Tesla) and 128 MHz (3 Tesla) from the leadwires 104, 106 to the energy dissipating surface 160 in accordance with the present invention. Each leadwire 104 and 106 may additionally include the frequency selective reactances 118 and 120 (as previously shown and described in FIGS. 7, 10 and 11).

Figure 47:
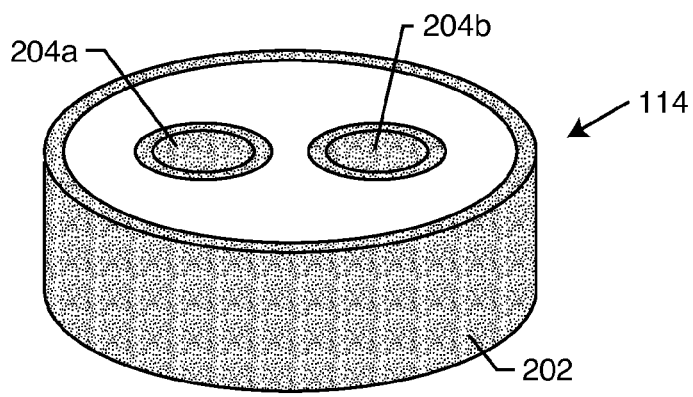
FIG. 47 is an isometric view of a bipolar feedthrough capacitor for use in the device of FIGS. 45-56.

The bipolar feedthrough capacitor 114 is illustrated in isometric view in FIG. 47. Shown is an outside diameter termination surface 202 which is electrically and thermally connected to the inside diameter of the energy dissipating surface 160 of FIG. 42, as by electrical connection 200a (FIG. 46). Also shown, are inside termination surfaces 204a and 204b located on the inside diameter of two feedthrough capacitor ID holes for electrical connection at 200b and 200c (FIG. 46) between leadwires 104 and 106, respectively to the feedthrough capacitor termination surfaces 204a and 204b, respectively. The use of a feedthrough capacitor in this case makes for a truly broadband performance. As MR systems continue to evolve in their static magnetic field strength, the RF pulse frequencies go higher and higher. For example, for a 10 Tesla scanner, the RF pulse frequency is 426.5 megahertz. Prior art MLCC chip capacitors have internal inductance and tend to self-resonate at frequencies around 400 megahertz or above. Accordingly, the use of a feedthrough capacitor accommodates much higher frequency MRI systems.

Figure 64:
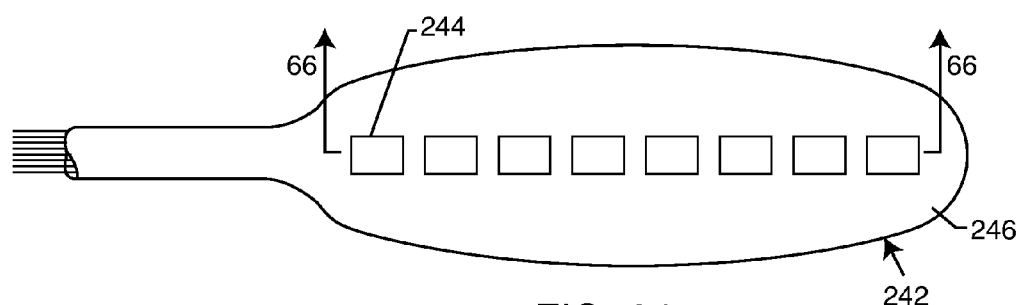
FIG. 64 is a fragmented top plan view of an exemplary paddle electrode embodying the present invention.
Figure 65:
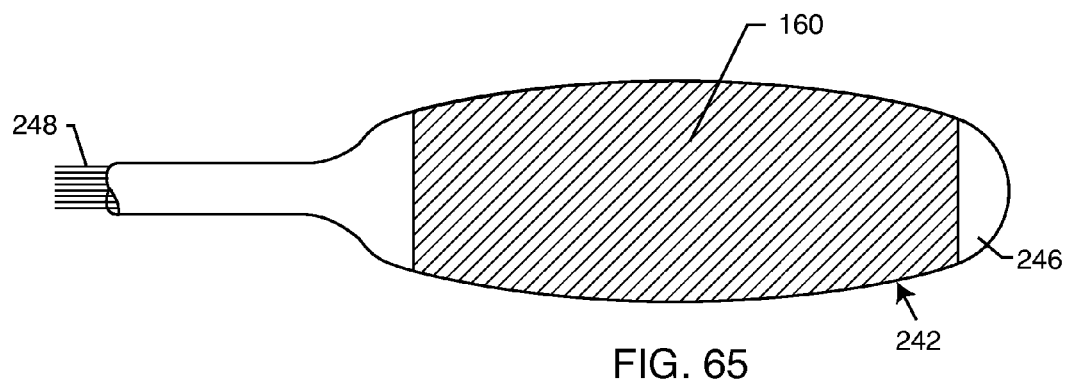
FIG. 65 is a bottom plan view of the paddle electrode shown in FIG. 64.
Figure 66:
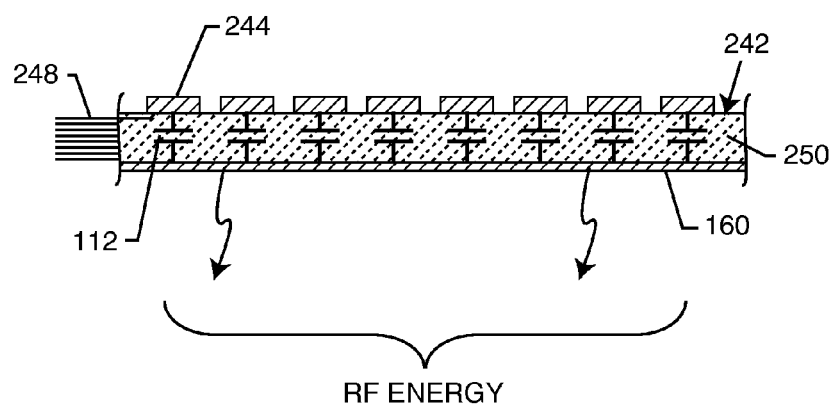
FIG. 66 is an enlarged sectional view taken generally along the line 66-66 in FIG. 64.

Referring once again to FIG. 26 and FIG. 29, one can understand why the energy dissipating surface 160 of FIG. 45 has been moved back a suitable distance "d" from the distal tip electrode 140 and the distal ring electrode 142. This is because of the tendency for distal tip 140 and ring electrodes 142 to become completely embedded or encapsulated with body tissue. In other words, one cannot guarantee that the distal ring electrode 142 will always be freely floating in the blood pool, for example, of the right ventricle or the right atrium. Referring once again to FIG. 25, one can see shaded areas where tissue encapsulation tends to be the greatest. An ideal location for the energy dissipating surface 160, as described in FIG. 45, is shown as 160a in FIG. 25. This guarantees that the energy dissipating surface is placed generally into the area of the right ventricle that is free of trabecula tissue and where there is always freely flowing blood. Of course, this is particularly important for cardiac rhythm management applications wherein pacemakers and implantable defibrillators are commonly used. For implantable neurostimulators, generally, these are not placed in areas where there is freely flowing blood. However, it is still important in these cases that the energy dissipating surface 160 be a sufficiently large enough distance from the associated electrode(s) so that if there is adjacent tissue heating, it does not affect the delicate interface between the electrodes and surrounding body tissue. This would be particularly important, for example, in a deep brain stimulator. As shown in FIG. 29, for example, an ideal location for the energy dissipating surface 160 would be either at the skull or subdural (slightly below the skull). In this case, the deep brain stimulation electrode would protrude down into the brain tissue below the energy dissipating surface 160. In this case, the RF energy and/or heat would be dissipated over a relatively large surface area well away from the very heat sensitive and delicate brain tissues 172. For a spinal cord stimulator, there is generally freely flowing spinal fluid which can act as a cooling agent as well. In this case, it is desirable to have the EDS surface 160, again, spaced at some distance from the therapy delivery electrode such that cooling effectively takes place within the cerebral spinal fluid. See U.S. Publication Nos. US 2008-0132987 A1 and US 2007-0112398 A1, which are incorporated by reference herein. In some cases, the separation distance can be quite small, for example on the opposite surface of a paddle electrode as shown in FIGS. 64, 65 and 66.

Figure 48:
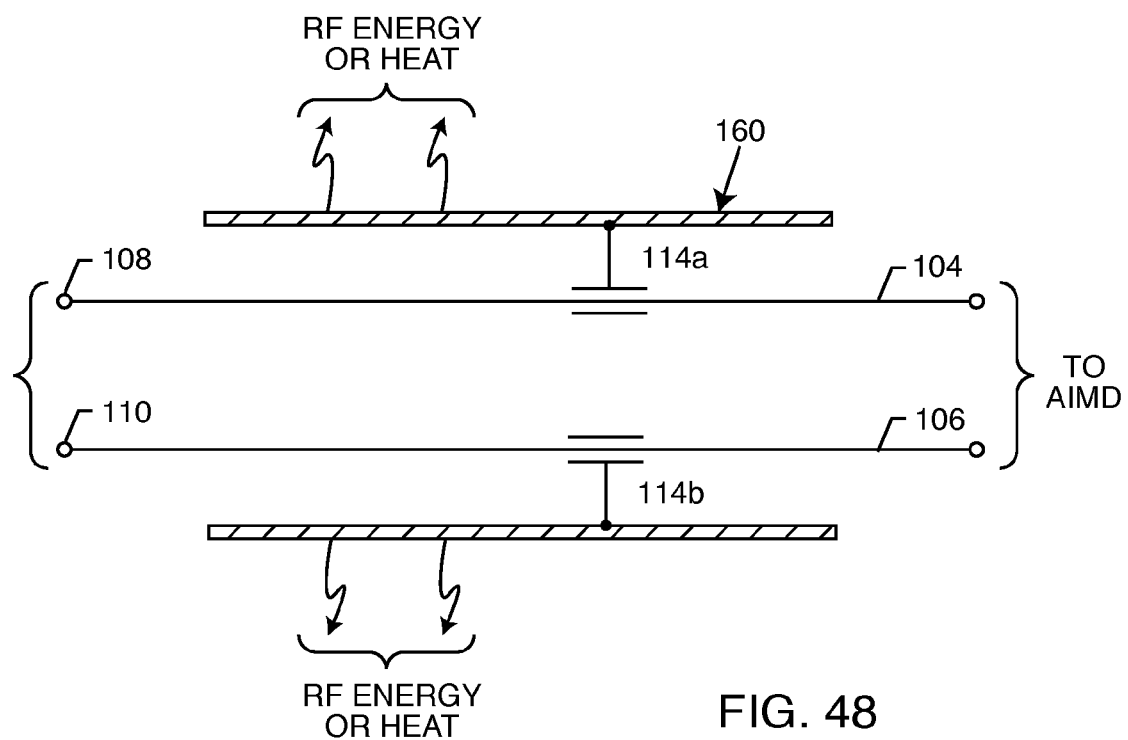
FIG. 48 is a schematic circuit diagram corresponding with the embodiment shown in FIGS. 45-46.

FIG. 48 is a schematic diagram of the energy dissipating surface 160 assembly previously described in FIGS. 45 and 46. From FIG. 48, one can see that the passive frequency selective elements 114a and 114b could be replaced by any of the circuits previously described in FIGS. 4 through 11 as element 112.

Figure 49:
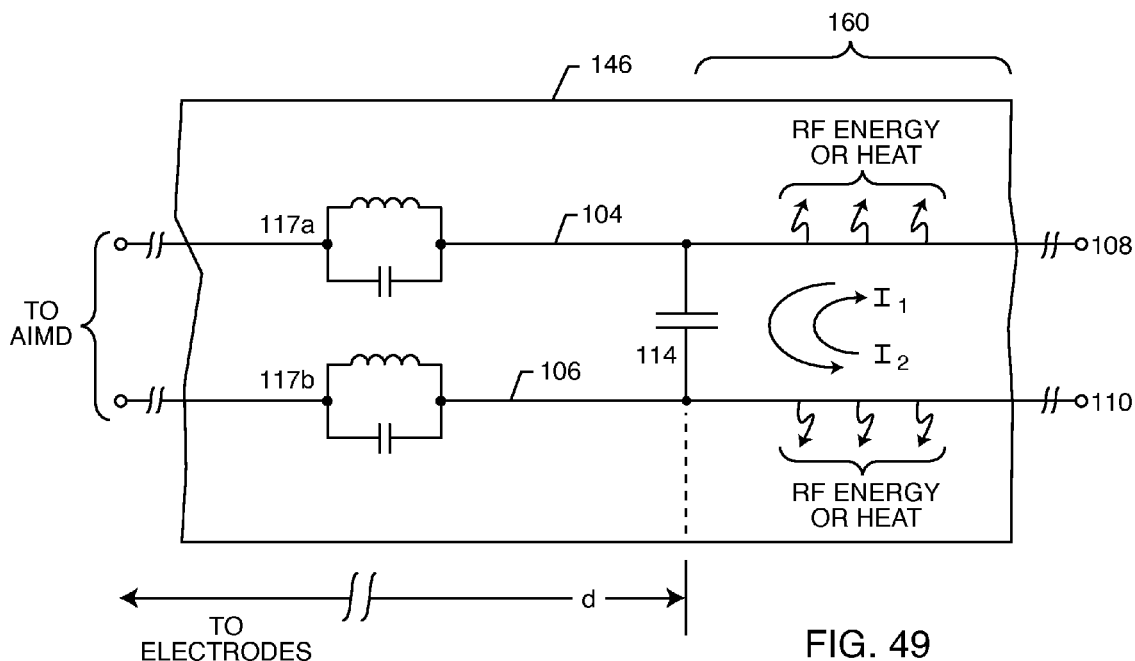
FIG. 49 is a schematic circuit diagram illustrating a bipolar lead assembly with distal tip and ring electrodes shown at a suitable distance from an energy dissipation surface (EDS)

FIG. 49 illustrates a bipolar lead of the present invention with distal tip and ring electrodes 108, 110 shown distally at a suitable distance d from a energy dissipation surface 160 such that energy dissipation in the 160 would not cause a temperature rise at the distal electrodes. Shown is a capacitor 114 connected between the leadwires 104 and 106. Also shown are a pair of bandstop filters 117a and 117b as previously illustrated in FIG. 11. In fact, the passive component network configuration of FIG. 49 is identical to that previously illustrated in FIG. 11, wherein the frequency selective element 112 is a capacitor 114. Referring once again to FIG. 49, one can see that the capacitor element 114 acts as a high frequency energy diverter. This works in cooperation with the two bandstop filter elements 117a and 117b which act as energy impeders at a selected MRI frequency. Accordingly, high frequency energy that is induced on the leadwires 104 and 106 is converted to RF circulation currents $I_1$ and $I_2$. $I_1$ and $I_2$ are shown in opposite directions to illustrate, for example, for a 1.5 Tesla MRI system, that these oscillate back at 64 million times per second. This creates a great deal of current in the associated leadwires to the right (as viewed in FIG. 49) of the diverting element 114. This causes heat to be dissipated in the leadwires 104 and 106 into the energy dissipating surface 160 such as the overall insulation sheath or shield of the probe, catheter or implanted device as shown.

Figure 50:
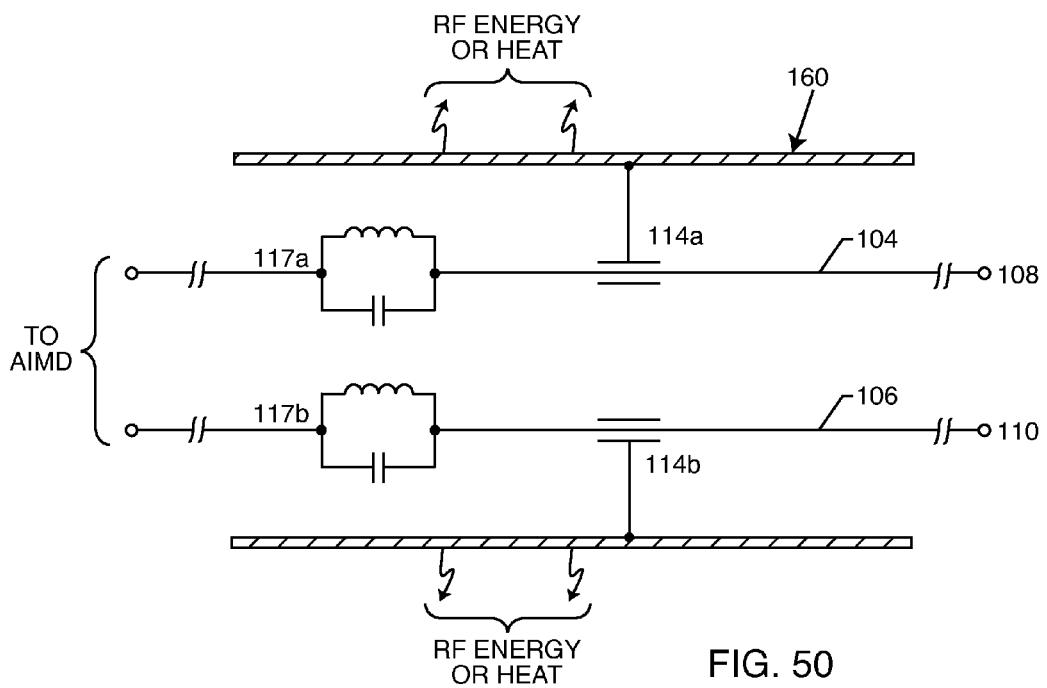
FIG. 50 is a schematic circuit diagram similar to FIG. 49, except that a pair of capacitors are used.

FIG. 50 is very similar to FIG. 49 except that diverting element 114 had been replaced by a pair of capacitor elements 114a and 114b which connect from leadwires 104 and 106 respectively to an electromagnetic shield or an energy dissipating surface 160. It is a desirable property of the present invention that the EDS surface 160 be highly thermally conductive, have relatively high surface area for efficient transfer of RF or heat energy into surrounding fluids and body tissue and also be electrically conductive at RF frequencies.

The bandstop filters 117a and 117b of FIG. 50 look like a very high impedance (ideally an infinite impedance) at the resonant frequency. This has the effect of disconnecting the distal electrodes at these high frequencies from the leadwires 104 and 106. These work in conjunction with the low pass filter elements 114a and 114b which act as a way to divert the high frequency energy to the energy dissipating surface 160. As previously mentioned, the low pass filter elements 114a and 114b can consist of any of the low pass filters as previously described in FIGS. 37 and 38 or the L-C trap filter as previously described in FIGS. 39, 39A, 40, 41 and 44. A high frequency model of FIG. 50 is illustrated in FIG. 9 wherein the leadwires are effectively shorted together to an energy dissipating surface 160 and the distal electrodes 108 and 110 have been effectively disconnected (in this case, by the bandstop filter elements) from the electrodes. For a more complete description of bandstop filter elements and their design and operation, refer to U.S. Pat. No. 7,363,090.

Figure 51:
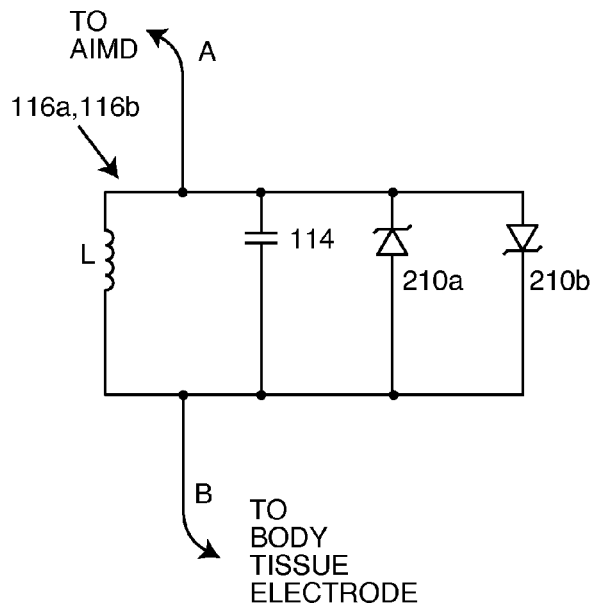
FIG. 51 is a schematic circuit diagram illustrating a band stop filter modified to include a pair of diodes in a parallel or back-to-back configuration.

FIG. 51 illustrates an exemplary energy diverter (as previously shown described in connection with FIGS. 4, 5 and 6) comprising, for example, a capacitor 114 (as previously shown and described herein) with nonlinear circuit elements such as diodes 210a and 210b placed in parallel therewith. These diodes 210a, 210b are oriented in what is known in the prior art as a back-to-back configuration. Nonlinear circuit elements (such as diodes) can allow the device to be "switched" between different modes of operation. The diode elements 210a, 210b, as illustrated in FIG. 51, can be placed in parallel with each other, and with any of the frequency selective circuit elements shown in FIGS. 4 through 11. For example, referring to FIG. 5, the diode elements 210a and 210b could be placed in parallel with the capacitive element 114. Referring to FIG. 10, two diode elements 210a, 210b could also be placed in parallel with each of the inductor elements 116a and 116b. As previously discussed, automatic external defibrillators (AEDs) have become very popular in the patient environment. Accordingly, implanted leads must be able to withstand very high pulsed currents. These pulse currents can range anywhere from 1 to 8 amps. The passive frequency selective components used in accordance with the present invention are typically very small in size. In order for an inductor element L to be able to handle 1 to 8 amps, it would have to be exceedingly large. However, by using physically small diode elements 210a and 210b, one can have the circuits switched to a different state. That is, when a high voltage, such as that from an AED appears, the diodes would forward bias thereby temporarily shorting out the diverter 112. Thereby the correspondingly high AED induced currents would be diverted away from the relatively sensitive (small) passive elements 116 and 114 in such a way that they not be harmed.

Figure 52:
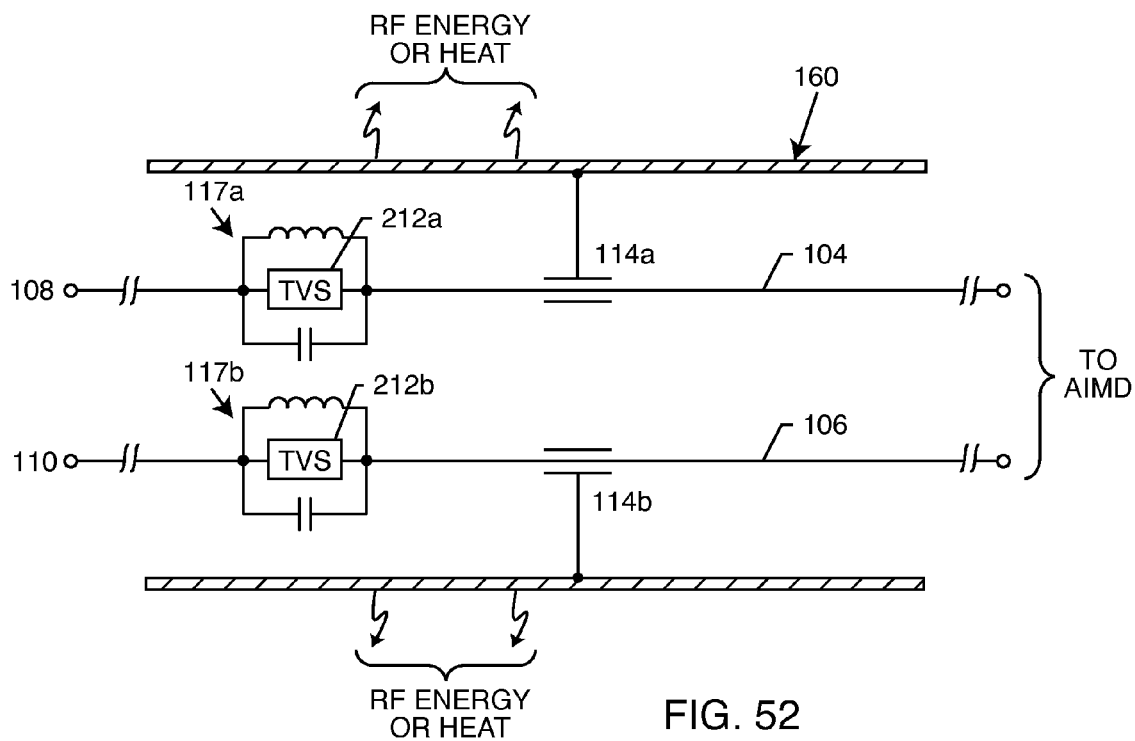
FIG. 52 is a schematic circuit diagram similar to FIG. 50, except that transient voltage suppressors are installed in parallel relation with each of the bandstop filter elements.

FIG. 52 is nearly identical to FIG. 50 except that transient voltage suppressors 212a and 212b have been added respectively in parallel with the bandstop filter elements 117a and 117b. Transient voltage suppressors 212a, 212b are nonlinear circuit elements which operate in much the same fashion as previously described for the back-to-back diodes 210a and 210b of FIG. 51. This family includes diodes, zener diodes, Transorbs™, Transguard®, metal oxide varistors, $Z_n0$ varistors, and other similar nonlinear circuit elements. The purpose of the transient voltage suppressors 212a and 212b in FIG. 52 is to bypass any high voltage induced currents such that these currents not flow through the relatively sensitive bandstop passive component inductor and capacitor elements.

Figure 53:
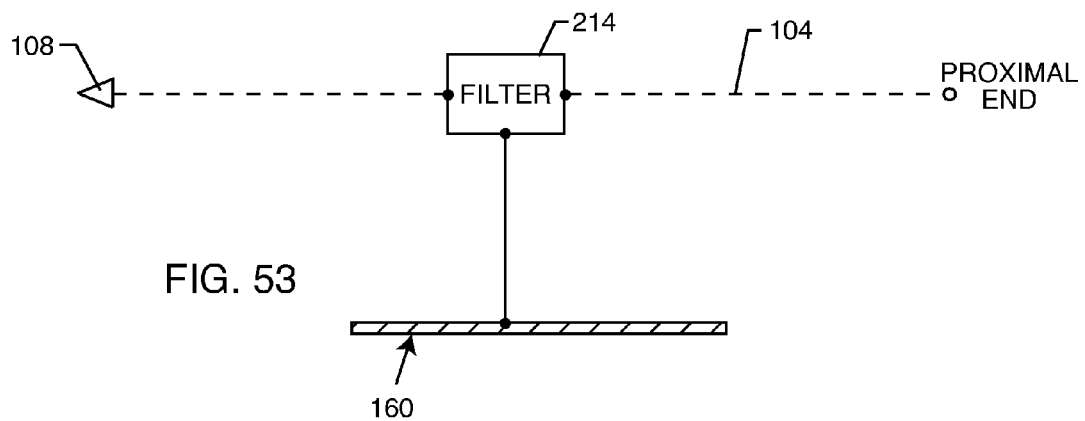
FIG. 53 is a schematic circuit diagram depicting a general filter element constructed in accordance with any one of the embodiments shown and described herein, wherein the filter element is coupled between the distal and proximal ends of a leadwire or the like, for dissipating RF energy or heat to an adjacent energy dissipating surface.

FIG. 53 illustrates a general filter element 214 which can be representative of any of the filters previously described. The filter element 214 of FIG. 53 is shown disposed between an electrical connection to an energy dissipating surface 160 as illustrated. The filter is shown connected to a proximal end of a leadwire 104 or the like with dashed lines, and connected to a distal end electrode 108 shown coupled to the leadwire 104 or the like with dashed lines. The reason for the dashed lines is an indication that the filter 214 can be placed anywhere between the distal end and the proximal end of the leadwire 104. The filter 214 and energy dissipating surface 160 could be located near the distal end, at the distal end, at a distal ring electrode 142 or near a distal ring electrode 142 such that it would float in the blood pool. The filter 214 can also be placed at or near the proximal end, or at any point between the distal and proximal ends.

In particular, the filter and associated energy dissipating surface 160 could be all the way at the proximal end of an abandoned lead. Leads are often abandoned in application for various reasons. Sometimes the lead becomes slightly dislodged, for example, from cardiac tissue such that the pacing threshold increases or is lost. Sometimes lead insulation becomes abraded and/or the leadwire itself is broken. Removing leads once they've been in the body for a long time can be very difficult as portions of the lead tend to become overgrown by body tissue. One is again referred to the article entitled, ICD EXTRACTION INFECTED/REDUNDANT LEADS EVERYDAY CLINICAL PRACTICE by Dr. Bruce Wilkoff. When one looks at the photographs of the extracted leads, one can see that they are very often substantially overgrown with tissue. Therefore, it is common practice to simply abandon leads.

In the prior art, the abandoned lead is simply capped such that body fluid will not enter it. This cap is nothing more than an insulative cap. However, it is also well known in the literature that abandoned leads can be quite dangerous in an MR scanning situation. High energy electromagnetic fields from the RF pulsed energy of a scanner intensifies at the ends of implanted leads. Because they are abandoned or capped at one end, this creates a reflection situation whereby all of the intense energy has no way to escape the lead except at the distal electrode end. This is the worst case situation because the distal electrode makes intimate contact with body tissue. For example, if the tissue was myocardial tissue, one runs a severe risk of creating burning or lesions in the heart. In the case of a deep brain stimulator, one runs the risk of causing deep lesions within the brain. In an abandoned lead, therefore, it is much more desirable that energy be dissipated at or near the proximal end as opposed to the distal end where there are sensitive body tissues involved. In general, active implantable medical devices are implanted in muscle or in fat tissues, for example, in the pectoral areas which are not so heat sensitive, but more importantly, are not implanted in an organ, whose function could be compromised. Accordingly, it is a feature of the present invention that any of the filter networks, as previously described herein, including those as shown in FIGS. 4 through 11, could be incorporated in a cap structure to be attached to the proximal end of the leadwire wherein such said cap structure includes an energy dissipating surface 160. For a further description of the problem and the need to provide a cap for abandoned leads, one is referred to U.S. Pat. No. 6,985,775.

Figure 54:
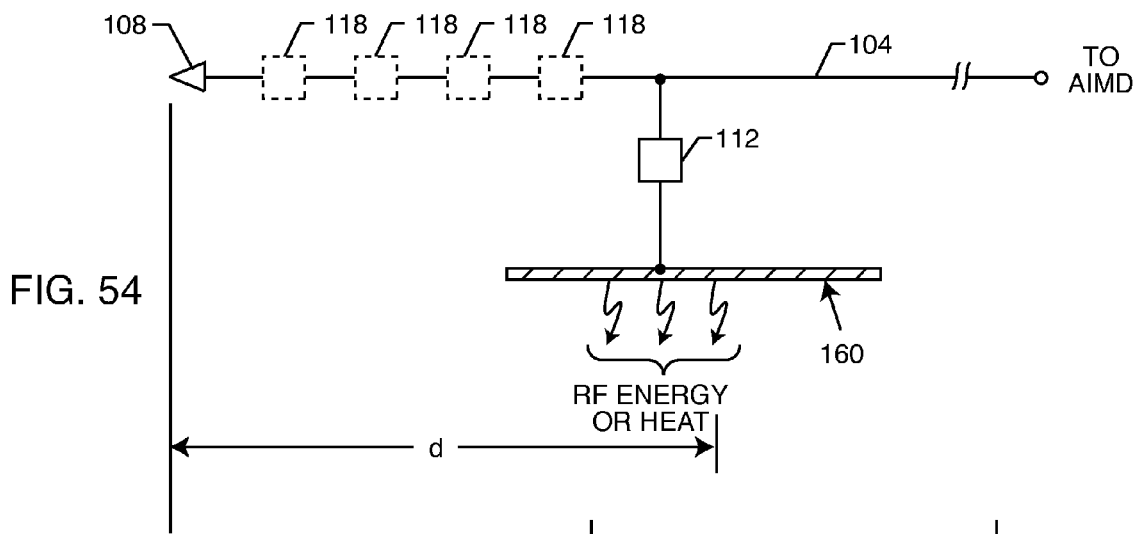
FIG. 54 is a schematic circuit diagram similar to FIG. 53, but showing alternative design considerations.

FIG. 54 shows an energy dissipating surface 160 in a relatively fixed location along the length of a leadwire 104. In accordance with the present invention, the energy dissipating surface 160 is placed a suitable distance d from a distal electrode 108 such that energy dissipation in the area of the surface 160 will not cause tissue overheating at or near the distal electrode 108. Also shown is a frequency impeding element 118 which can be moved to various locations along the length of the leadwire 104 as indicated by the multiple dashed-line boxes 118. For example, impeding element 118 could be placed near the energy dissipating surface 160, or it could be moved toward the distal electrode 108 at any one of several successive locations. The impeding element 118 such as a bandstop filter 117 or a series inductor will still work in conjunction with the diverting element 112 at any of these various locations. In fact, this can be an advantage in the present invention in order to make the distal tip electrode 108 and its associated leadwire 104 within the distance "d" smaller in diameter. In general, most leads for cardiovascular applications are restricted to the six French (0.079 inches in diameter) region. This can be problematic for a biventricular implant where the endocardial electrode must be threaded through the venous system and then into the coronary sinus and through the great cardiac vein to one of many branch vessels which are outside of the left ventricle. These branch vessels tend to be very small in diameter and very difficult to navigate, particularly for a large lead (size four French or smaller would be ideal). There is also a similar need for certain spinal cord and deep brain stimulators which must embody electrodes that are very small in diameter. Referring back to FIG. 54, one can see that by having a relatively large diverter element 112 associated with a energy dissipating surface 160 that is located at a distance d from the distal electrode, one can then downsize the diameter of the wiring along the length of distance d. By putting the frequency impeding element such as any one of the elements 118a, 118b and/or 118c, one can make this single component smaller than multiple components. Accordingly, frequency impeding elements do not have to be in direct physical proximity to diverting frequency selective elements 112. As taught in FIGS. 4, 5, 6, 37 and 38, the diverting element 112 can consist not only in a capacitor or an L-C resonant trap filter, but also could include a variety of low pass filters. Referring to FIG. 37, for example, one could see that an L section low pass filter is identical to the filter described in FIG. 54, wherein element 116 represents the inductor element and element 114 represents the capacitor element. Referring once again to FIG. 54, one can incorporate a T-type filter which embodies two inductor elements. In this embodiment, the left hand inductor element 118 would be to the left of the frequency diverting element 112 and a second inductor (not shown) would be located to the right of the diverter element 112 (see FIG. 37). This right hand inductor could be located in close physical proximity to the diverter element 112, or it could also be moved away as was described for the left hand inductor element at various locations as shown in FIG. 54.

Referring back to FIG. 54, it should be noted that the variable impedance element 112 can be monolithic ceramic (MLCC) capacitors, ceramic feedthrough capacitors, or other types of capacitive circuit components. In addition, the frequency selective element 112 can be a parasitic or distributive capacitor wherein the capacitance is formed through relatively high-dielectric materials between leadwires or electrodes in an energy dissipating surface.

Figure 55:
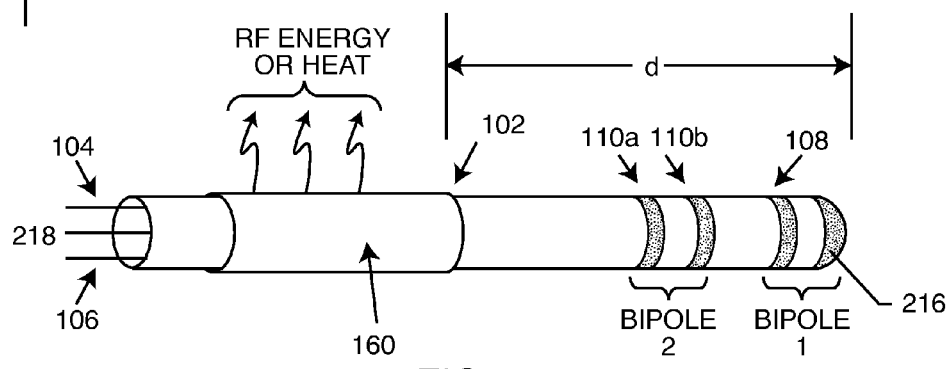
FIG. 55 depicts in somewhat schematic form a probe or catheter constructed in accordance with the present invention.

FIG. 55 illustrates a type of probe or catheter 102 which is typically used to both map and ablate the inside of cardiac chambers to eliminate or control certain types of arrhythmias. For example, in a patient with uncontrollable atrial fibrillation, this type of probe or catheter 102 would be inserted so that electrical mapping, between bipolar distal electrodes 108 and 216 or between electrodes 110a and 110b, could be performed to isolate and locate those areas from which the sporadic electrical activity is occurring. For example, this might be around a pulmonary vein. Reference is made to U.S. Pat. No. 7,155,271 for a more complete description of this type of need and procedure. After the areas that need to be ablated are located, the surgeon can apply RF ablation energy at a distal ablation electrode 216. This has the effect of burning the inside of cardiac tissue creating a scar which will isolate this area of erratic electrical activity. The goal here is to complete a scar structure such that the atrial fibrillation is terminated. Unfortunately, in the prior art, this procedure is done using real-time X-ray, fluoroscopy or other types of guidance, which does not adequately visualize soft tissue. Accordingly, the surgeon is working pretty much blind as the scars forming cannot be seen in real time. As explained in U.S. Pat. No. 7,155,271, it would be a great advantage if such procedures could be performed during real time MRI guidance. The problem is the MRI RF energy induced into the ablation catheter could cause overheating and sporadic formation of scar tissue at the wrong time and/or in the wrong location. In FIG. 55, one can see that there is a novel energy dissipating surface 160 of the present invention. This 160 surface is located at a distance "d" back from the distal tip such that the energy dissipating surface 160 will redirect energy away from both the electrical sensing electrodes 108, 110 and the RF ablation electrode 216 where they cannot overheat at inappropriate times. Frequency selective passive components (not shown), in accordance with the present invention, are connected in series with the leadwires, or from the inside of the energy dissipating surface 160 to the various leadwires 104, 106 and 218. These are the circuits that have generally been described in FIGS. 4 through 11 herein. For simplicity, they have not been shown in FIG. 54, but should be obvious to one skilled in the art from the previous drawings. In other words, the RF ablation electrode tip 216 will only overheat when the surgeon decides to activate the RF circuitry to deliberately form the scar tissue.

The energy dissipating surface 160 may include some materials or antenna structures that are readily visualized during active MRI guidance. This may be important so that a physician can ensure that if the probe or catheter is manipulated that the surface 160 not rest against the inside of, for example, the atrial septum. This is the area that is dissipating RF energy and heat during the active MRI. If the surface area of this surface 160 is sufficiently large so that very little temperature rise would occur, it would not matter if the surface 160 touched off against, for example, the inside wall of the cardiac septal wall. However, if the surface 160 was relatively small, then substantial temperature rise could occur if it was not kept within the freely flowing blood stream. In this case, it would be important that the physician be able to visualize the surface 160 and the MRI images so that it not be allowed to rest inappropriately against sensitive tissues on the inside of the atrium and cause inadvertent scar tissue or ablation to occur. Referring once again to FIG. 55, one can see that the ablation electrode 216 is connected to an RF ablation leadwire 218 which comes from RF ablation equipment (not shown) which is external to the patient. The sensing ring electrodes 108 and 110 are coupled to leadwires 104 and 106 which run through the center of the probe or catheter and also are connected to external equipment which is used to monitor electrical cardiac activity. These would typically be connected to an ECG or EKG recorder.

Figure 56:
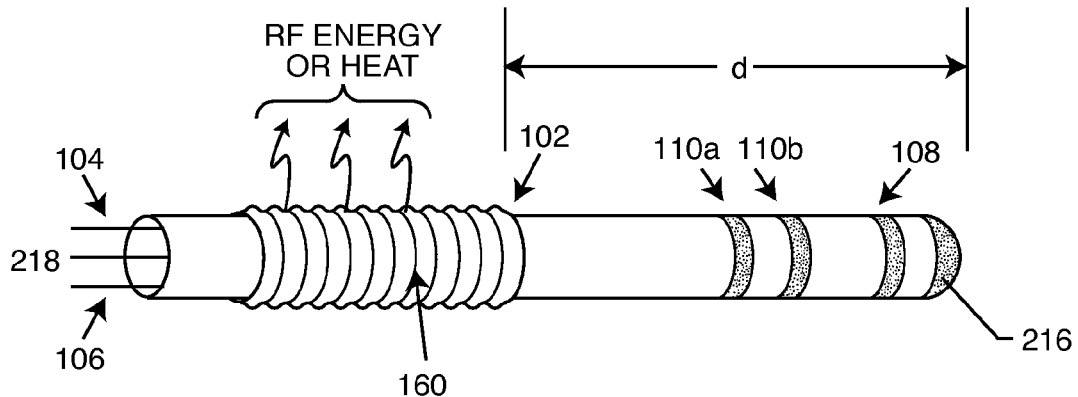
FIG. 56 is an illustration similar to FIG. 55, illustrating an alternative embodiment wherein the energy dissipating surface has been convoluted so that its surface area has been increased.

FIG. 56 shows a probe or catheter 102 similar to that illustrated in FIG. 55 except that the energy dissipating surface 160 has been convoluted so that its surface area has been increased. Such increasing of the surface 160 area, which is in contact with fluids, such as body fluids, will increase the amount of energy that is dissipated.

Figure 57:
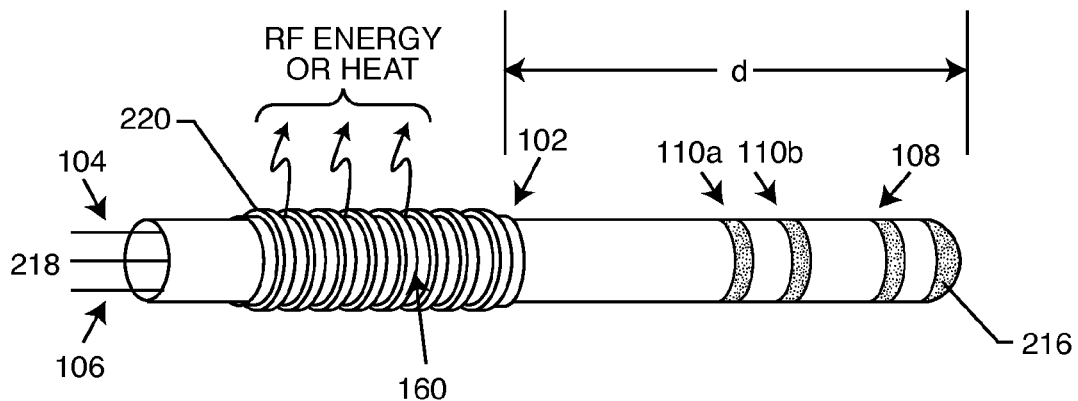
FIG. 57 is similar to FIG. 56, except that instead of convolutions, fins have been added to the energy dissipating surface.

FIG. 57 is very similar to FIG. 56 except that instead of convolutions, fins 220 have been added. These fins 220 also increase the surface area and increase the amount of energy or heat which is dissipated into surrounding fluids and tissues.

Figure 58:
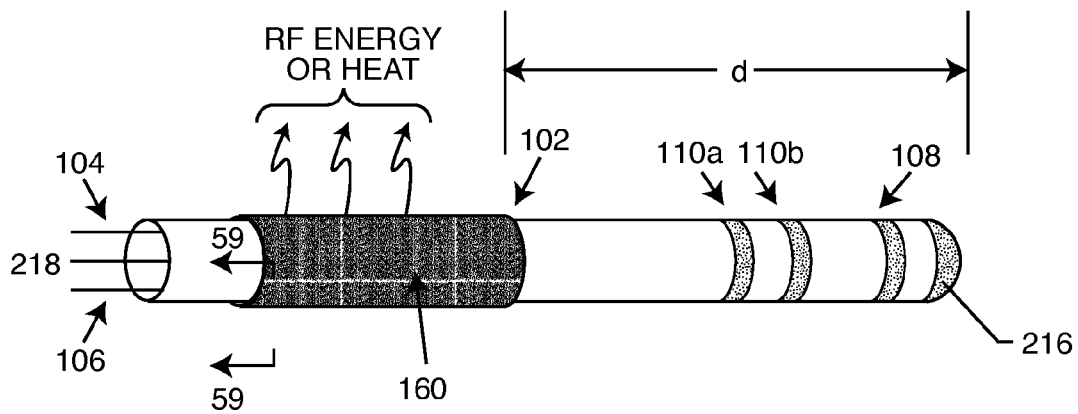
FIG. 58 is similar to FIGS. 56 and 57, except that the energy dissipating surface has its surface area increased through various surface roughening processes.

FIG. 58 is similar to FIGS. 56 and 57 except that the energy dissipating surface 160 has its surface area increased through various processes which are more thoroughly described in connection with FIGS. 59 and 60.

Figure 59:
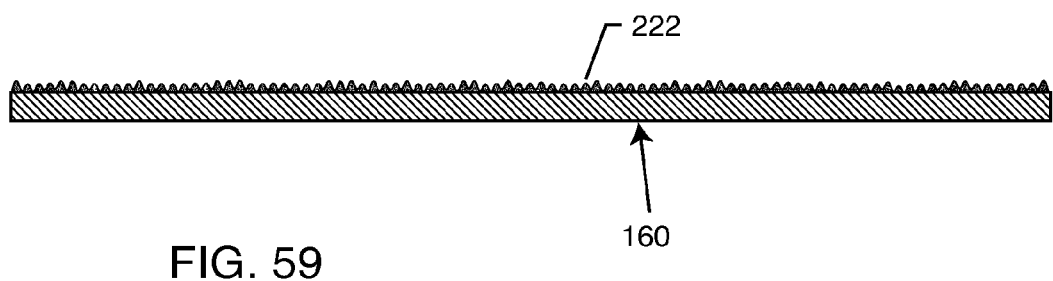

FIG. 59 is an enlarged, fragmented sectional view of the surface 160 taken from FIG. 58. The energy dissipating surface 160 area has been roughened to create a high surface area, through, for example, plasma etching, sputtering 222, chemical etching, or the like. A high surface area can also be accomplished by porous coating deposits utilizing physical vapor deposition, chemical vapor deposition or electron beam deposition processes. Such porous coating deposits can include fractal coatings, metal nitrides, titanium nitrides, metal oxides, metal carbides, or virtually anything that would provide a high surface or porous substrate. In addition, electrochemical deposition of porous coating, such as iridium-oxide, can also be utilized, as well as nucleate high surface area morphologically structured coatings, such as whiskers, sub-micron filaments, tubes, nanotubes, or other morphological structures such as columnar, titanium-nitride or iridium-oxide. Any of these types of surface conditionings can greatly increase the energy dissipating surface area.

Figure 60:
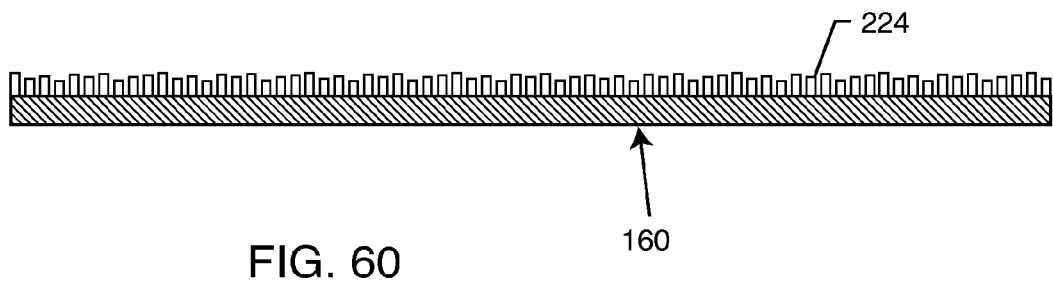
FIG. 60 is a view similar to FIG. 59, and illustrates the use of carbon nanotubes or fractal coatings to increase the surface area of the energy dissipating surface.

FIG. 60, which is similar to FIG. 59, illustrates the use of carbon nanotubes or fractal coatings 224 to increase the surface area and therefore the energy dissipation.

Figure 61:
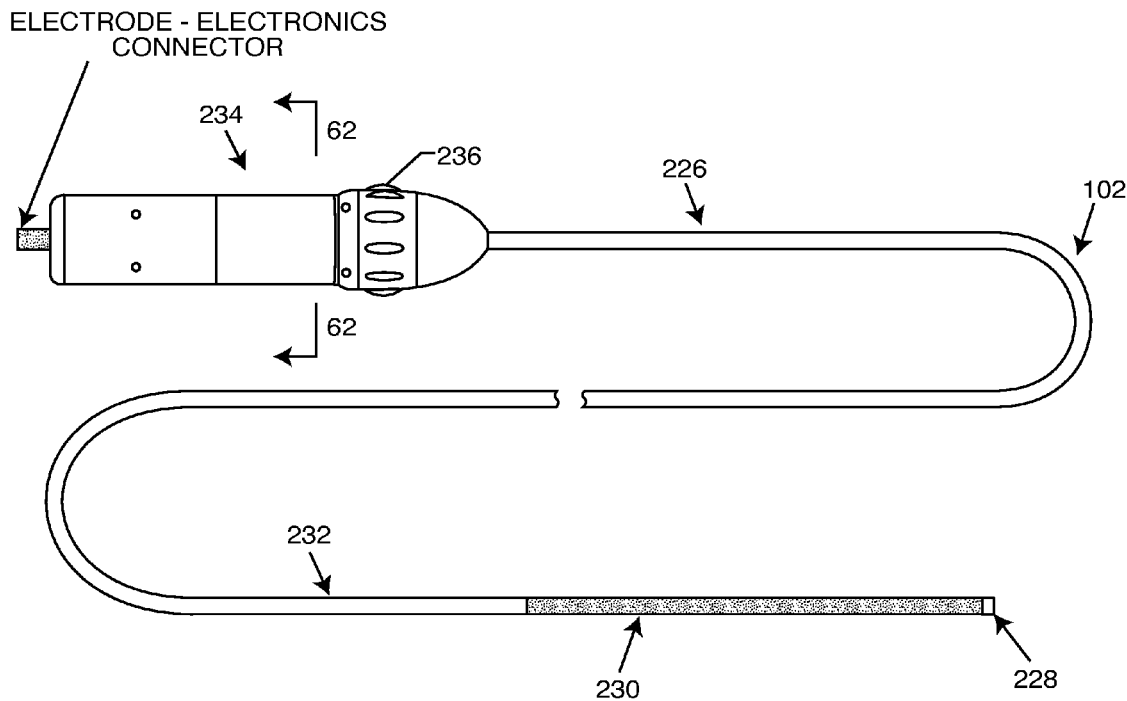
FIG. 61 is an illustration of a steerable catheter.

FIG. 61 shows a steerable catheter 226, which is typically used for a variety of applications including RF or cryo-ablation, cardiac mapping and many other purposes. Examples of RF ablation include treatment for nephrotic conditions, liver, brain, cancers and the like. For example, this would enable stereotactic ablation of certain lesions within the lung. An emerging field is the entire field of using ablation to treat various ventricular arrhythmias, including ventricular tachycardia. The illustrated catheter 226 in FIG. 61 is meant to be representative of all types of catheters or probes which can be inserted into the venous system or other areas of the human body. The catheter 226 has a tip 228 and an adjacent electrode surface 230, and a main catheter body 232, which can be steered around torturous paths. The steerable catheter 226 has a handle 234 which can have various shapes, sizes and configurations in the prior art. By twisting the illustrated cap 236 of the handle 234, one is able to steer the catheter 226 causing its tip 228 or other segments to bend as one guides it.

Figure 62:
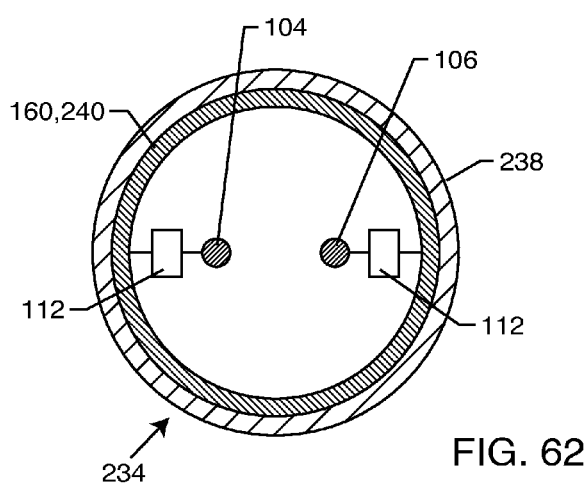
FIG. 62 is an enlarged section view taken generally along the line 62-62 from FIG. 61.

FIG. 62 is an enlarged section taken along line 62-62 in FIG. 61. FIG. 62 illustrates that the handle 234 includes an optional but preferred outer insulation sheath 238 which would typically be of plastic or similar material that would preferably not be highly thermally conductive. Inside of the handle 234 are shown in cross-section leadwires 104 and 106. The illustration of two leadwires is not meant to be limiting since any number of wires could be inside the handle 234 and catheter 232 to sense electrical activity or deliver ablation energy. In accordance with the present invention, there are frequency selective impedance elements 112 shown between the leadwires 104, 106 and an energy dissipating surface 160, such as a metallic sheath 240. The energy dissipating surface 160 does not necessarily have to be metallic, but it has to be capable of collecting RF energy and conducting thermal energy. This heat energy is therefore dissipated over the large surface area and thermal mass of the handle 234 itself. This results in very little temperature rise, but at the same time, accomplishes the goal of the present invention in redirecting RF energy out of the leadwires 104 and 106 that may be picked up by MRI RF pulsed fields and directing said energy into the relatively large surface area 240 inside the handle 234. Of course, one could eliminate the outer insulation sheath 238. However, in a preferred embodiment, the insulation sheath 238 would be relatively poor in thermal conductivity so that one did really not feel any temperature increase in his or her hand.

Figure 63:
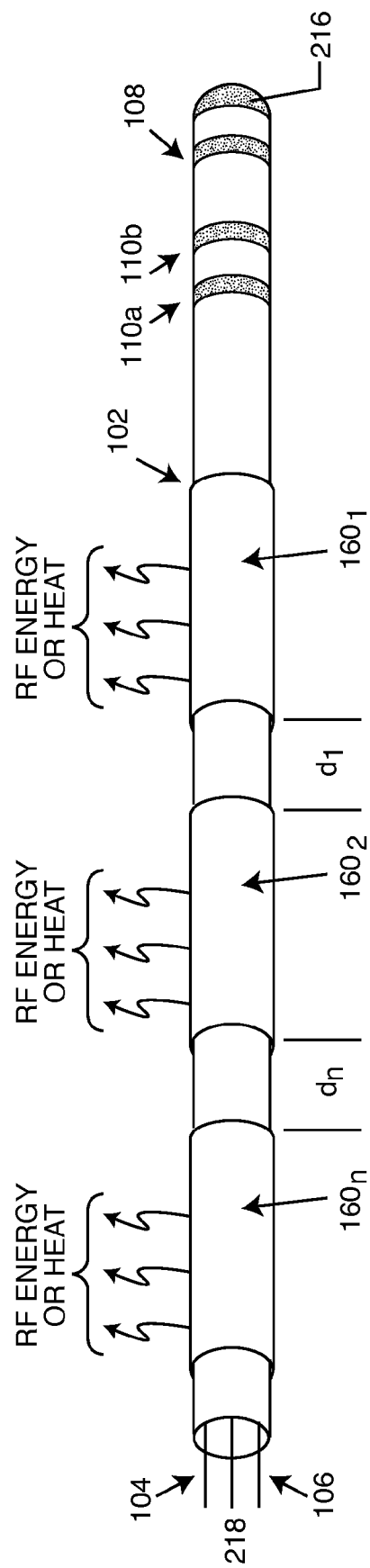
FIG. 63 is a schematic view of a probe or catheter similar to FIG. 55, except that the number of individual energy dissipating surfaces have been provided in distinct and spaced-apart segments.

FIG. 63 is very similar to FIG. 55 except that a number of individual RF energy or heat dissipating segments $160_1$, $160_2$ and $160_n$ are shown. These are shown spaced apart by separation gaps $d_1$ and $d_n$, which in reality can be quite small. The reason that these energy dissipating surfaces are segmented is so that they do not become physically and electrically long enough to become a significant fraction or multiple of a wavelength of the MRI pulsed frequency. Such short conductive sections do not pick up significant energy from MRI whereas elongated leadwires or conductors can, for example, resonate and pick up very significant amounts of MRI RF energy. It would be highly undesirable if the energy dissipating surfaces, as illustrated in FIG. 63, were formed to be continuous along the entire length of the catheter 102 as previously described in connection with FIG. 61. In this case, the energy dissipating surface would actually become an energy collecting surface because it would become a very effective antenna for the MRI pulsed RF signals. Accordingly, breaking this up into discrete segments prevents the surfaces 160 from actually becoming a receiver or antenna for the MRI induced energy.

FIG. 64 illustrates a paddle electrode 242 which could be used, for example, in spinal cord simulator applications. It has eight electrodes 244 housed in a biocompatible insulative and flexible body 246. Eight leadwires 248 are connected respectively to each of the eight electrodes 244. As previously discussed, the elongated leadwires 248 can pick up significant amounts of RF energy during MRI scanning. It is very important that the electrodes 244 do not overheat since they are in direct contact with the body, for example, with the spinal cord.

FIG. 65 illustrates the reverse side of the paddle electrode 242, where an energy dissipating surface 160 is located. As shown in FIG. 66, one can see that the electrodes 244 are conductive pads that contact the spinal nerve route or at least are closely associated with it. The leadwires 248 are each electrically connected to respective electrodes 244. There is a frequency variable impedance (or diverter) element 112 in accordance with the present invention shown between each electrode 244 and the energy dissipating surface 160. These can individual discreet capacitors or individual discreet L-C traps as shown in FIGS. 5 and 6. These can also be one continuous parasitic capacitance element that formed between the overlap of each of the electrodes and the area of the surface 160 itself. In this case, the insulative dielectric material 250 shown in FIG. 66 would be of relatively high dielectric constant. A high dielectric constant material is desirable so that the amount of parasitic capacitance would be relatively large. By using parasitic capacitance and appropriate dielectric materials, one eliminates the need to use individually installed passive circuit elements. Referring to FIGS. 64-66, one can see that the undesirable RF energy is dissipated on the opposite face of the paddle electrode 242 relative to the electrodes that are in contact with the spinal nerve route. In other words, the RF or thermal energy is dissipated over a relatively large surface area and is directed away from the sensitive juncture between the electrode body tissue contact area. This is important for two reasons, if the RF energy was allowed to concentrate on any one of the electrodes due to resonance phenomenon, then a very high temperature rise could occur which could cause thermal injury to the spinal nerve itself. By redirecting the energy in the opposite direction towards the muscle tissue and over a much larger surface area, much less temperature rise occurs, and even if it does, it is directed into less sensitive tissue.

Figure 67:
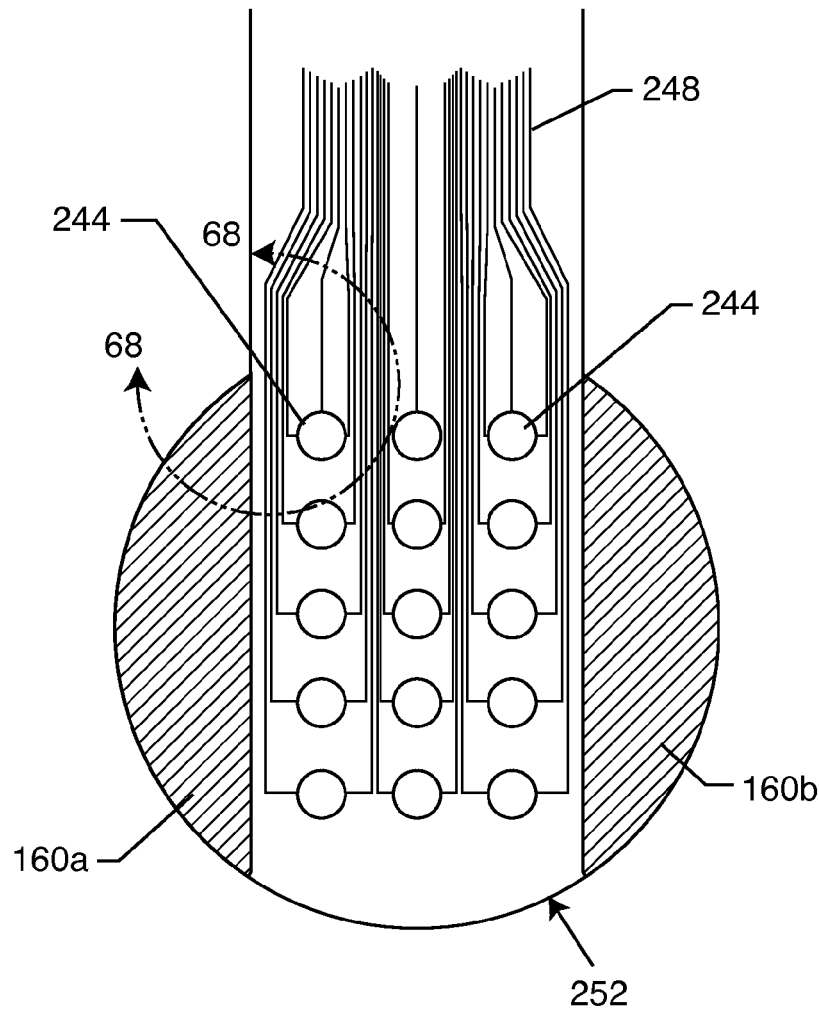
FIG. 67 is a top plan view of a different type of paddle lead structure in comparison with that shown in FIGS. 64-66.
Figure 68:
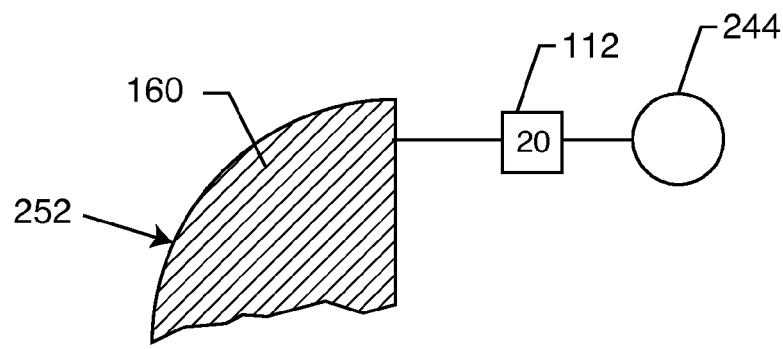
FIG. 68 is an enlarged electrical schematic view taken generally of the area indicated by the line 68-68 in FIG. 67.

FIG. 67 illustrates a different type of paddle lead structure 252 showing a total of fifteen electrodes 244. In this case there are two energy dissipating surfaces 160a and 160b. For maximum surface area, the energy dissipating surfaces could be on the top surface of the paddle lead structure 252, as well as on the backside or back surface (not shown). In accordance with the present invention, FIG. 68 illustrates a frequency selective variable impedance element 112 which is used to divert RF energy from the electrodes 244 to the surfaces 160.

Figure 69:
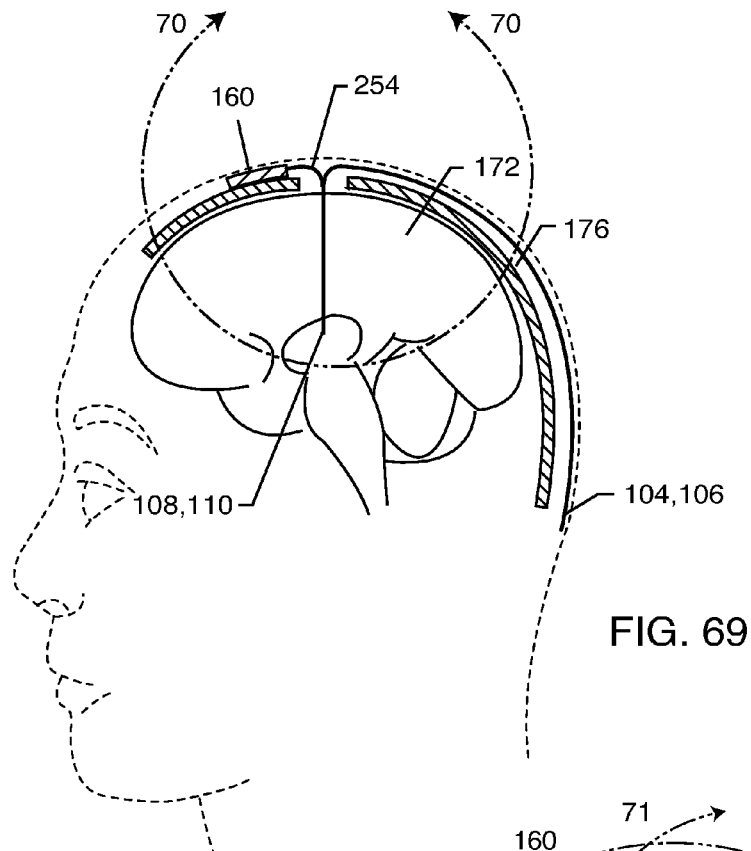
FIG. 69 is a schematic illustration similar to FIG. 120, showing use of a tethered energy dissipating surface in accordance with the present invention.
Figure 70:
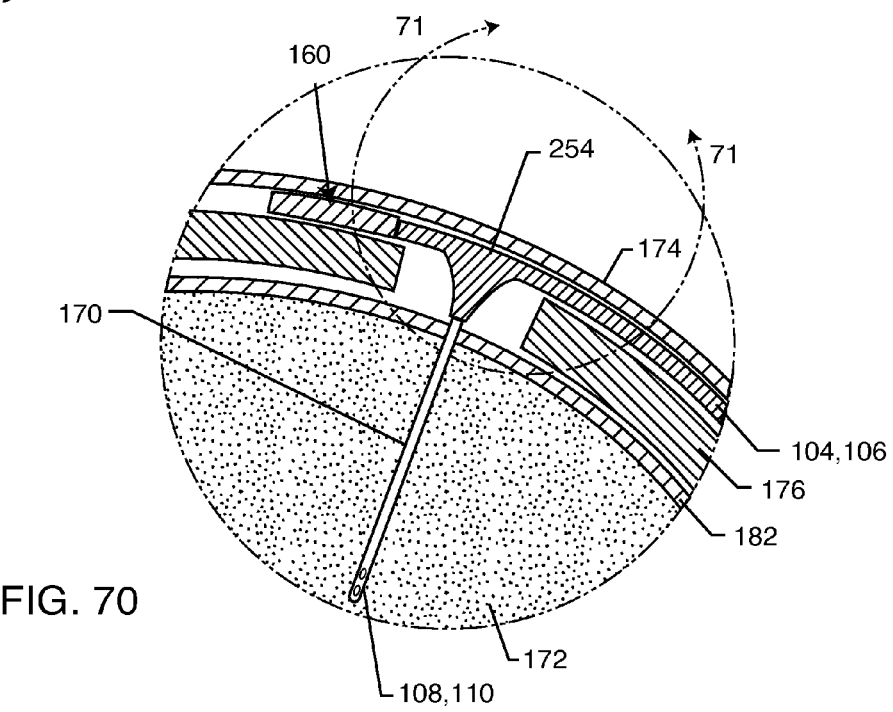
FIG. 70 is an enlarged sectional view of the area indicated by the line 70-70 in FIG. 69.
Figure 71:
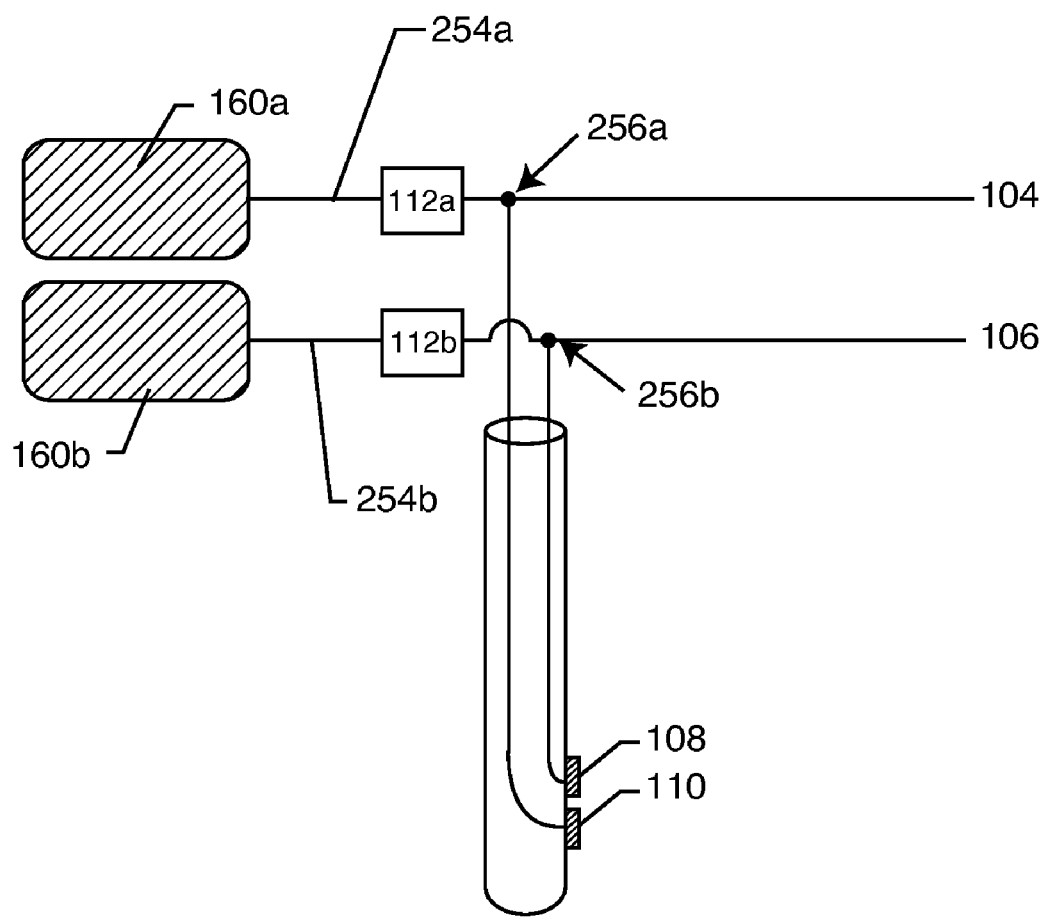
FIG. 71 is an enlarged, somewhat schematic illustration of the components found within the area designated by the line 71-71 in FIG. 70.

FIG. 69 is very similar to FIG. 28 in that it shows a section of human head with a deep brain stimulator disposed therein. There is a plurality of leadwires 104 and 106 which are connected to an AIMD or pulse generator (not shown). The pulse generator would typically be placed in the pectoral region and leadwires 104 and 106 would be routed up along the patient's neck to the deep brain electrodes 108 and 110. Referring to FIGS. 69-71, one can see that there is a novel tether 254 or wire arrangement where the leadwires 104, 106 are not only connected to the distal electrodes 108, 110, but they are also connected to a pair of energy dissipating surfaces of 160a and 160b. In FIG. 70, one can see the tether area 254 wherein the leadwires 104, 106 connect individually to the electrodes. As shown in FIG. 71, the leadwires 104, 106 have a connection inside the tether area 254 such that the wires are routed both to the distal electrodes 108 and 110 and also through respective junctions 256a and 256b to two individual energy dissipating surfaces (160a and 160b). The leadwire 104 has a direct electrical connection at junction 256a to distal electrode 110. In turn, leadwire 106 has a direct connection at junction 256b to distal electrode 108. However, at the junctions 256a and 256b, also connected are frequency selective elements 112 which in turn are connected respective energy dissipating pad or surfaces 160a and 160b. Of course the separate energy dissipating pads could be one large energy dissipating pad. However, in order to maximize surface area and facilitate surgical implantation, two pads are shown. These are originally implanted by the physician underneath a skin flap which is then sewn back down in place. In this way, any heat that is generated during MRI procedures is generated on the top side of the skull well away from any brain matter.

Figure 72:
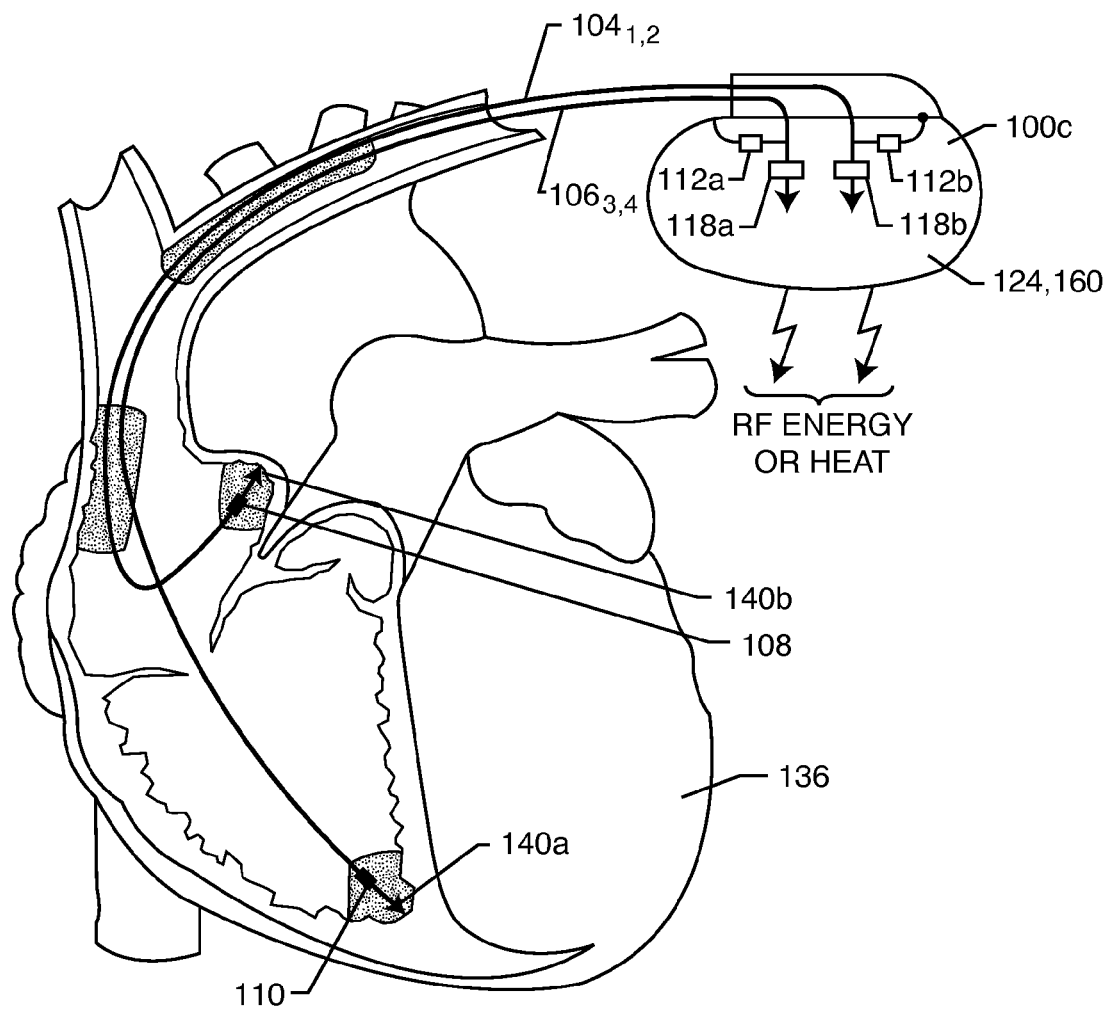
FIG. 72 is a schematic illustration of a human heart and an associated cardiac pacemaker embodying the present invention.

FIG. 72 shows a cross-sectional view of a human heart 136. Shown is a active implantable medical device such as a cardiac pacemaker 100C with leads 104 and 106 implanted into chambers of the human heart. Bipolar lead 104 is implanted into the right atrium terminating in a distal TIP electrode 140b and a distal RING electrode 108. Bipolar lead 106 is also implanted transvenously into the right ventricle terminating in a distal TIP electrode 140a and distal RING electrode 110.

The shaded areas show areas where the leads tend to be entrapped by tissue encapsulation over time. The cardiac pacemaker 100C is contained within a conductive housing 124. The conductive housing in the prior art is typically of titanium, stainless steel or the like. In the present application, the conductive housing also acts as an energy dissipating surface 160. Shown disposed inside of the conductive housing 124 of the AIMD 100C are frequency selective diverter elements 112 and impeder elements 118 of the present invention. In this case, there would be a total of four impeders and four diverters as one is generally required in each leadwire of the implanted leads. Each bipolar lead has two leadwires associated with it for the TIP and RING circuits.

Figure 73:
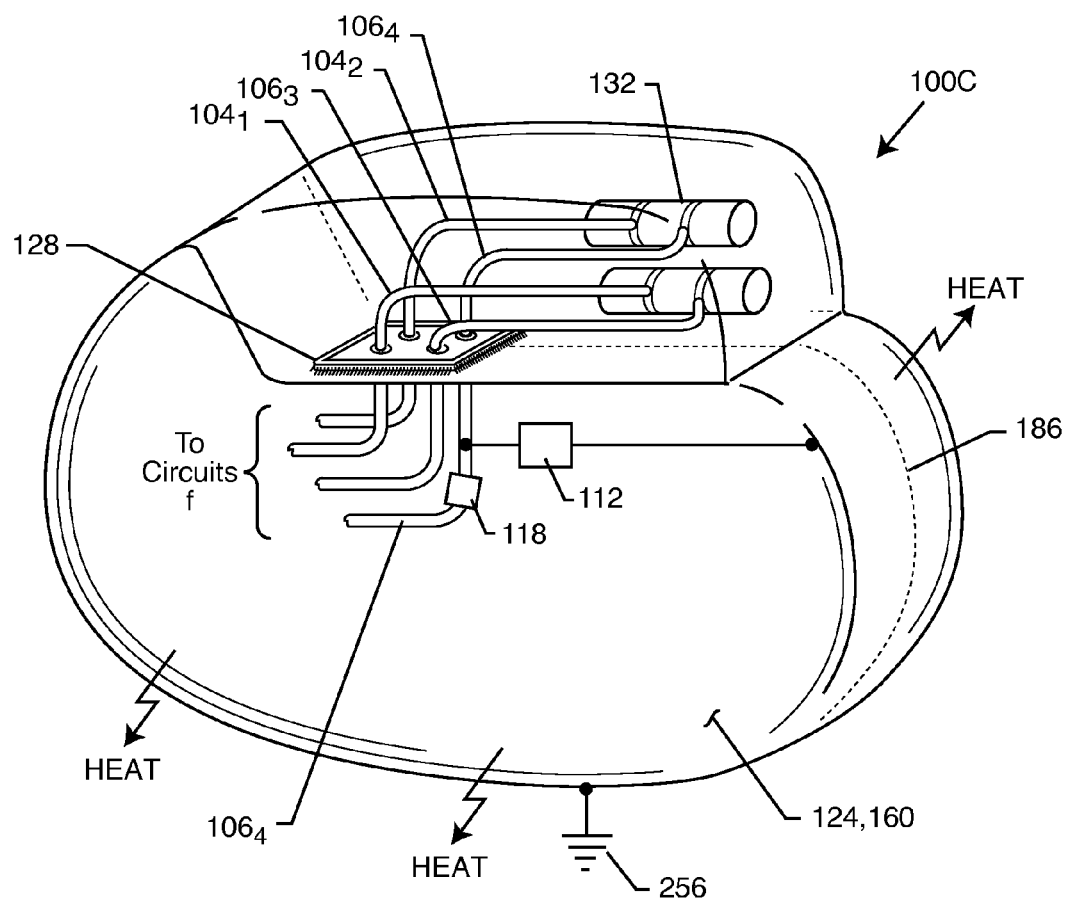
FIG. 73 is an enlarged perspective view of a cardiac pacemaker such as that shown in FIG. 72 illustrating use of the AIMD housing as an energy dissipating surface in accordance with the present invention.

FIG. 73 is another view of an AIMD such as a cardiac pacemaker 100C as shown and described in connection with FIG. 72. A conductive housing 124 in this case is of titanium which has been laser welded 186 to form a hermetically enclosed structure which is also an electromagnetic shield. Accordingly, the electronic circuits that are disposed inside of the AIMD housing are protected both from body fluid and from electromagnetic interference. A frequency selective diverter element 112, in accordance with the present invention, is shown disposed between leadwire $106_4$ and the conductive housing 124 of the AIMD 100C. Also shown is an optional frequency selective impeder 118 in accordance with the present invention. The AIMD housing 124 acts as a high surface-area energy dissipating surface 160. Impeder elements 118 and 112 would generally be disposed on each of the leadwires $104_1$, $104_2$, $106_3$ and $106_4$. They are only shown on one of the circuits for simplicity.

Figure 74:
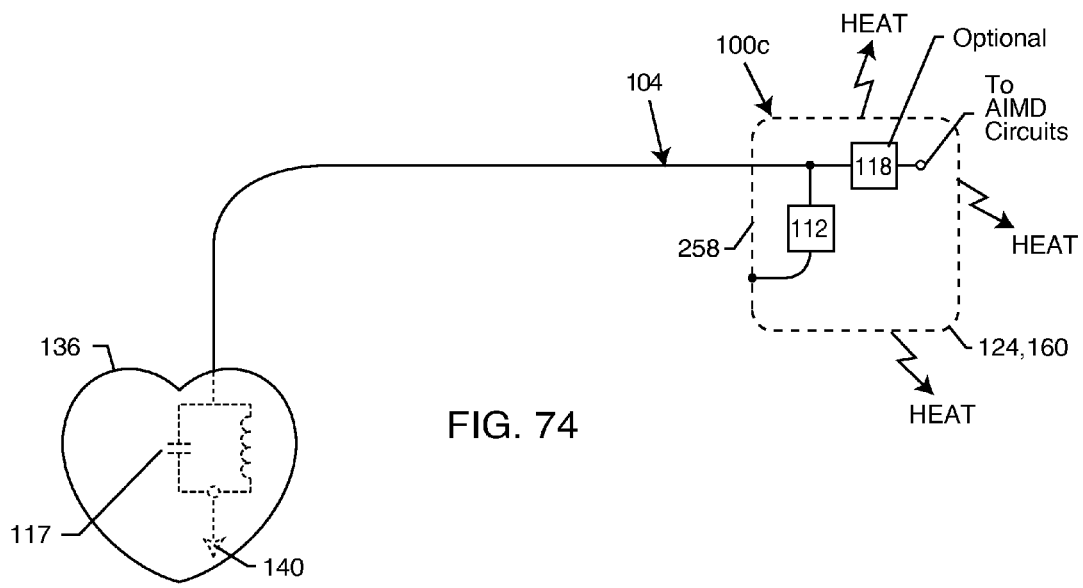
FIG. 74 is an electrical schematic illustration illustrating a diverter element disposed between the AIMD circuitry and the AIMD housing, and provision of an optional impeder element.

FIG. 74 is a schematic diagram taken generally from FIGS. 72 and 73 showing the general AIMD 100C with its conductive housing 124. In accordance with the present invention, the conductive housing 124 acts as an energy dissipating surface 160. Using the AIMD housing 124 itself as an energy dissipating surface is particularly effective. The first reason is that the AIMD housing tends to be relatively very large in surface area. Therefore it can distribute RF induced energy over this relatively large surface area resulting in very little temperature rise. The other reason using the AIMD housing 124 as an EDS surface 160 is important is that it is generally located far from sensitive body tissues. For example, in the case of cardiac pacemakers, the AIMD 100C would typically be located in a pectoral muscle pocket or in fatty tissue just below the skin's surface. This is far removed from the relatively more sensitive cardiac tissues. The same is particularly true of a spinal cord stimulator or a deep brain stimulator. The AIMD housing or pulse generator housing itself is located far from the spinal cord nerve root tissues or from deep brain tissues. Having a few degrees temperature rise in a muscle is far preferable to having a temperature rise inside the brain tissue. Referring once again to FIG. 74, the dashed line 258 represents the AIMD hermetically sealed housing. Located within it is the novel diverter circuit 112 and an optional impeder circuit 118 of the present invention. Lead 104 is directed from the AIMD into body tissues. In this case, it is directed to cardiac tissues. Shown is an optional bandstop filter 117 which in a particularly preferred embodiment works ideally with the present invention. The operation of the bandstop filter is more thoroughly described in U.S. Pat. No. 7,363,090, the contents of which are incorporated herein. The bandstop filter presents a high impedance between the implanted lead and body tissue. Accordingly, RF energy that may be induced on the implanted leads from MRI imaging procedures are impeded from flowing into the cardiac tissue. The energy dissipating surface 160 of the present invention works in concert with this. RF energy is still present in the lead, but because of the bandstop filter 117, it is impeded from flowing into myocardial tissue. Therefore, it is redirected to the energy dissipating surface 160 of the AIMD housing 124 by means of a diverter 112. The operation of the diverter 112 is made more effective when used in combination with an optional impeder 118. As will be seen, any number of impeders can be used in combination with diverters to form multi-element filters. These can be multi-element low pass filters as previously described in FIG. 37, or they can be combinations of impeders and diverters as previously described in FIGS. 4-11.

Figure 75:
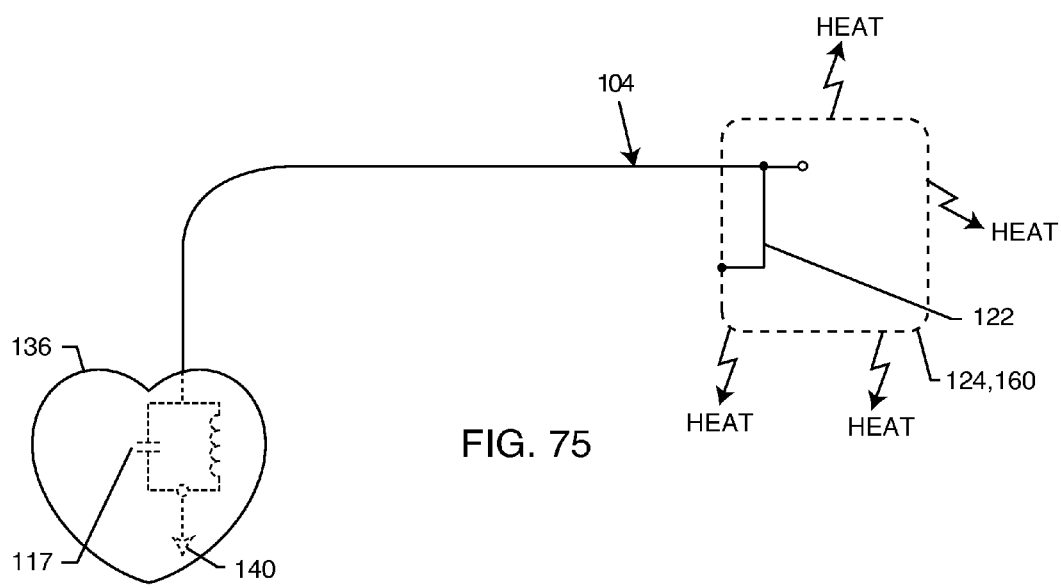
FIG. 75 is an electrical schematic illustration similar to FIG. 74, except that the optional impeder element is not shown and the diverter element is shown as a short circuit.

FIG. 75 is very similar to FIG. 74 except that the optional impeder circuit is not shown for clarity. In this case, the diverter 112 is a short circuit 122 as previously described in FIG. 9. In general, this is not a preferred embodiment since a short circuit would also tend to short out a proper operation of the AIMD itself.

Figure 76:
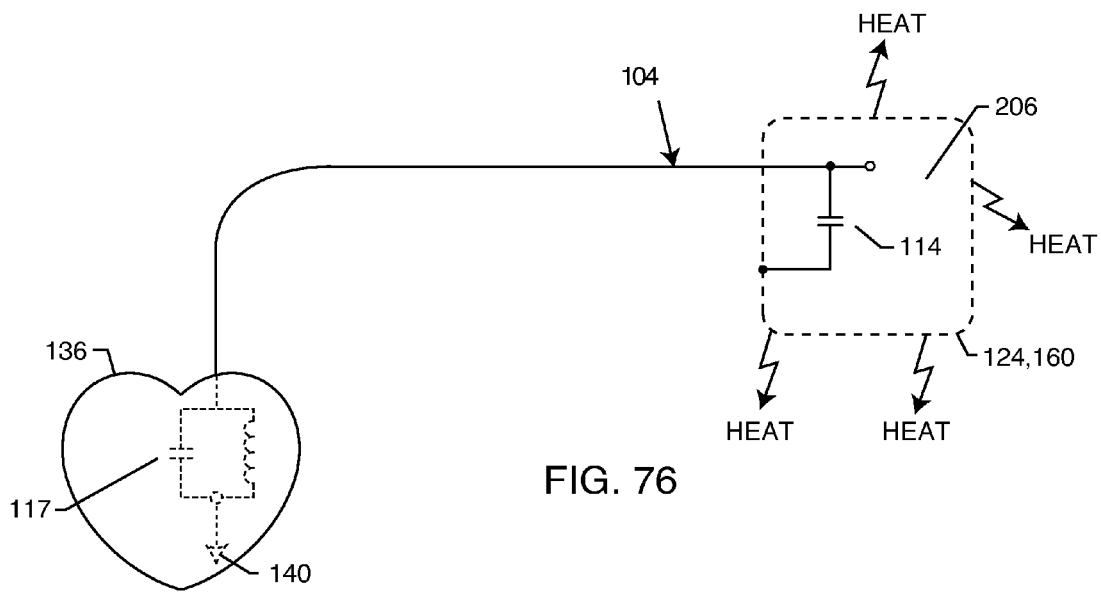
FIG. 76 is an electrical schematic illustration similar to FIG. 75 except in this case the diverter element is shown as a capacitor.

FIG. 76 is again very similar to FIG. 74 except in this case the diverter is a capacitor 114. In a preferred embodiment, capacitor 114 would be a feedthrough capacitor. The operation of capacitors, impeders and diverters was also described in FIGS. 21-50 herein. The impeder capacitor element illustrated in FIG. 76 acts as a variable frequency reactance. It tends to look like an open circuit at low frequencies, but tends to look like a short circuit at very high frequencies such as the RF pulse frequency of modern MRI systems.

Figure 77:
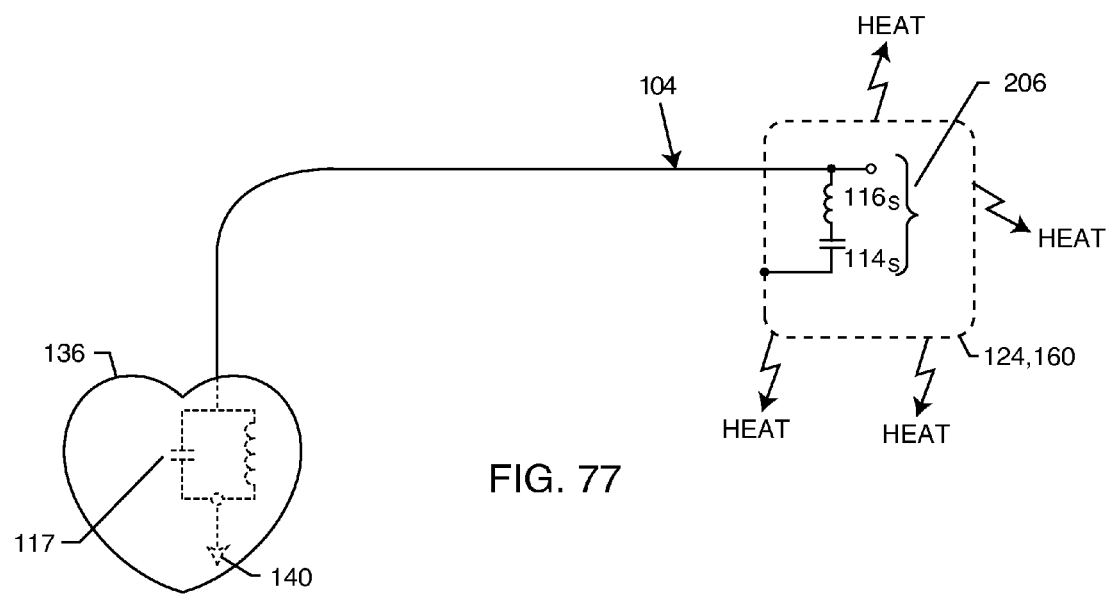
FIG. 77 is an electrical schematic illustration similar to FIGS. 75 and 76, except the diverter element in this case is an L-C trap filter.

FIG. 77 is very similar to FIG. 74 except that the diverter element 112 in this case is an L-C trap filter. It may also have a series resistance to control its Q and resonant bandwidth. In this case, the trap filter was previously described in FIG. 39, 39a and FIG. 40 herein. A trap filter is very effective in looking like a very low impedance (short circuit) at one selected frequency. In a preferred embodiment, the L-C trap filter of FIG. 77 would be designed to be resonant at a selected MRI RF pulse frequency. Multiple L-C trap filters may be used to divert multiple MRI frequencies.

Figure 78:
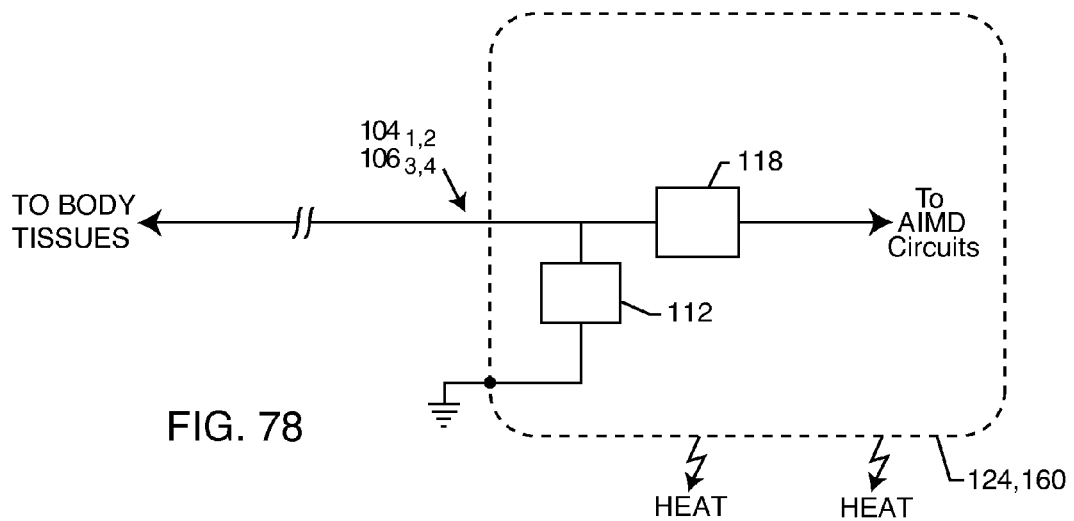
FIG. 78 is an electrical schematic illustration similar to FIG. 74, except that it is representative of any type of AIMD.
Figure 79:
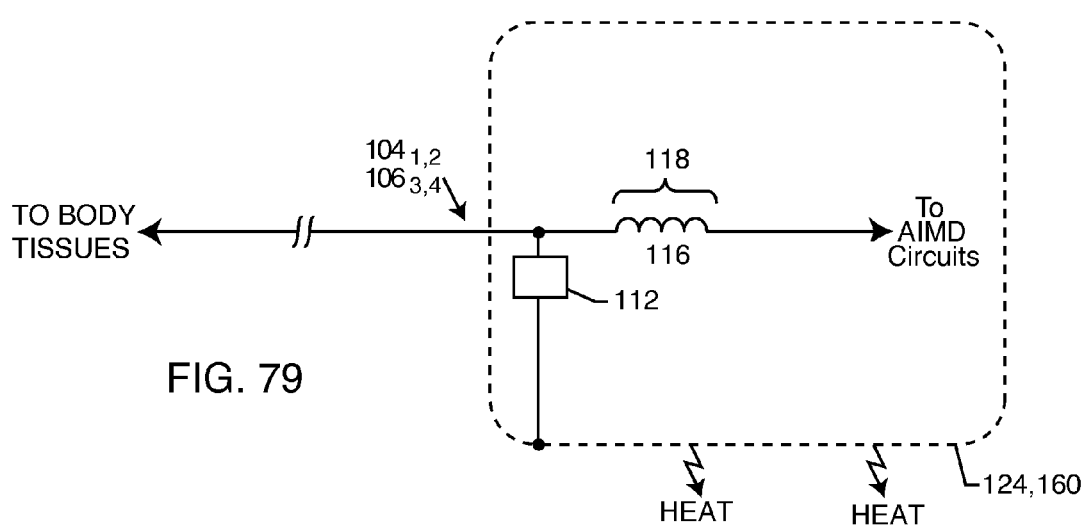
FIG. 79 is an electrical schematic illustration similar to FIG. 78, wherein the impeder element is an inductor.
Figure 80:
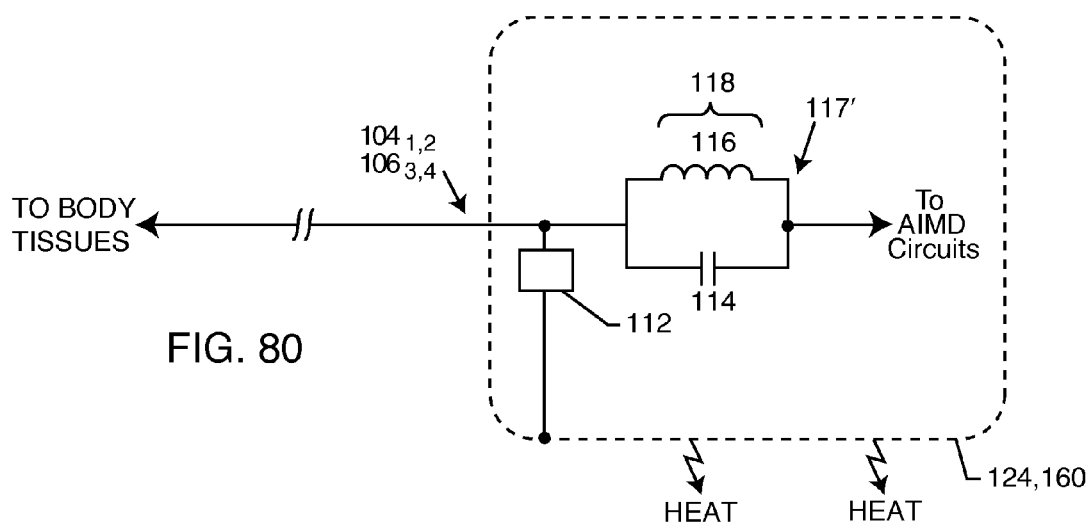
FIG. 80 is an electrical schematic illustration similar to FIGS. 78 and 79, wherein the impeder element comprises an L-C bandstop filter.

FIG. 78 is very similar to FIG. 74 and is representative of any type of AIMD. Shown is AIMD housing 124 which acts as an EDS surface 160. FIGS. 78, 79 and 80 will be used to describe impeder circuits 118 that can be used in combination with any of the previously described diverter circuits 112. It will be also shown that any number of impeders and diverters can be used in any combination.

FIG. 79 is taken from FIG. 78 wherein the impeder circuit 118 is an inductor 116. The inductor acts as a variable frequency reactance element. At low frequency, the inductor tends to look like a short circuit, and at high frequency, the inductor tends to look like a very high impedance. For example, at MRI RF pulse frequencies, the inductor element 116 would look like a high impedance therefore impeding the flow of RF current to AIMD circuitry. By acting as a high impedance it also aids in redirecting said RF pulsed energy through diverter 112 to the energy dissipating surface 160.

FIG. 80 is also taken from FIG. 78. In this case, impeder circuit 118 consists of an L-C bandstop filter consisting of inductor 116 in parallel with capacitor 114. The bandstop filter would be designed to be resonant at a selected MRI RF pulsed frequency. Bandstop filters tend to look like a very high impedance at resonance, thereby impeding the flow of RF energy. Again, the bandstop filter is designed to work in conjunction with one or more of the previously described impeders 112.

Figure 81:
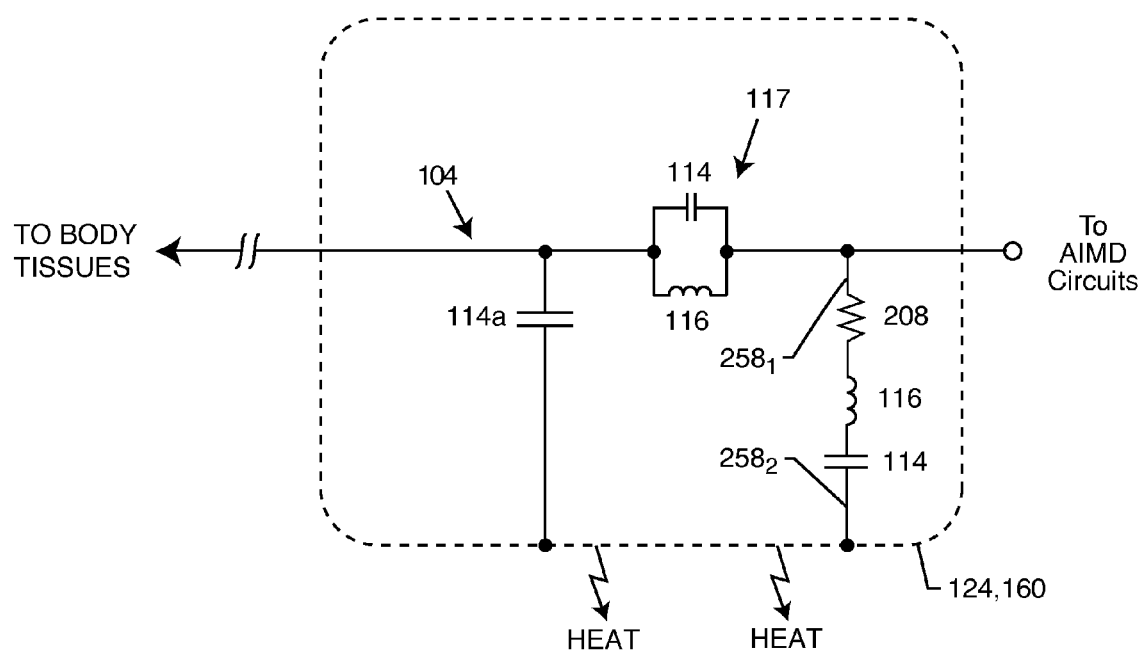
FIG. 81 is an electrical schematic illustration similar to FIGS. 78-80, illustrating how diverters and impeders can be used in combination with each other.

FIG. 81 is an example of how diverters and impeders can be used in combination with each other. The AIMD housing 124 is shown as an energy dissipating surface 160. An implanted lead 104 is directed outside of the AIMD housing into distal electrodes adjacent human tissues. Starting from the left side of FIG. 81, as one enters the AIMD housing, one first encounters diverter capacitor $114_a$. When moving further to the right, one encounters impeder bandstop filter 117 which consists of inductor 116 in parallel with capacitor 114. This would be designed to be resonant, for example, at 64 MHz, which is the RF pulsed frequency of a 1.5 Tesla MRI scanner. When moving further to the right, one encounters the L-C trap filter consisting of resistor 208, inductor 116, and capacitor 114. This is also designed to be resonant at a selected MRI RF pulse frequency.

Figure 82:
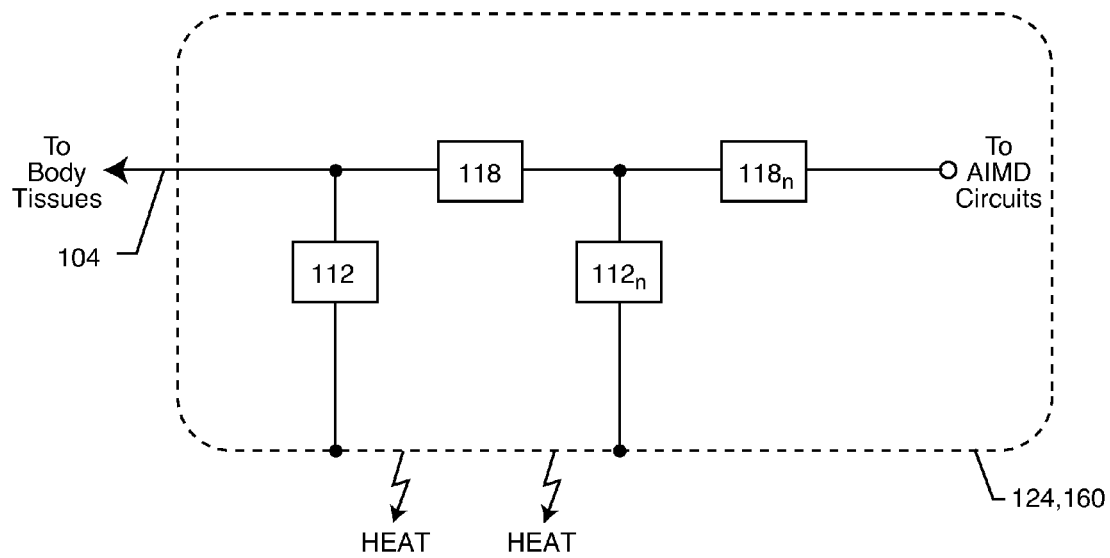
FIG. 82 is an electrical schematic illustration similar to FIGS. 74 and 78, illustrating an implanted lead which is directed to stimulate body tissues.

FIG. 82 is a schematic diagram taken generally from FIGS. 74 and 78. Shown is an implanted lead 104 which is directed to stimulate body tissues. It enters the AIMD hermetic housing through a hermetic terminal (not shown). The hermetic housing 124 of the AIMD also acts as an energy dissipating surface 160 in accordance with the present invention. As the lead enters the housing of the AIMD, it first encounters a diverter element 112 working in combination with an impeder element 118. Then there is a second diverter element $112_n$ working in combination with an optional second impeder element $118_n$. Subscript n denotes that this combination can be repeated as many times as desired. In accordance with the present invention, the diverter element can be a capacitor or an L-C trap filter. The impeder elements can be inductors or bandstop filters. Using any combination of the diverters and impeders, one can build the circuit previously described in FIG. 81 or any of the low pass filters as previously described in FIG. 37. It will be obvious to those skilled in the art that the order of the impeder and diverter elements could also be reversed.

Figure 83:
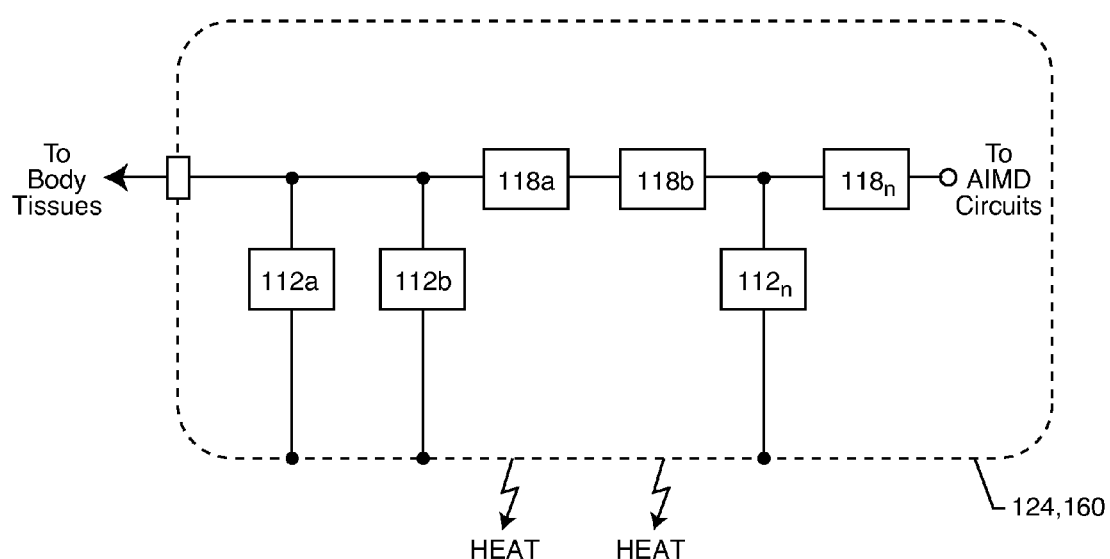
FIG. 83 is an electrical schematic illustration similar to FIG. 82, except that it illustrates that the diverter elements can be placed in parallel with one another and that the impeder elements can be placed in series with one another.

FIG. 83 is very similar to FIG. 82 except that it illustrates that the diverter elements 112 can be placed in parallel with one another and impeder elements 118 can be placed in series with one another. Again, this can be used to form any combination to optimize energy dissipation 160 from the AIMD housing 124. For example, diverter element 112 could be a capacitor which is placed directly in parallel with a second diverter element which is an L-C trap filter 112b. These could work in combination with optional impeder elements 118a and 118b. As illustrated, impeder element 118a could be a simple inductor, whereas impeder element 118b could be one or more L-C parallel bandstop filters. As shown, these can be combined as many times as possible illustrated by $112_n$ and $118_n$.

Those skilled in the art will appreciate that the present invention can be extended to a number of other types of implantable medical devices, including deep brain stimulators, spinal cord stimulators, urinary incontinence stimulators and many other types of devices.

Although several embodiments of the invention have been described in detail, for purposes of illustration, various modifications of each may be made without departing from the spirit and scope of the invention. Accordingly, the invention is not to be limited, except as by the appended claims.

What is claimed is:

1. A passive component network for an active implantable medical device, comprising:
   a) an active implantable medical device (AIMD) comprising an electrically or thermally conductive housing, wherein the AIMD is configured to be connectable to a lead, the connectable lead comprising a length extending between and to a proximal end adjacent to the AIMD housing and a tissue-stimulating or biological-sensing electrode at a distal tip end; and
   b) a frequency selective energy diversion circuit housed inside the AIMD housing for diverting high-frequency energy away from the lead connectable to the AIMD housing for dissipation of the high-frequency energy;

c) wherein the high frequency energy comprises an MRI frequency.

2. The passive component network of claim 1, wherein the MRI frequency comprises a range of MRI frequencies.

3. The passive component network of claim 1, wherein the MRI frequency in megahertz is selected from the group of frequencies comprising 42.56 times the static magnetic field strength in Teslas of an MRI scanner.

4. The passive component network of claim 1, wherein the frequency selective energy diversion circuit comprises a low pass filter.

5. The passive component network of claim 4, wherein the low pass filter is selected from the group consisting of a capacitor, an inductor, a Pi filter, a T filter, an LL filter, and an "n" element filter.

6. The passive component network of claim 5, wherein the capacitor comprises parasitic capacitance.

7. The passive component network of claim 1, wherein the frequency selective energy diversion circuit comprises at least one series resonant LC trap filter.

8. The passive component network of claim 7, wherein the frequency selective energy diversion circuit comprises a plurality of LC trap filters resonant, respectively, at different MRI frequencies.

9. The passive component network of claim 1, including an impeding circuit associated with the diversion circuit, the impeding circuit providing for raising the high-frequency impedance of a lead or a leadwire, the impeding circuit being disposed between said diversion circuit and AIMD electronic circuits.

10. The passive component network of claim 9 wherein the impeding circuit comprises at least one inductor.

11. The passive component network of claim 10 wherein the at least one inductor comprises an inductor chip.

12. The passive component network of claim 10 wherein the at least one inductor comprises an inductor wire wound onto a ferromagnetic or non-ferromagnetic mandrel.

13. The passive component network of claim 10, wherein the at least one inductor comprises a pair of inductor elements, the diversion circuit being coupled between the pair of inductor elements and the AIMD housing.

14. The passive component network of claim 13 wherein the diversion circuit comprises at least one capacitor.

15. The passive component network of claim 9, wherein the impeding circuit comprises a bandstop filter.

16. The passive component network of claim 9, wherein the conductive housing protects the diversion and impeding circuits from direct contact with patient body fluids.

17. The passive component network of claim 16, wherein the active implantable medical device (AIMD) comprises a deep brain stimulator.

18. The passive component network of claim 1, wherein the AIMD is configured to be connectable to at least a pair of leads, each lead having a length extending between and to a proximal end that is electrically connectable to the AIMD housing and a tissue-stimulating or biological-sensing electrode at a distal tip end.

19. The passive component network of claim 18, wherein the electrode comprises an ablation tip electrode.

20. The passive component network of claim 1, wherein the active implantable medical device (AIMD) comprises a probe or a catheter.

21. The passive component network of claim 20, wherein the AIMD housing comprises at least a portion of a handle for the probe or the catheter.

22. A passive component network for an active implantable medical device, comprising:

a) an active implantable medical device (AIMD) comprising an electrically or thermally conductive housing, wherein the AIMD is configured to be connectable to a lead, the connectable lead comprising a length extending between and to a proximal end adjacent to the AIMD housing and a tissue-stimulating or biological-sensing electrode at a distal tip end;

b) a frequency selective energy diversion circuit housed inside the AIMD housing for diverting high-frequency energy away from the connectable lead to the AIMD housing for dissipation of the high-frequency energy; and c) an impeding circuit associated with the diversion circuit, the impeding circuit providing for raising the high-frequency impedance of the connectable lead or a leadwire, the impeding circuit being disposed between the diversion circuit and AIMD electronic circuits;

d) wherein the impeding circuit comprises at least one inductor; and e) wherein the at least one inductor comprises an inductor wire wound onto a ferromagnetic or non-ferromagnetic mandrel.

23. A passive component network for an active implantable medical device, comprising:

a) an active implantable medical device (AIMD) comprising an electrically or thermally conductive housing, wherein the AIMD is configured to be connectable to a lead, the connectable lead comprising a length extending between and to a proximal end adjacent to the AIMD housing and a tissue-stimulating or biological-sensing electrode at a distal tip end; and b) a frequency selective energy diversion circuit for diverting high-frequency energy away from the connectable lead to the AIMD housing for dissipation of the high-frequency energy;

c) wherein the diversion circuit is disposed within the AIMD housing; and d) wherein the active implantable medical device (AIMD) comprises a deep brain stimulator.

24. A passive component network for an active implantable medical. device, comprising:

a) an active implantable medical device (AIMD) comprising an electrically or thermally conductive housing, wherein the AIMD is configured to be connectable to a lead, the connectable lead comprising a length extending between and to a proximal end adjacent to the AIMD housing and a tissue-stimulating or biological-sensing electrode at a distal tip end; and b) a frequency selective energy diversion circuit housed inside the AIMD for diverting high-frequency energy away from the connectable lead to the AIMD housing for dissipation of said high-frequency energy;

c) wherein the frequency selective energy diversion circuit is selected from the group consisting of a capacitor, an inductor, a Pi filter, a T filter, an LL filter, and an "n" element filter.

25. A decoupling circuit for an active implantable medical device, comprising:

a) an active implantable medical device (AIMD) comprising an electrically or thermally conductive housing;

b) a header block attached to the conductive housing;

c) an implantable lead receptacle disposed within the header block;

d) an AIMD electronic circuit disposed within the conductive housing and electrically coupled to the implantable lead receptacle by a conductor; and e) a frequency selective energy diversion circuit electrically coupled to the conductor for diverting high-frequency MRI energy away from the implantable lead receptacle or conductor to the AIMD housing for dissipation of the high-frequency MRI energy.

26. The decoupling circuit of claim 25, wherein the frequency selective energy diversion circuit is disposed within the conductive housing protecting the diversion circuit from direct contact with patient body fluid.

27. The decoupling circuit of claim 26, wherein the diversion circuit comprises at least one capacitor.

28. The decoupling circuit of claim 27, including an impeding circuit associated with the diversion circuit, the impeding circuit providing for raising the high-frequency impedance of the implantable lead receptacle or conductor, the impeding circuit electrically connected in series along the conductor disposed between the diversion circuit and the AIMD electronic circuit.

29. The decoupling circuit of claim 28, wherein the impeding circuit comprises at least one inductor.

30. The decoupling circuit of claim 26, wherein the diversion circuit comprises a LC trap filter.

31. The decoupling circuit of claim 28, wherein the impeding circuit comprises bandstop filter.

32. A decoupling circuit for an active implantable medical device, comprising:
   a) an active implantable medical device (AIMD) comprising an electrically or thermally conductive housing;
   b) a header block attached to the conductive housing;
   c) an implantable lead receptacle disposed within the header block;
   d) an AIMD electronic circuit disposed within the conductive housing and electrically coupled to the implantable lead receptacle by a conductor;
   e) a frequency selective energy diversion circuit electrically coupled to the conductor for diverting high-frequency MRI energy away from the implantable lead receptacle or conductor to the AMID housing for dissipation of the high-frequency MRI energy; and
   f) an impeding circuit electrically connected in series along the conductor and disposed between the diversion circuit and the AIMD electronic circuit for raising the high-frequency impedance of the implantable lead receptacle or the conductor.

33. The decoupling circuit of claim 32, wherein the frequency selective energy diversion circuit and impeding circuit are disposed within the conductive housing protecting the circuits from direct contact with patient body fluid.

34. The decoupling circuit of claim 33, wherein the diversion circuit comprises at least one capacitor.

35. The decoupling circuit of claim 33, wherein the impeding circuit comprises at least one inductor.

36. The decoupling circuit of claim 33, wherein the diversion circuit comprises a LC trap filter.

37. The decoupling circuit of claim 33, wherein the impeding circuit comprises a bandstop filter.

38. A decoupling circuit for an active implantable medical device, comprising:
   a) an active implantable medical device (AMID) comprising an electrically or thermally conductive housing and an implantable lead receptacle; and
   b) a frequency selective energy diversion circuit for diverting high-frequency MRI energy away from the implantable lead receptacle to the AIMD housing for dissipation of the high-frequency MRI energy.

39. The decoupling circuit of claim 38, wherein the frequency selective energy diversion circuit is disposed within the conductive housing protecting the diversion circuit from direct contact with patient body fluid.

40. The decoupling circuit of claim 39, wherein the diversion circuit comprises at least one capacitor.

41. The decoupling circuit of claim 39, wherein the diversion circuit comprises a LC trap filter.

42. The decoupling circuit of claim 39, including an impeding circuit associated with the diversion circuit, the impeding circuit providing for raising the high-frequency impedance of the implantable lead receptacle or conductor, the impeding circuit electrically connected in series along the conductor disposed between the diversion circuit and an AMID electronic circuit disposed within the AIMD housing.

43. The decoupling circuit of claim 42, wherein the impeding circuit comprises at least one inductor.

44. The decoupling circuit of claim 42, wherein the impeding circuit comprises a bandstop filter.

45. A decoupling circuit for an active implantable medical device, comprising:
   a) an active implantable medical device (AIMD) comprising an electrically or thermally conductive housing and an implantable lead receptacle;
   b) an AIMD electronic circuit disposed within the conductive housing;
   c) a conductor electrically coupling the implantable lead receptacle to the AIMD electronic circuit, the conductor defined as comprising a first node and a second node disposed in series along the conductor, the first node disposed closer to the implantable lead receptacle and the second node disposed closer to the AIMD electronic circuit;
   d) a first frequency selective energy diversion circuit for diverting high-frequency MRI energy away from the implantable lead receptacle to the conductive housing for dissipation of high-frequency MRI energy, the first diversion circuit electrically connected between the first node and the conductive housing;
   e) an impeding circuit for raising the high-frequency impedance of the implantable lead receptacle or conductor, the impeding circuit electrically connected in series along the conductor disposed between the first and second nodes; and
   f) a second frequency selective energy diversion circuit electrically connected between the second node and the conductive housing.

46. The decoupling circuit of claim 45, wherein the first diversion circuit comprises a capacitor.

47. The decoupling circuit of claim 46, wherein the impeding circuit comprises a bandstop filter.

48. The decoupling circuit of claim 47, wherein the second diversion circuit comprises a LC trap filter.

49. The decoupling circuit of claim 48, wherein the first diversion circuit, the impeder circuit and the second diversion circuit are disposed within the conductive housing protecting the circuits from direct contact with patient body fluid.

50. An energy dissipating surface housing for an active implantable medical device, comprising:
   a) an active implantable medical device (AMID) comprising an electrically or thermally conductive housing, wherein the conductive housing comprises an energy dissipating surface;
   b) a header block attached to the conductive housing;

c) an implantable lead receptacle disposed within the header block;
d) an AIMD electronic circuit disposed within the conductive housing and electrically coupled to the implantable lead receptacle by a conductor; and
e) a frequency selective energy diversion circuit electrically coupled between the conductor and the conductive housing for diverting high-frequency MRI energy away from the implantable lead receptacle or conductor to the AIMD housing for dissipation of the high-frequency MRI energy.

51. The housing of claim 50, including an impeding circuit electrically coupled to the conductor for raising the high-frequency impedance of the implantable lead receptacle or conductor, the impeding circuit electrically connected in series along the conductor disposed between the diversion circuit and the AIMD electronic circuit.

52. The housing of claim 51, wherein the frequency selective energy diversion circuit and impeding circuit are disposed within the conductive housing protecting the diversion circuit and impeding circuit from direct contact with patient body fluid.

53. The housing of claim 52, wherein the diversion circuit comprises at least one capacitor.

54. The housing of claim 52, wherein the impeding circuit comprises at least one inductor.

55. The housing of claim 52, wherein the diversion circuit comprises a LC trap filter.

56. The housing of claim 52, wherein the impeding circuit comprises a bandstop filter.

* * * * *

UNITED STATES PATENT AND TRADEMARK OFFICE
CERTIFICATE OF CORRECTION

PATENT NO. : 8,219,208 B2  
APPLICATION NO. : 12/751711  
DATED : July 10, 2012  
INVENTOR(S) : Stevenson et al.

Page 1 of 1

It is certified that error appears in the above-identified patent and that said Letters Patent is hereby corrected as shown below:

Column 45, Claim 1, line 1 delete "lead connectable" and insert --connectable lead--

Column 48, Claim 42, line 16 delete "AMID" and insert --AIMD--

Column 48, Claim 50, line 63 delete "(AMID)" and insert --(AIMD)--

Signed and Sealed this  
Thirteenth Day of November, 2012

David J. Kappos  
*Director of the United States Patent and Trademark Office*